(12) United States Patent
Mikolajczyk et al.

(10) Patent No.: US 9,671,407 B2
(45) Date of Patent: *Jun. 6, 2017

(54) DEVICES AND METHODS OF CELL CAPTURE AND ANALYSIS

(71) Applicant: Biocept, Inc., San Diego, CA (US)

(72) Inventors: Stephen D. Mikolajczyk, San Diego, CA (US); Tony Pircher, San Diego, CA (US); Farideh Z. Bischoff, Sugar Land, TX (US); Pavel Tsinberg, Carlsbad, CA (US)

(73) Assignee: BIOCEPT, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/223,980

(22) Filed: Mar. 24, 2014

(65) Prior Publication Data

US 2015/0056614 A1 Feb. 26, 2015

Related U.S. Application Data

(63) Continuation of application No. 13/269,532, filed on Oct. 7, 2011, now abandoned, which is a (Continued)

(30) Foreign Application Priority Data

Mar. 24, 2010 (WO) .............. PCT/US2010/028499

(51) Int. Cl.
*G01N 33/574* (2006.01)
*G01N 33/543* (2006.01)
(Continued)

(52) U.S. Cl.
CPC ..... *G01N 33/57492* (2013.01); *C12Q 1/6886* (2013.01); *G01N 33/54306* (2013.01);
(Continued)

(58) Field of Classification Search
CPC ....... G01N 33/57492; G01N 33/54306; G01N 33/56966; G01N 33/57415;
(Continued)

(56) References Cited

U.S. PATENT DOCUMENTS 6,368,871 B1 4/2002 Christel et al.
6,613,525 B2 9/2003 Nelson et al.
(Continued)

FOREIGN PATENT DOCUMENTS

CN 1871517 A 11/2006
CN 101102847 A 1/2008
(Continued)

OTHER PUBLICATIONS

Final Office Action in U.S. Appl. No. 12/730,738, mailed May 5, 2014.
(Continued)

*Primary Examiner* — Gail R Gabel
(74) *Attorney, Agent, or Firm* — Cooley LLP

(57) ABSTRACT

The present invention provides a device for isolating target biomolecules or cells from samples, particularly biological samples. In particular, the device comprises a loading mixture, which contains the biological sample and a first binding entity that specifically binds to the target biomolecule or target cell; and a micro-channel coated with a second binding entity that binds directly or indirectly to the first binding entity. Methods of capturing, detecting, and/or evaluating target biomolecules or target cells (e.g. cancer cells) in biological samples are also disclosed.

14 Claims, 47 Drawing Sheets

Cells Pre-labeled with Ab Prior to Enrichment on Streptavidin Channel

Related U.S. Application Data continuation-in-part of application No. 12/730,738, filed on Mar. 24, 2010, now Pat. No. 9,128,082.

(60) Provisional application No. 61/431,385, filed on Jan. 10, 2011, provisional application No. 61/163,009, filed on Mar. 24, 2009, provisional application No. 61/298,871, filed on Jan. 27, 2010, provisional application No. 61/235,615, filed on Aug. 20, 2009.

(51) Int. Cl.
*G01N 33/569* (2006.01)
*C12Q 1/68* (2006.01)

(52) U.S. Cl.
CPC . *G01N 33/56966* (2013.01); *G01N 33/57415* (2013.01); *G01N 33/57423* (2013.01); *G01N 33/57434* (2013.01); *G01N 33/57446* (2013.01); *G01N 33/57496* (2013.01); *C12Q 2600/156* (2013.01); *G01N 2333/4742* (2013.01); *G01N 2333/71* (2013.01)

(58) Field of Classification Search
CPC ....... G01N 33/57423; G01N 33/57434; G01N 33/57446; G01N 33/57496; C12Q 1/6886
See application file for complete search history.

(56) References Cited

U.S. PATENT DOCUMENTS

| | | | |
|---|---|---|---|
| 6,893,881 B1 * | 5/2005 | Fodstad | G01N 33/54326 435/174 |
| 8,008,032 B2 * | 8/2011 | Forsyth | G01N 33/574 422/417 |
| 9,128,082 B2 * | 9/2015 | Mikolajczyk | G01N 33/54306 |
| 2002/0172987 A1 | 11/2002 | Terstappen et al. | |
| 2004/0197832 A1 | 10/2004 | Amiel et al. | |
| 2005/0123914 A1 * | 6/2005 | Katz | C12Q 1/6881 435/6.12 |
| 2005/0181429 A1 | 8/2005 | Fejgin et al. | |
| 2006/0000772 A1 | 1/2006 | Sano et al. | |
| 2006/0160243 A1 | 7/2006 | Tang et al. | |
| 2007/0161051 A1 | 7/2007 | Tsinberg et al. | |
| 2009/0215088 A1 | 8/2009 | Forsyth et al. | |
| 2010/0255479 A1 | 10/2010 | Mikolajczyk et al. | |
| 2012/0100538 A1 | 4/2012 | Mikolajczyk et al. | |

FOREIGN PATENT DOCUMENTS

| | | |
|---|---|---|
| CN | 101374939 A | 2/2009 |
| JP | 0480657 | 3/1992 |
| JP | 2000-508171 | 7/2000 |
| JP | 2003-75444 | 3/2003 |
| JP | 2006-513695 | 4/2006 |
| JP | 2006-521821 | 9/2006 |
| JP | 2007-501407 | 1/2007 |
| JP | 2007-525642 | 9/2007 |
| JP | 2008-503498 | 2/2008 |
| WO | WO 84/02193 | 6/1984 |
| WO | WO 00/00826 | 1/2000 |
| WO | WO 03/020986 A1 | 3/2003 |
| WO | WO 03/050537 | 6/2003 |
| WO | WO 03/065042 | 8/2003 |
| WO | WO 03/106495 | 12/2003 |
| WO | WO 2004/091384 A2 | 10/2004 |
| WO | WO 2004/076643 A2 | 11/2004 |
| WO | WO 2004/106925 | 12/2004 |
| WO | WO 2005/089253 | 9/2005 |
| WO | WO 2006/002114 | 1/2006 |
| WO | WO 2006/119203 | 11/2006 |
| WO | WO 2007/075270 | 7/2007 |
| WO | WO 2007/082302 | 7/2007 |
| WO | WO 2008/011486 | 1/2008 |
| WO | WO 2008/149803 | 12/2008 |
| WO | WO 2008/156906 | 12/2008 |
| WO | WO 2009/024691 | 2/2009 |
| WO | WO 2009/029601 | 3/2009 |
| WO | WO 2009/039507 A2 | 3/2009 |

OTHER PUBLICATIONS

Advisory Action in U.S. Appl. No. 12/730,738, mailed Oct. 14, 2014.
Bischoff et al., Cell-free fetal DNA and intact fetal cells in maternal blood circulation: implications for first and second trimester non-invasive prenatal diagnosis, Human Reproduction Update, vol. 8, No. 6, 2002, pp. 493-500.
Dickson, Mary Nora, et al., "Efficient capture of circulating tumor cells with a novel immunocytochemical microfluidic device", BioMicrofluidics 5, pp. 34119-34115 (2011).
Hager, Gudrun et al., The use of a panel of monoclonal antibodies to enrich circulating breast cancer cells facilitates their detection, <Gynecologic Oncology>, bol. 98, No. 2, Aug. 2005; p. 211-216.
Holdenrieder et al., Apoptosis in Serum of Patients with Solid tumors, Anticancer Research, vol. 19, 1999, pp. 2721-2724.
Katz-Jaffe, DNA identification of fetal cells isolated from cervical mucus: potential for early non-invasive prenatal diagnosis, BJOG, vol. 112, May 2005, pp. 595-600.
Loo, et al., "Antibody-based identification of cell surface antigens: targets for cancer therapy", Current Opinion in Pharmacology, vol. 8, No. 5.
Miller et al., Transcervical recovery of fetal cells from the lower uterine pole: reliability of recovery and histological/immunocytochemical analysis of recovered cell populations, Human Reproduction, vol. 14, No. 2, 1999, pp. 521-531.
Nagrath et al. Isolation of rare circulating tumour cells in cancer patients by microchip technology, Nature 450 (7173): 1235-1239 (Dec. 2007).
Int'l Preliminary Report on Patentability, PCT/US2007/066475, issued Oct. 14, 2008.
Int'l Preliminary Report on Patentability, PCT/US2008/077251, issued Mar. 24, 2010.
International Search Report and Written Opinion in PCT/US2010/028499 mailed Dec. 23, 2010.
Int'l Search Report, WO2009/039507 A3, mailed Apr. 15, 2009.
Supplementary European Search Report issued in EP 10756790.1 dated Aug. 13, 2012.
Office Action issued in U.S. Appl. No. 12/730,738 mailed Aug. 7, 2013.
Office Action issued in CN Application No. 201080019566.9 dated Sep. 18, 2013 (and English translation).
Office Action issued in EP Application No. 10756790.1 dated Jun. 18, 2013.
Office Action issued in JP Application No. 2012-502208 dated Dec. 16, 2013 (and English translation).

* cited by examiner

DEVICES AND METHODS OF CELL CAPTURE AND ANALYSIS

RELATED APPLICATIONS

This application is a continuation of U.S. application Ser. No. 13/269,532, filed Oct. 7, 2011, now abandoned, which is a continuation-in-part of U.S. application Ser. No. 12/730,738, filed Mar. 24, 2010, which issued as U.S. Pat. No. 9,128,082 on Sep. 8, 2015. The Ser. No. 13/269,532 application claims priority to U.S. Provisional Application No. 61/431,385, filed Jan. 10, 2011 and PCT Application No. PCT/US2010/028499, filed Mar. 24, 2010. The Ser. No. 12/730,738 application claims benefit of U.S. Provisional Application No. 61/235,615, filed Aug. 20, 2009, U.S. Provisional Application No. 61/163,009, filed Mar. 24, 2009, and U.S. Provisional Application No. 61/298,871, filed Jan. 27, 2010. The present application claims priority to all of these applications which are hereby incorporated by reference in their entireties.

DESCRIPTION OF THE TEXT FILE SUBMITTED ELECTRONICALLY

The contents of the text file submitted electronically herewith are incorporated herein by reference in their entireties: A computer readable format copy of the Sequence Listing (filename: BIOE_020_04US_SeqList_ST25.txt, date recorded Nov. 13, 2014, file size 1 kilobyte).

FIELD OF THE INVENTION

The present invention relates to micro-channel devices for capturing targets, such as cells and molecules of interest from solutions, as well as to post-capture analysis of circulating cells. In certain embodiments, the present invention relates to methods and devices for capturing target cells (e.g. circulating tumor cells) from physiological fluids, and analyses thereof.

BACKGROUND OF THE INVENTION

Isolation of target cells or molecules from heterogeneous samples remains a prominent interest for research applications as well as medical applications, such as diagnostics and therapeutics. In particular, separation of rare cell types from physiological tissues and bodily fluids obviates the need to obtain large tissue samples and avoids the risks associated with the procedures required to obtain such samples. For example, isolation of fetal cells from maternal blood samples for genetic testing avoids the risks associated with aminocentesis or chronic villus sampling. Isolation of circulating tumor cells from a patient would allow the clinician to evaluate the cancer and monitor pathological changes in the patient's tumor, as well as evaluate the efficacy of any on-going drug treatments without conducting invasive biopsy procedures.

Current methods for separating biological molecules and/or cells from heterogeneous samples typically entail the use of a high affinity binding partner (e.g. an antibody or antigen) coupled to a solid support. The heterogeneous sample is passed over the solid support and the target biological molecules or cells of interest are bound by the binding partner and retained on the solid support. The bound molecules or cells of interest can be subsequently analyzed for the presence of molecular genomic and proteomic information.

These current approaches suffer from several technical difficulties, one of which is the problem of non-specific binding. To minimize non-specific binding, one or more washing steps is required to remove other molecules and/or cells that are bound to the solid support or binding partner. In addition, the subsequent in situ analysis of cells on the channel by staining and hybridization procedures may subject the cells to harsh and denaturing conditions. These washing and analysis procedures can compromise the initial capture of the desired molecule or cell by subjecting the binding partner to conditions that may cause the binding partner to degrade, lose some of its conformational structure, or become detached from the solid support.

Further still, existing methods for analyzing circulating cells (e.g., as captured from a patient sample) for malignancy, such as staining cells for cytokeratin (CK), have limitations as markers for identifying and/or evaluating circulating tumor cells.

Thus, there is a need in the art for additional methods and devices for isolating biological molecules and/or cells of interest from samples, as well as methods for subsequent analysis of captured targets, such as analysis of captured, circulating tumor cells.

SUMMARY OF THE INVENTION

The present invention provides devices and methods for capturing and/or analyzing biological targets from fluid samples. In various embodiments, the invention provides methods for capturing circulating tumor cells from biological samples, for the evaluation of a cancer patient's disease. In these and other embodiments, the invention provides methods for identifying and/or evaluating circulating cells for malignancy without or independent of CK status.

In one aspect, the invention provides a method for capturing biological targets from solution. In this aspect, the present invention is based, in part, on the discovery that pre-labeling or pre-mixing a sample containing a target (e.g., a cell) of interest with a binding partner that specifically binds to the cell enhances the capture of such targets in a micro-channel device.

In certain embodiments, the device comprises a micro-channel and a loading mixture. The micro-channel may comprise a population of posts distributed on the surface of the micro-channel in random pattern. The loading mixture may comprise a biological sample suspected of containing a target, such as a target cell, and also comprises a first binding entity. The first binding entity specifically binds to the target (e.g., a target entity on a target cell). The surface of the micro-channel is coated with a second binding entity that specifically binds, directly or indirectly, to the first binding entity. In some embodiments, the loading mixture further comprises a third binding entity conjugated to a detectable or capturable entity. For example, the first binding entity may be a primary antibody, the third binding entity may be a secondary antibody that specifically binds to the primary antibody, and the second binding entity specifically binds directly or indirectly to the secondary antibody. In one embodiment, the third binding entity is a biotinylated secondary antibody that specifically binds to the first binding entity and the second binding entity is avidin. The secondary antibody may be intact antibody or any antibody fragment such as Fab'2, Fab' or Fab. In addition this may include any of the genetically engineered or expressed forms of antibody fragment such as single chain Fab fragment or single chain variable fragment.

In another aspect, the present invention provides a method for capturing and/or detecting a target cell in a biological sample, including rare cell populations as described herein. In one embodiment, the method comprises contacting a biological sample with a first binding entity to form a pre-loading mixture, wherein the first binding entity specifically binds to a target entity on the surface of the target cell; passing the pre-loading mixture through a micro-channel, wherein the surface of the micro-channel is coated with a second binding entity capable of specifically binding to the first binding entity; and detecting the presence of the target cell on the surface of the micro-channel. The biological sample can be a physiological or bodily fluid or tissue, such as blood, plasma, serum, bone marrow, semen, vaginal secretions, urine, amniotic fluid, cerebral spinal fluid, synovial fluid, fine needle aspirates (FNAs) or biopsy tissue sample. In certain embodiments, the target cell is rare and present at a low ratio in the biological sample. Examples of target cells that are rare in the biological samples (e.g., blood) include circulating tumor cells (CTCs), cells that are in early stages of a disease state such as Stage 1 of tumorigenesis, as well as viral-, bacterial-, or fungal-infected cells.

In certain embodiments, the target cell is a cancer cell (e.g., a circulating tumor cell), such as a breast cancer cell, a prostate cancer cell, a colorectal cancer cell, a lung cancer cell, a pancreatic cancer cell, an ovarian cancer cell, a bladder cancer cell, an endometrine or uterine cancer cell, a cervical cancer cell, a liver cancer cell, a renal cancer cell, a thyroid cancer cell, a bone cancer cell, a lymphoma cell, a melanoma cell and a non-melanoma skin cancer cell. The tumor may be an epithelial tumor. In such embodiments, the first binding entity can be an antibody that specifically binds to circulating epithelial cells. In one embodiment, the first binding entity is an epithelial cell adhesion molecule antibody (e.g., EpCAM). In these and other embodiments, the first binding entity is a biotinylated-antibody and the second binding entity is avidin. In various embodiments, the invention involves antibody cocktails as the first binding entity, so as to capture circulating tumor cells exhibiting a range of epithelial, mesenchymal, stem or progenitor cell characteristics.

In another embodiment of the invention, the pre-loading mixture further comprises a third binding entity. In such embodiments, the first binding entity may be a primary antibody, the third binding entity may be a secondary antibody conjugated to a detectable or capturable entity and the secondary antibody specifically binds to the first binding entity. A second binding entity specifically binds to the third binding entity via the capturable moiety. In certain embodiments, the third binding entity is a biotinylated secondary antibody that specifically binds to the first binding entity, and the second binding entity is avidin.

In some embodiments, the method further comprises, after cell capture, cross-linking the target cell bound to the surface of the micro-channel. Cross-linking reagents include protein cross-linking reagents, such as a hydrophilic homobifunctional NHS crosslinking reagent. In certain embodiments, the captured cells can be subjected to further analysis in the micro-channel or outside the channel post capture.

In another aspect, the invention provides a method for post-capture analysis of circulating cells, and in particular, to examine or evaluate the circulating cells for malignancy. Generally, the invention in this aspect involves evaluating captured cells for aneuploidy, optionally with evaluation of other markers of malignancy, including mutations. In some embodiments, the method does not involve determining, or is independent of, cytokeratin expression, or alternatively, the method is conducted together with analysis of CK expression.

BRIEF DESCRIPTION OF THE DRAWINGS

(FIG. 18: 2) Next, a suspension of cells is drawn through the channel. Wherever a CTC makes contact with a post, the biotin on its surface reacts with streptavidin, thus immobilizing labeled cells. (FIG. 18: 3) Next, the captured cells are fluorescently stained (FIG. 18: 4) and counted using fluorescent microscopy (FIG. 18: 5). Modifications to this procedure allow for measurement of the effects of anti-clumping reagent (FIG. 18: 6) and bystander white blood cells (FIG. 18: 7), as done in Part I. An additional pre-labeling step allows for tumor cells incubated under multiple antibody conditions to be run simultaneously in one channel at a particular flow rate, as done in Part II (FIG. 18: 8). Cell lines, antibody preparation and microchannel set-up are identical for all experiments run.

FIG. 32A. The relative stain intensity of these cells on a microscope slide using anti-mouse-AlexaFluor488 when the cells were pre-incubated with anti-EpCAM antibody only, or with an antibody mixture of anti-HER2/neu, anti-CD44 and anti-CD28. FIG. 32B. The FACS profile of the respective antigens of EpCAM or of the 3-antibody mixture was present on each cell. FIG. 32C. The percentage capture of SKOV cells when pre-incubated with anti-EpCAM or the antibody mixture. This shows that much lower antigens are necessary for good cell capture than for good staining intensity. Antibody mixtures improve staining efficiency.

DETAILED DESCRIPTION

Figure 1:
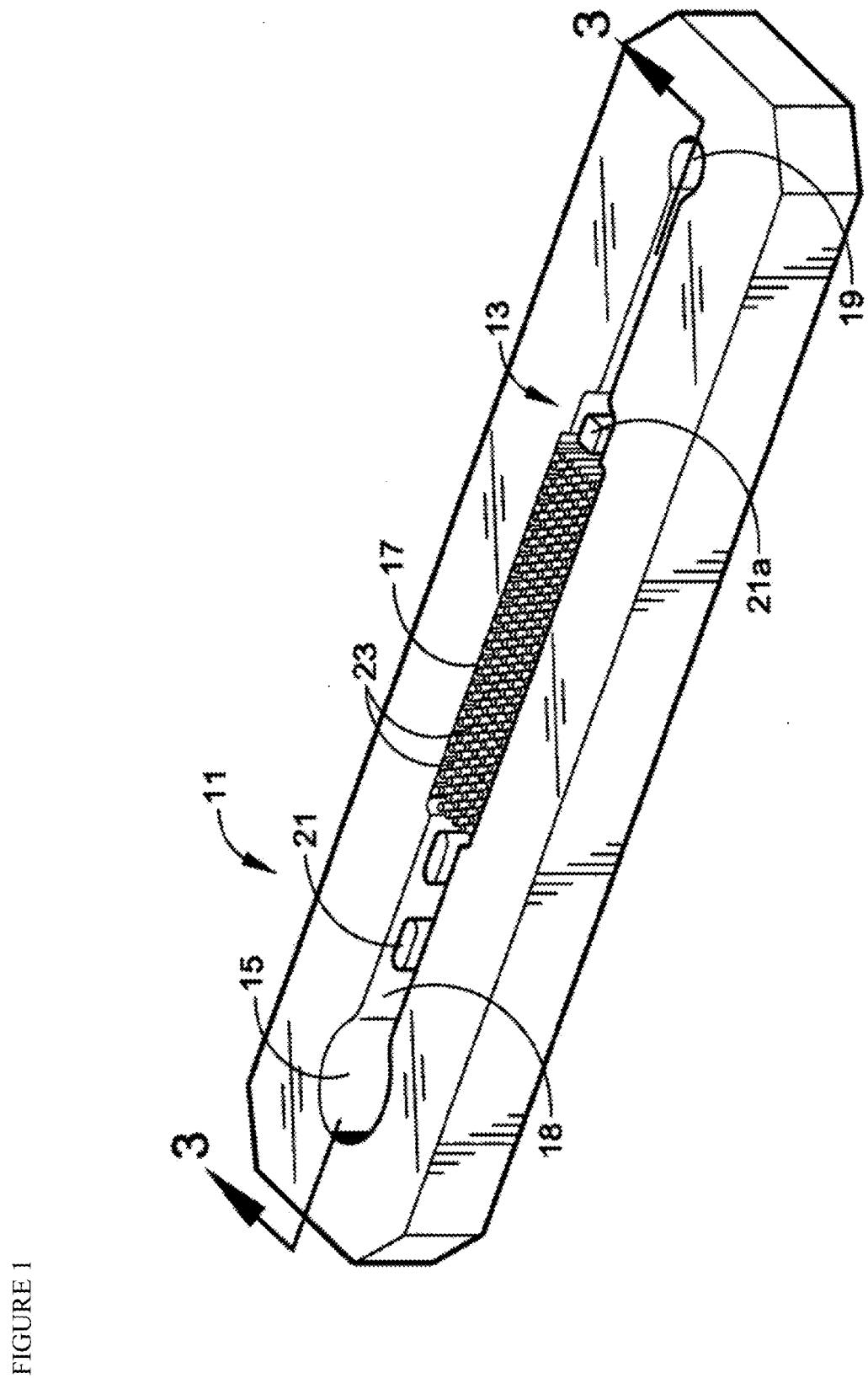
FIG. 1 is a perspective view of one embodiment of a micro-channel device comprising a post-containing collection region in the micro-channel.

The present invention provides devices and methods for capturing and/or analyzing biological targets from fluid samples. In various embodiments, the invention provides methods for capturing circulating tumor cells from biological samples, for the evaluation of a cancer patient's disease. In these and other embodiments, the invention provides methods for identifying and/or evaluating circulating cells for malignancy without or independent of cytokeratin expression.

In one aspect, the invention is based, in part, on the discovery that pre-labeling or pre-mixing a sample containing a target of interest with a binding partner that specifically binds to the target allows, e.g., enhances the capture of such targets in a micro-channel device, such as a microchannel device described herein. This approach also provides flexibility in the type and nature of primary antibodies that may be used to label cellular antigens. Accordingly, the present invention provides a novel device and method for separating biomolecules or cells of interest from samples, particularly biological samples. In one embodiment, the device comprises a micro-channel and a loading mixture. The micro-channel may comprise a population of posts distributed on the surface of the micro-channel in random pattern. The loading mixture may comprise a biological sample suspected of containing a target cell and a first binding entity, wherein the first binding entity specifically binds to a target entity on the target cell. The surface of the micro-channel is coated with a second binding entity that specifically binds to the first binding entity, either directly or indirectly.

Any suitable micro-channel device may be used in connection with the present invention. In some embodiments, the micro-channel device comprises a plurality of pre-determined flow paths. In some embodiments, the micro-channel device comprises posts or obstacles arranged in a random pattern or a regular or repeat pattern. In some embodiments, the micro-channel device comprises regions providing streamlined flow or random non-streamlined flow for any fluid passing through.

The micro-channel device may be a random-flow device for separating biomolecules or cells as described in detail in U.S. Published Application No. 2006/0160243, which is hereby incorporated by reference in its entirety. Such devices can be modified as described herein for use in connection with the invention. In general, the random-flow micro-channel device includes a substrate or support that has a flow path defined therein that includes at least one micro-channel having a collection region, which flow path is linked to a sample inlet and a liquid outlet. In some embodiments, the flow path may include several micro-channels, arranged in series, each of which has one such collection region. Alternatively, a random flow micro-channel may have more than one collection region, arranged in series, and there may also have more than one inlet and more than one outlet. One particular embodiment of the random flow micro-channel device is described in Example 1 and illustrated in FIG. 1.

The collection region of the random flow micro-channel can contain a plurality of upstanding posts that are aligned transverse to the liquid flow path and arranged in an irregular, random pattern across the entire width of the collection region portion of the flow channel. In one embodiment, the pattern of the posts is such that there can be no straight-line flow through the collection region and/or that streamlined flow streams are disrupted, assuring there is good contact between the liquid being caused to flow along the flow path and the surfaces of the posts. The posts in general are integral with the flat base of the collection region and extend perpendicular thereto, presenting surfaces that are vertical relative to a horizontal path of liquid being caused to flow through the flow channel of the substrate or support.

The placement and shape of the posts in the patterned post collection region can be engineered for optimal fluid dynamics and enhancement of capture of target cells through their specific surface characteristics. Very generally, in most instances, the preferred shape of the horizontal cross-section of the transverse fixed posts avoids sharp angles which might promote nonspecific binding to the transverse surfaces of the posts. The posts have rectilinear exterior surfaces and preferably have either a generally circular cross sectional shape or regular polygonal of 6 or more sides. Alternative shapes that might be used are a tear-drop shape where the tip is at the downstream end and shallowly curved, or oval shape; however, should more impact be desired, a square shape could be used. In one embodiment, the pattern of the posts should create a flow pattern in the liquid stream which enhances the capture of target cells by the second binding entity attached to the surfaces of the posts, the base and the facing surface. To achieve this end, the posts, e.g., should be of different sizes and be arranged in a set random pattern. A random pattern of posts of different cross sectional sizes, e.g. circular cross section posts of at least about 3 or 4 different sizes, about 70 to about 130 microns in diameter, in a collection region 100 microns high, where the minimum separation spacing between posts is about 50 μm to about 70 μm and preferably about 60 μm. In some embodiments, the cross sectional sizes of the posts are about 60 microns in diameter to about 150 microns in diameter, about 75 microns to about 150 microns, about 60 microns to about 130 microns, about 40 microns to about 100 microns, about 50 to about 80 microns or about 50 to about 60 microns, in a collection region about 55 microns to about 100 microns high where the minimum separation spacing between posts is about 50 μm to about 80 μm and preferably about 60 μm.

In some embodiments, the cross sectional area of the posts, which all have sidewalls formed by parallel lines which are perpendicular to the base, is such that they occupy between about 10 to 40% or about 15 to 25% of the volume of the collection region. In some embodiments, the post pattern will be such that they occupy about 20% to about 25% of the volume of the collection region, leaving a void volume for liquid flow of about 75% to about 80%. Preferably the post pattern will be such that they occupy about 20% of the volume of the collection region, leaving a void volume for liquid flow of about 80%. The posts are substantially spaced apart from one another, e.g. by at least about 60 microns, and posts of different sizes are preferably located upstream and downstream of one another. Smaller posts may create eddy regions downstream of larger posts, and as a result of the flow pattern that is generated, the surfaces in the vicinity may show particular effectiveness in capturing target cells.

Generally, the substrate component of the micro-channel device can be made from any suitable laboratory-acceptable material, such as silicon, fused silica, glass and polymeric materials. It may be desirable to use a material that is optically transparent, particularly when a diagnosis function is desired to be optionally employed. In its simplest embodiment, the substrate carrying the fabricated micro-channel is sealed with a plate having a flat surface that will abut the facing surface of the substrate. Such plate may be fabricated from the same material or may simply be a cover plate made of glass. Suitable plastics which may be used include polydimethylsiloxane (PDMS), polymethylmethacrylate (PMMA), polycarbonate, polystyrene, polyethylene teraphthalate, as well as other polymeric resins well known for acceptable laboratory material usage. Such patterned substrates may be fabricated using any convenient method such as those selected from among conventional molding and casting techniques.

Substrates may be conveniently fabricated from polymeric materials using a master or negative mold structure, which can be created in a thick negative photoresist, using optical lithography, as well known in this art. For instance, the construction layer can be formed from a mixture of commercially available, standard grade epoxy resin (EPON SU-8) photoresist and hardener (SU-82025), which may be spun onto silicon wafer substrates at 2000 rpm to provide, for example, a 40 or 50 µm thick film of such photoresist. The thickness determines the height of the flow path in the collection region. The film is subjected to pre-exposure baking for 3 minutes at 60° C. and then 7 minutes at 95° C. on a precisely level hot plate to assure even thickness throughout, and the resultant samples are cooled to room temperature. A Karl Suss Contact Mask Aligner is used to expose a film with the desired pattern for the flow path in the ultimate device. The film is then post-baked at 65° C. for 2 minutes and then at 95° C. for 5 minutes before it is developed in a commercial SU-8 developer for 5 minutes, with light stirring being applied during developing. This creates a negative pattern mold in the epoxy resin photoresist that is then used as a molding master for replication of patterned post substrates in PDMS or other suitable polymeric resin. The layout and the dimensions of the microchannel and of patterned posts in the collection region are determined by the mask used in exposure step of the fabrication of the master mold. The depth of the microchannel is controlled by the thickness of the SU-8 layer of the master mold, which is determined by spin-coating conditions.

The invention further involves a loading mixture that comprises a biological sample suspected of containing a target (e.g., a target cell), and also comprises a first binding entity. The biological sample can include, but is not limited to, a physiological or bodily fluid or tissue or a cell mixture isolated from a biological sample. For example, the biological sample can include, without limitation, blood, plasma, serum, semen, vaginal secretions, urine, saliva, amniotic fluid, cerebral spinal fluid, synovial fluid, a fine needle aspirate (FNA), and a biopsy tissue sample. A target cell can be any cell comprising a detectable surface antigen, such as a cancer cell, stem cell, fetal cell, a viral-, a bacterial- or a fungal-infected cell. In some embodiments, the target cell is a cancer cell. In certain embodiments, the target cell is rare and is present at a low ratio in the biological sample, or expresses a very low level of a particular antigen of interest. Examples of target cells that are rare in the biological samples include circulating tumor cells (CTCs), cells that are in early stages of a disease state such as cells at Stage 1 of tumorigenesis, early viral-, bacterial, or fungal-infections.

Preferably, the first binding entity specifically binds to a target entity on the target cell. The first binding entity can include, but is not limited to, an antibody, an antigen, an aptamer, a nucleic acid (e.g. DNA and RNA), a protein (e.g. receptor, enzyme, enzyme inhibitor, enzyme substrate, ligand), a peptide, a lectin, a fatty acid or lipid and a polysaccharide. In one embodiment, the first binding entity is an antibody. In another embodiment, the first binding entity comprises a binding entity mixture having at least a first antibody and a second antibody, and wherein the first antibody specifically binds to a first epitope of the target entity and the second antibody specifically binds to a second epitope of the target entity. The first binding entity can comprise a mixture of antibodies or binding entities directed to the one or more target antigens on the cell, or one or more epitopes of the target antigen, or a combination thereof. As used herein the term "epitope" can refer to a binding region on a singular antigen or a binding region on a second antigen. By way of example, in some embodiments, the first antibody binds to a first epitope on a first antigen and the second antibody binds to a second epitope on the first antigen. In other embodiments, the first antibody binds to a first epitope on a first antigen and the second antibody binds to a second epitope on a second antigen. In certain embodiments, the antibodies may be conjugated to a tag molecule including, but not limited to biotin, digoxigenin, FLAG epitope, or polyhistidine.

In another embodiment of the invention, the loading mixture further comprises a third binding entity conjugated to a detectable or capturable entity. For example, the first binding entity may be a primary antibody or ligand, the third binding entity is a secondary antibody or ligand that specifically binds to the first binding entity, and the second binding entity specifically binds to the third binding entity. A primary antibody can include a monoclonal antibody, a polyclonal antibody, or partially purified antibodies. The secondary antibody can be an antibody that binds to the constant region of the primary antibody. By way of example, if the primary antibody is a mouse antibody, the secondary antibody may be an anti-mouse antibody. The detectable or capturable entity conjugated to the secondary antibody can be a tag including, but not limited to, biotin, digoxigenin, FLAG epitope, or polyhistidine. In one embodiment, the loading mixture further comprises a third binding entity, wherein the first binding entity is a primary antibody, the third binding entity is a biotinylated secondary antibody that specifically binds to the first binding entity and the second binding entity is avidin. As used herein, the term "avidin" includes any expressed or engineered form of the avidin biotin-binding molecule, such as streptavidin, neutravidin and the like.

The surface of the micro-channel of the device is coated with a second binding entity that specifically binds to the first binding entity. The second binding entity can be an antibody, an antigen, an aptamer, a nucleic acid (e.g. DNA and RNA), a protein (e.g. receptor, enzyme, enzyme inhibitor, enzyme substrate, ligand), a peptide, a lectin, a fatty acid or a lipid, and/or a polysaccharide. The second binding entity may be the same type of molecule as the first binding entity (e.g. antibody-antibody or nucleic acid-nucleic acid) or it may be a different type of molecule than the first binding entity (e.g. nucleic acid-protein). The second binding entity can directly bind to the first binding entity or it can indirectly bind to the first binding entity through a tag molecule. For instance, if the first binding entity is a biotinylated primary antibody, the second binding entity can be avidin. In one embodiment, the second binding entity is avidin. In some embodiments, the loading mixture can comprise both a first binding entity and a third binding entity, wherein the first binding entity binds to a target entity (e.g., on the target cell) and the third binding entity specifically binds to the first binding entity. In such embodiments, the second binding entity specifically binds to the third binding entity either directly or indirectly through a detectable entity. By way of example, if the first binding entity is a mouse primary antibody and the third binding entity is an anti-mouse antibody conjugated to digoxigenin, then the second binding entity can be an anti-digoxigenin antibody.

The polymeric surface of the micro-channel and/or the patterned post or obstacle region comprised therein can be derivatized in various ways to enable the attachment of the second binding entity onto all the surfaces. For example, after plasma treatment and closure of the micro-channel-carrying substrate, a 1 to 50 volume % solution of an aminofunctional silane (e.g. a 3% solution of Dow Corning Z-6020), or a thio-functional silane, in ethanol may be injected into the micro-channel to fill the collection region between the sample inlet and sample outlet regions, and the flooded micro-channel can then be left to incubate for 30 minutes at room temperature. Derivitization can be performed on a non-fully cured polymer, such as PDMS, before the closure of the micro-channel region with a plate. In such case, an alternative is to slightly undercure the PDMS substrate and then complete the curing after affixing the seal plate and treating with the substituted silane or other functionalizing reagent. For example, a final heating step of about 90 minutes at about 50 to 90° C. might be used to complete the curing after treating with the Z-6020. Alternatively, one or two days at room temperature would also complete the curing. Such derivatization treatment can also be performed before the closure of the micro-channel region because derivatization of the facing flat surface is of no real consequence. The flow path is then purged with ethanol, and the micro-channel is ready for attachment of the second binding entity.

Second binding entities can be directly or indirectly immobilized upon the surfaces of the posts, obstacles, and/or the micro-channel, and the surfaces can be pre-treated and/or coated to facilitate attachment. In some embodiments, indirect immobilization is preferred and contemplates the employment of an intermediate agent or substance that is first linked to the post or surface. It may be desired to use coupling pairs to link to the intermediate agent. For example, avidin, or an antibody directed against another species antibody, might be attached to the intermediate agent, such as a NHS/maleimide heterobifunctional linker, which would thereafter couple to a biotinylated antibody or to an antibody of such other species.

Flow through the devices of the invention can be achieved by any suitable means, with or without exterior force. In one embodiment, flow through the devices of the invention is achieved by pumping, e.g. using a syringe pump or the like, or by vacuum that would draw liquid through from a reservoir at an inlet well provided by a large diameter inlet hole. Preferably such a well is included which has a capacity to hold about 50 µl to about 500 µl of liquid sample. In one embodiment, the design of the flow channel is such that, at flow rates through the device within a reasonable range (e.g. by injection of sample using a syringe pump or equivalent device, such as a Biocept syringe pump, or a standard Harvard Apparatus infusion syringe pump or other commercially available syringe pump) to create a flow in the collection region at a rate of about 0.01 to 100 mm per second, there is substantial disruption of streamlined flow through the region without creating turbulence. This results from the random arrangement of posts of different sizes and the relative spacing of the posts throughout the collection region. Relatively smooth, non-streamlined flow without dead spots is achieved at a preferred liquid flow rate of between about 0.3 to 10 mm/sec, and more preferably the flow rate is maintained between about 0.5 and 5 mm/sec and is achieved by suction from an inlet well of defined size. In some embodiments, the flow rate is about 0.1 mm to about 2 mm, or about 0.05 mm to about 5 mm.

In some embodiments, the flow rate is maintained from about 0.5 µL/min to about 100 µL/min. In some embodiments, the flow rate is from about 1 µL/min to about 75 µL/min, from about 1 µL/min to about 50 µL/min, about 1 µL/min to about 40 µL/min, 1 µL/min to about 30 µL/min, 1 µL/min to about 20 µL/min or about 1 µL/min to about 10 µL/min. In some embodiments, the flow rate is about 5 µL/min to about 30 µL/min, about 10 µL/min to 20 or about 15 µL/min to 20 µL/min. In certain embodiments, the flow rate is about 6 µL/min, about 9 µL/min, about 12 µL/min, about 15 µL/min or about 18 µL/min.

The antigen density can impact the target cell capture efficiency, such as for example for capturing rare circulating cells. Capture efficiency can be defined as the yield of target cells captured compared to the total number of target cells which have been introduced to the device; capture efficiency can be represented by:

$$C = \frac{n_{cap}}{n_D}$$

Overall capture efficiency for a device decreases with decreased antigen density per cell on a device. This relationship can be represented by:

$$C = \frac{x}{a + x}$$

where α represents the "half-point," which is the antigen density per cell corresponding to a capture efficiency of 50%. In some embodiments, the capture efficiency of the device is about 10%, about 20%, about 30%, about 40%, about 50%, about 60%, about 70%, about 80%, about 90% or about 100%. For the devices of the present invention, antigen density can range from about 1,000 to about 100,000. In some embodiments, the antigen density per cell is from about 10,000 to about 90,000; about 20,000 to about 80,000; about 30,000 to about 70,000; about 40,000 to about 60,000. In some embodiments, the antigen density is greater than or equal to about 30,000. In some further embodiments, the antigen density is greater than or equal to about 30,000 and results in a capture efficiency of greater than or equal to about 70%.

The present invention also provides a method for detecting a target cell in a biological sample using the devices described herein. For example, the method may comprise contacting a biological sample with a first binding entity to form a pre-loading mixture, wherein the first binding entity specifically binds to a target entity on the surface of the target cell, passing the pre-loading mixture through a micro-channel, wherein the surface of the micro-channel is coated with a second binding entity capable of specifically binding to the first binding entity, and detecting the presence of the target cell on the surface of the micro-channel. In certain embodiments, the micro-channel comprises a population of posts distributed on the surface of the micro-channel in random pattern.

Various types of biological samples, such as blood, plasma, serum, bone marrow, semen, vaginal secretions, urine, saliva, amniotic fluid, cerebral spinal fluid, synovial fluid, lung lavages, fine needle aspirates (FNAs) and biopsy tissue samples, are suitable for use in the methods of the invention. In one embodiment, the biological sample is a blood sample from a patient. The target cell can be present in the biological sample in the ratio of 1 out of $10^{10}$ cells, 1 out of $5 \times 10^7$, or 1 out of $10^4$ cells. A target cell can be any cell comprising a detectable surface antigen, such as a cancer cell, stem cell, fetal cell, a viral-, a bacterial-, or a fungal-infected cell.

In one particular embodiment, the target cell is a cancer cell. The cancer cell can be a cell from any type of cancer, such as an epithelial cancer, including, but not limited to, breast cancer cells, prostate cancer cells, colorectal cancer cells, lung cancer cells, pancreatic cancer cells, ovarian cancer cells, bladder cancer cells endometrial or uterine cancer cells, cervical cancer cells, liver cancer cells, renal or kidney cancer cells, thyroid cancer, bone cancer cells, lymphoma cells (e.g. Hodgkin's lymphoma, non-Hodgkin's lymphoma), melanoma cells, and non-melanoma skin cancer cells.

The first binding entity can be any of the molecules as described herein. In one embodiment, the first binding entity is an antibody. The first binding entity may be a biotinylated-antibody and the second binding entity may be avidin. In some embodiments, the first binding entity can be an antibody that specifically binds to circulating epithelial cells. The antibody can be an epithelial cell adhesion molecule (EpCAM) antibody, such as an antibody that specifically binds to an epithelial cell surface adhesion protein. The first binding entity may be a cocktail of two, three, four, five, or more antibodies, for example, as described herein for capture of target cancer cells. For example, the antibody cocktail may comprise at least antibody against an epithelial cell surface antigen, and at least one antibody against an antigen that is indicative of a mesenchymal phenotype, to thereby isolate cells having a range of epithelial and/or mesenchymal characteristics from the sample.

For example, where the target cell is a breast cancer cell, the first binding entity may be an antibody that specifically binds to EpCAM (epithelial cell adhesion molecule), Her2/neu (Human Epidermal growth factor Receptor 2), MUC-1, EGFR (epidermal growth factor receptor), TAG-12 (tumor associated glycoprotein 12), IGF1R (insulin-like growth factor 1 receptor), TACSTD2 (tumor associated calcium signal transducer 2), CD318, CD340, CD104, N-cadherin or a combination (e.g., cocktail) of two or more thereof.

In yet another embodiment, the target cell is a prostate cancer cell and the first binding entity is an antibody that specifically binds to EpCAM, MUC-1, EGFR, PSMA (prostate specific membrane antigen), PSA (prostate specific antigen), TACSTD2, PSCA (prostate stem cell antigen), PCSA (prostate cell surface antigen), CD318, CD104, N-cadherin or a combination thereof. In another embodiment, the target cell is a colorectal cancer cell and the first binding entity is an antibody that specifically binds to EpCAM, CD66c, CD66e, CEA (carcinoembryonic antigen), TACSTD2, CK20 (cytokeratin 20), CD104, MUC-1, CD318, N-cadherin or a combination thereof.

In still another embodiment, the target cell is a lung cancer cell and the first binding entity is an antibody that specifically binds to CK18, CK19, CEA, EGFR, TACSTD2, CD318, CD104, or EpCAM or a combination thereof. In another embodiment, the target cell is a pancreatic cancer cell and the first binding entity is an antibody that specifically binds to MUC-1, TACSTD2, CEA, CD104, CD318, N-cadherin, EpCAM or a combination thereof. In yet another embodiment, the target cell is an ovarian cancer cell and the first binding entity is an antibody that specifically binds to MUC-1, TACSTD2, CD318, CD104, N-cadherin, EpCAM or a combination thereof.

In another embodiment, the target cell is an endothelial bladder cancer cell and the first binding entity is an antibody that specifically binds to CD34, CD146, CD62, CD105, CD106, VEGF receptor (vascular endothelial growth factor receptor), MUC-1 or a combination thereof. In another embodiment, the target cell is an epithelial bladder cancer cell and the first binding entity is an antibody that specifically binds to TACSTD2, EpCAM, CD318, EGFR, 6B5 or Folate binding receptor.

The target cell may be a cancer stem cell, and the first binding entity may be an antibody that specifically binds to CD133, CD135, CD117, CD34 or a combination thereof.

In some embodiments, the target cell is a circulating cancer cell that expresses mesenchymal antigens and the first binding entity is an antibody (or antibody cocktail) that specifically binds to FGFR1, FGFR4, EGFR, N-cadherin, folate binding receptor, and MSC or a combination thereof.

In some embodiments, the target cell is a circulating cancer cell that expresses angiogenesis surface antigens and the first binding entity includes an antibody that specifically binds to a VEGF receptor.

In other embodiments, the target cell is a melanoma cancer cell and the first binding entity is an antibody that specifically binds to one or more of the melanocyte differentiation antigens, oncofetal antigens, tumor specific antigens, SEREX antigens or a combination thereof. Examples of melanocyte differentiation antigens, include but are not limited to tyrosinase, gp75, gp100, Melan A/MART 1 or TRP-2. Examples of oncofetal antigens include antigens in the MAGE family (MAGE-A1, MAGE-A4), BAGE family, GAGE family or NY-ESOT. Examples of tumor-specific antigens include CDK4 and β-catenin. Examples of SEREX antigens include D-1 and SSX-2.

In some embodiments, the first binding entity is an antibody that specifically binds to one or more of EpCAM (Trop-1), Tumor associated calcium signal transducer 2 (Trop-2), HER2, EGFR, MUC-1, c-Met, N-cadherin, Folate binding protein receptor (MOV18), Mesenchymal Stem Cell antigen (MSC, or W305) and CD318. In some embodiments a mixture of one or more, including 1, 2, 3, 4, 5, 6, 7 8, 9 or 10 of these antibodies can be employed as the first binding entity. In some embodiments a mixture of all of these antibodies can be employed as the first binding entity. In some embodiments, the target cells is a circulating tumor cell (CTC) as described herein.

In certain embodiments, the first binding entity is an antibody directed to mutated peptides that are activated as a result of cellular transformation. These peptides include but are not limited to mutated introns, N-acetylglucosaminyl-tranferase, V gene product, MUM-1 and p15.

In other embodiments, the first binding entity is an antibody that recognizes the ganglioside, GM2, GD2, GM3 and/or GD3; high molecular weight chondroitin sulfate proteoglycan, CD146, or p97 melanotransferrin. In other embodiments, the first binding entitiy is an antibody that recognizes Trop-1, Trop-2, or c-Met. In other embodiments, the first binding entity is a lectin that recognizes cell surface carbohydrates.

In certain embodiments, the target cell is a circulating tumor cell (CTC). A CTC in the blood sample is a tumor cell is often defined by staining positive for CK and DAPI and is staining negative for CD45 ($CK^+$, $CD45^-$, DAPI), whereas lymphocytes are $CD45^+$. Detection of the CTCs in the blood circulation can aid disease management, including the ability to monitor treatment efficacy or failure. However, due to the limited number of available CTC-specific antibodies, CTCs have failed to be captured in about 40%-60% of patient blood samples. Accordingly, the present invention in some aspects provides a method for capturing and detecting these rare CTCs.

According to the present invention, CTCs can be $CK^+$ or $CK^-$ and can be captured and evaluated for biomarker, such as markers of malignancy, drug selectivity or drug sensitivity independent of CK expression, or alternatively, in conjunction with CK expression, using the methods described herein. In some embodiments, captured CTCs include populations of cells that are $CK^+/CD45^-$, $CK^-/CD45^-$, $CK^+/CD45^+$ and/or $CK^-/CD45^+$. In some embodiments, the captured CTC population includes cells that have undergone EMT (epithelial-mesenchymal transition or transformation), such as cells that have lost CK expression (are $CK^-$); cells that have gained mesenchymal markers, such as but not limited to vimentin and fibronectin or other mesenchymal markers and/or cells that have gained EMT markers, such as but not limited to Twist1, Akt2 and PI3Kalpha. In some embodiments, the captured CTCs are further evaluated for markers of malignancy, such as aneuploidy. Examples of aneuploidy include but are not limited to monosomy, trisomy and tetrasomy and other chromosomal abnormalities as described herein or known in the art. In some embodiments, the captured CTCs are further evaluated according to standard methods for the presence or absence of CK. In some embodiments, the captured CTCs are or comprise $CK^-$ cells. In some embodiments, the captured cells, including $CK^-$ cells, are further evaluated for aneuploidy, such as for example but not limited to monosomy, trisomy and tetrasomy. In some embodiments, the captured cells, including $CK^-$ cells, exhibit aneuploidy, such as for example but not limited to monosomy, trisomy and tetrasomy. In some embodiments, the captured cells, including $CK^-$ cells, further evaluated for gene amplification, gene mutation, gene duplication and other nucleic acid or protein changes well known in the art. In some embodiments, the captured cells, including $CK^-$ cells, exhibit aneuploidy, are evaluated for markers drug selectivity and/or drug sensitivity by method well known in the art.

In some embodiments, the first binding entity is a mixture (e.g., cocktail) of at least a first antibody and a second antibody, wherein the first antibody specifically binds to a first epitope of the target entity and the second antibody specifically binds to a second epitope of the target entity. The first and second epitopes can be present on the same antigen (molecule) or the first and second epitopes can be present on different antigens (molecules).

In one embodiment, the first binding entity can be a mixture of a first antibody and a second antibody, wherein the first antibody specifically binds to a stem cell antigen and the second antibody specifically binds to a cancer cell antigen. Stem cell antigens can be present on cancer stem cells, and antibodies directed to these stem cell antigens can be added as general capture antibodies to one or more antibodies directed to cancer antigens, such as those described herein. In some embodiments, the first antibody specifically binds to CD133, CD135, CD117, CD34 or combinations thereof, and the second antibody specifically binds to a cancer antigen.

In another embodiment, the first binding entity can be a mixture of a first antibody and a second antibody, wherein the first antibody specifically binds to a mesenchymal marker and the second antibody specifically binds to a cancer cell antigen. Circulating tumor cells can downregulate epithelial markers and upregulate mesenchymal markers, and thus can be captured by antibodies that specifically bind to such mesenchymal markers. In some embodiments, the first antibody specifically binds to FGFR1 (fibroblast growth factor receptor 1), FGFR4, MSC (mesenchymal stem cell antigen), EGFR, N-cadherin, folate binding receptor or combinations thereof, and the second antibody specifically binds to a cancer antigen.

In still another embodiment, the first binding entity can be a mixture of a first antibody and a second antibody, wherein the first antibody specifically binds to an angiogenesis marker and the second antibody specifically binds to a cancer cell antigen. In certain embodiments, the first antibody specifically binds to a VEGF receptor, and the second antibody specifically binds to a cancer antigen.

In another embodiment of the invention, the method further comprises contacting the pre-loading mixture with a third binding entity. The first binding entity may be a primary antibody, the third binding entity may be a secondary antibody conjugated to a detectable or capturable entity, and the secondary antibody specifically binds to the first binding entity. The second binding entity specifically binds to the third binding entity (e.g., via the capturable entity). In another embodiment, the method further comprises contacting the pre-loading mixture with a third binding entity, wherein the first binding entity is a primary antibody, the third binding entity is a biotinylated secondary antibody that specifically binds to the first binding entity, and wherein the second binding entity is an avidin molecule. The secondary antibody may be a whole or an intact antibody, or fragment thereof, such as Fab'2, Fab' or Fab, or any antibody derivatives. A derivatized antibody can be a fragment of the antibody, an antibody that has been conjugated to a fatty acid, carbohydrate, peptide, a chemical entity such as a fluorescein, streptavidin etc. A derivatized antibody can be an antibody where the amino acids have been modified to increase the avidity or affinity of the antibody to the target protein.

In some embodiments, the method further comprises cross-linking the target cell bound to the surface of the micro-channel. Several cross-linking agents can be employed to cross-link the bound target cells to the micro-channel, for example via, amino groups (amide, amine etc.), carbonyl groups, acyl groups, alkyl groups, aryl groups, sulfhydryl groups, and others that are well known to one skilled in the art. Examples of cross-linking agents include, but are not limited to, hydrophilic homobifunctional NHS crosslinking reagents (e.g. Bis(NHS)PEO-5 (bis N-succinimidyl-[pentaethylene glycol] ester) to crosslink primary amines, homobifunctional isothiocyanate derivatives of PEG or dextran polymers, glutaraldehyde, heterobifunctional crosslinkers containing NHS on one end and maleimide on the other end of the polymer; peroxide treated carbohydrate polymers to form reactive aldehyde polymers, and EDC (1-Ethyl-3-[3-dimethylaminopropyl]carbodiimide hydrochloride) to crosslink carboxyl groups to primary amines. The length of the cross-linkers may be varied by adding one or more polymeric units between the two reactive groups on either end of the linker. Suitable polymeric units include, but are not limited to polymeric ethylene glycol, carbon chains, polynucleotides, polypeptides, and polysaccharides.

The cross-linking reagent can be applied to the micro-channel following capture of the target cells. In some embodiments, a second cross-linking treatment is employed following labeling (e.g. fluorescent labeling) of the captured cells to cross-link the label to the captured cells. The concentration of the cross-linking agent and duration of treatment will depend on the type and reactivity of cross-linking reagent, type of target cell, binding entities employed to capture the cells, and expression level of surface antigen to which a binding entity binds. Suitable concentrations can be from about 0.01 mM to about 10 mM, more preferably from about 0.5 mM to about 5 mM, or most preferably about 1 mM. Duration of treatment with the cross-linking reagent can be from about 5 min to about 120 min, about 15 min to about 90 min, or about 30 min to about 60 min. Optimization of the concentration of cross-linking reagent and duration of treatment is within the skill of the ordinary artisan.

Detecting the presence of captured cells can be by one of several methods known to those skilled in the art. In one embodiment, captured cells can be visualized by photomicroscopy. In another embodiment, captured cells may be labeled with a fluorescent molecule or stained and visualized by fluorescent microscopy or by measuring a fluorescent signal. For instance, captured cells may be stained with the nuclear dye DAPI and subsequently visualized by fluorescence microscopy. In another embodiment, detecting the presence of the target cell is carried out by detecting the presence of the first binding entity. Detection of the first binding entity can include exposing the captured cells to a tagged molecule that recognizes and binds the first binding entity. For example, the tagged molecule may be an antibody labeled with a fluorescent tag or colored latex particle that binds to the first binding entity. In one embodiment, the first binding entity is a biotinylated antibody and the tagged molecule is fluorescently labeled avidin. In some embodiments, the tagged molecule may be the same type of molecule as the second binding entity. In embodiments where a third binding entity is present, the detection of the captured cells can comprise detecting the presence of the third binding entity. In such embodiments, the tagged molecule recognizes and binds to the third binding entity. For example, the first binding entity can be a mouse antibody, the third binding entity can be a biotinylated secondary antibody that binds to mouse antibodies (e.g. a goat derived anti-mouse antibody), and the tagged molecule can be either a fluorescently labeled avidin or a fluorescently labeled antibody that binds to the third binding entity (e.g. a rabbit derived anti-goat antibody).

In some embodiments, subsequent analysis of the captured cells may be desired. In one embodiment, captured cells can be released from the micro-channel and collected for further analysis. Several methods for releasing the captured cells are known in the art and can include mechanical means (e.g. high fluid flow), chemical means (e.g. change in pH), or use of enzymatic cleavage agents. For example, a reagent may be applied to the micro-channel to cleave the second binding entity or to cleave the bond between the second binding entity and the cells in order to release the target cells from the micro-channel. For instance, trypsin, proteinase K, collegenase, or a specifically focused enzyme may be used to degrade the second binding entity (e.g. antibodies, streptavidin) and/or the cell surface antigens. During such cleavage, the outlet from the micro-channel is connected to a reservoir or other collector, and the discharge stream carrying the released cells is collected for further analysis. Such further analysis may include, but is not limited to, detection of aneuploidy, gene amplification, detection of gene mutation, gene duplication and other nucleic acid or protein changes well known in the art. For example, a gene mutation can be a substitution, addition, deletion of one or more nucleotides in a gene sequence. In one embodiment, the nucleic acid, such as DNA or RNA, obtained from the released cells can be subjected to fluorescent in-situ hybridization (FISH), PCR analysis, RFLP (restriction fragment length polymorphism) analysis, DNA sequencing, etc. Aneuploidy can include but is not limited to monosomy or trisomy of, for example, chromosomes 1, 3, 4, 7, 8, 11, and/or 17 tetrasomy at chromosomes 17 and 20. In another embodiment, proteins or glycoproteins, including peptides and amino acids obtained from the released cells can be subjected to, for example but not limited to, amino acid or peptide analysis or sequencing, GC-MS and other techniques known to those skilled in the art of protein analyses. In yet another embodiment, the captured cell released from the micro-channel device can be analyzed morphologically by light microscopy, electron microscopy, scanning microscopy, immunocytochemistry staining (ICC) for internal cellular structures or surface proteins expression, etc.

In another embodiment, the captured cells may be further analyzed in situ. For example, the cells may be counted while attached, labeled with fluorescent markers, subject to in situ hybridization analysis, such as FISH. Because antibody-antigen bonds are not covalent, they can be dissociated under some circumstances. Therefore, in some embodiments, it is highly desirable to further stabilize the cells on the micro-channel by crosslinking the cells to the channel so that cells are not dislodged and lost during the various in situ labeling, heating, denaturing and washing steps. Cross-linking can be a particularly important consideration with cells that express a low level of the surface antigens targeted by the first binding entity since these cells can be more weakly attached to the second binding entity. Covalent crosslinking of the cells to the channel surface matrix can stabilize captured cells during post-capture analysis.

In another aspect, the invention provides a method of post-capture analysis of circulating cells. The circulating cells may be captured as described herein, including by the methods or devices of the invention. In some embodiments, the circulating cells are captured and evaluated without one or more enrichment and/or cell replicating or duplicating processes, e.g., via cell culture, etc. In this aspect, circulating cells are evaluated for malignancy independent of CK status or expression, e.g., without CK staining and/or any other evaluating assay. For example, in accordance with this aspect, captured cells are evaluated (as described herein) for aneuploidy. The aneuploidy may be with respect to, for example, chromosomes 1, 3, 4, 7, 8, 11, 17 and/or 20. In certain embodiments, the invention involves evaluating circulating cells for monosomy or trisomy 8, 11, and/or 17. In certain embodiments, the invention involves evaluating circulating cells for monosomy 8, 11, and/or 17. In certain embodiments, the invention involves evaluating circulating cells for monosomy or tetrasomy of chromosomes 17 or 20, such as for example but not limited to tretrasomy 20q12. Aneuploidy may be detected using any know method, such as FISH. Additionally markers of cancer or malignancy may be used (except cytokeratin expression), such as those described herein, including Her2 expression.

The present invention also provides methods for evaluating a cell population for the presence of target cells and/or one or more biomarkers, which can include condition or disease markers. According to the present invention, the presence of a condition or disease in a patient can be determined by evaluating a target entity for a biomarker, where in some embodiments, the presence of the biomarker together with the target entity is indicative of a condition or disease. In some embodiments, the presence of the target entity can be used as a predictor of a disease and/or condition, such as for example cancer or malignancy. In some embodiments, the presence of the target entity is indicative of progression of the condition or disease (for example, progression of cancer to a malignant phenotype, development of drug selectivity and/or development of drug sensitivity). In some embodiments, diseases can include cancer and/or malignancy. In some embodiments, conditions can include drug selectivity and/or drug sensitivity. In some embodiments, the target entity can undergo further analysis for determining the presence of a biomarker indicative of a condition and/or disease. In some embodiments, the presence of a biomarker can be used to further characterize a condition or disease (for example, determining cancer type, cancer stage, drug selectivity and/or drug sensitivity). In some embodiments, the presence of a biomarker can be used to select or tailor a treatment regimen (for example, stopping a certain treatment, changing to a different treatment, etc.). The biomarker can include but is not limited to aneuploidy, gene amplification, gene mutation, gene duplication and other nucleic acid or protein changes as described herein or which are well known in the art.

A large variety of conditions and disease are known in the art in which rare cells have been implicated and any such conditions or disease are contemplated by the methods of the present invention. Such conditions and diseases can include but are not limited to cancer, malignancy (malignant phenotypes), cancer stages, drug selectivity, drug sensitivity and/or pregnancy (including for example, analyses of fetal cells in a sample from a pregnant individual).

As described by the methods of the present invention, the target entity can include rare cells, also referred to as target cells. Rare cells can include any cells that are not normally present in a biological sample and may be present as an indicator of a disease or condition. In some embodiments, these cells are present at about one or more order of magnitude less than other cells in the sample. Such diseases or conditions can include chronic diseases (such as cancer or a disease caused by a chromosomal abnormality), injury or pregnancy. In some embodiments, rare cells can include cells normally present in biological specimens, but that are present with a frequency that is about one or more orders of magnitude less than other cells present in a sample. Rare cells can include but are not limited to circulating tumor cells (CTCs), fetal cells, stem cells and other circulating cells. Generally, the target entity is defined by one or more capturable cellular targets, as described in detail herein.

Capturing rare cells that are CK⁻ and/or CK+ can also be useful for detecting cancer or malignancy in a patient. In some embodiments, rare cells are evaluated for malignancy independent of CK status or expression, e.g., without CK staining. In some embodiments, independent of CK status or expression (e.g., in the absence of detection of CK), the rare cells are further evaluated for aneuploidy, gene amplification, gene mutation, gene duplication and other nucleic acid or protein changes as described herein, or others which are well known in the art or are later described. In some embodiments, rare cells can be defined as cells captured by any of the first binding entities or combinations of the first binding entities that are described herein or other combinations of first binding entities (e.g., antibodies) that one of skill in the art would find useful for capturing a particular rare cell. In some embodiments, rare cells are circulating CD45⁻ cells captured by any of the first binding entities or combinations of the first binding entities that are described herein or other combinations of first binding entities (e.g., antibodies) that one of skill in the art would find useful for capturing a particular rare cell. In some embodiments, the total number of rare cells detected is important for detecting cancer, staging cancer or evaluating cancer disease progression, for example increased total numbers of rare cells may be indicative of malignancy or aggressive cancer or advanced disease progression (e.g., late stage cancer). In some embodiments, an increase or decrease in the ratio of CK⁻ cells detected to total rare cells detected is useful for detecting cancer, staging cancer or evaluating cancer disease progression. In some embodiments, an increase or decrease can be as compared to a predetermined standard number of rare cells. In some embodiments, the predetermined standard number of rare cells is zero (e.g., no detection of rare cells). In some embodiments, an increase or decrease can also be as compared to a sample from a patient without a disease (e.g., without cancer) or to a sample taken from a patient prior to onset of a disease (e.g., cancer). In some embodiments, an increase or decrease can be as compared between samples taken a various timepoints throughout progression of the disease (e.g., cancer).

According the present invention, the level of labeling of captured target cells can also provide useful information. Captured target cells can be further analyzed by detecting the presence or level on the captured target cells of the target entity to which the first binding entity binds and/or determining the presence or level of CK. Detection can be by any standard methods using any detectable label described herein or known in the art. In some embodiments, detecting the first binding entity is indicative of the presence of a target entity to which the first binding entity binds. In some embodiments, the level of detection of the first binding entity is indicative of the level of the target entity in the captured target. In some embodiments, the level of CK is indicative of the amount of CK in the captured target. In some embodiments, the level of CK in the captured target can be compared to the level of the target entity in the captured target in order to obtain a ratio of CK to target entity in the captured target. In some embodiments, the level of the target entity in the captured target can be compared to the level of CK in the captured target in order to obtain a ratio of target entity to CK in the captured target. In some embodiments, the ratio can be used for detecting cancer, staging cancer or evaluating cancer disease progression. In some embodiments an increase or decrease in the ratio can be used for detecting cancer, staging cancer or evaluating cancer disease progression. In some embodiments, the ratio can be compared to a predetermined standard ratio. In some embodiments, an increase or decrease can also be as compared to a ratio obtained from a patient without a disease (e.g., without cancer) or to a ratio obtained from a sample taken from a patient prior to onset of a disease (e.g., cancer).

In some embodiments, an increase or decrease can be as compared between ratios from samples taken a various timepoints throughout progression of the disease (e.g., cancer).

The detectable label can be any detectable label known to one of skill in the art, including fluorophores, enzymes (such as but not limited to peroxidase or alkaline phosphatase), heavy medals (such as but not limited to gold or ferritin), radioactive labels or any other molecule that is known by one of skill in the art for use in detection of a target entity. Detectable entities can include those used in fluorescence detection assays, enzymatic detection assays, gold detection assays, radioactive labels such as radioactive phosphorous (such as $^{31}P$, $^{32}P$ or $^{33}P$), sulphur (such as $^{32}S$ or $^{35}S$), and digoxigenin.

Detecting and/or further analyzing rare cells can also find use in detecting fetal conditions or diseases. In some embodiments, rare cells can include fetal cells. In some embodiments, fetal cells may be evaluated for aneuploidy, gene amplification, detection of gene mutation, gene duplication and other nucleic acid or protein changes as described herein or which are well known in the art. One of skill in the art would know which analysis to perform based on the fetal condition or fetal disease for which detection is desired.

This invention is further illustrated by the following additional examples that should not be construed as limiting. The contents of all references, patents and published patent applications cited throughout this application, as well as the Figures, are incorporated herein by reference in their entirety.

EXAMPLES

Example 1. Construction of Basic Micro-Channel Device

One embodiment of a micro-channel device for separating biomolecules or cells is shown in FIG. 1. The device comprises a substrate or support 11 which is formed with a flow path that includes a micro-channel 13 to which sample liquid is to be supplied through an opening or well 15 that serves as an entrance or inlet at a first end of the device and an opening 19 that serves as an outlet at the second end of the device. The cross-section of the collection region 17 is greater than that of an inlet section 18 that leads there into from the inlet opening 15. The inlet section contains one or more pairs of axially aligned divider/supports 21 just upstream of where it widens at the end of the region 18 to enter the collection region 17. These central dividers break the flow into two or more paths and serve to distribute the flow of liquid more evenly as it is delivered to the entrance end of the collection region 17. The collection region contains a plurality of upstanding posts 23 that are aligned transverse to the liquid flow path and arranged in an irregular, generally random pattern across the entire width of the collection region portion of the flow channel. The pattern of the posts is such that there can be no straight-line flow through the collection region and that streamlined flow streams are disrupted, assuring there is good contact between the liquid being caused to flow along the flow path and the surfaces of the posts. The posts are integral with the flat base of the collection region 17 and extend perpendicular from the base, presenting surfaces that are vertical relative to a horizontal path of the liquid being caused to flow through the flow channel of the substrate 11. Another flow divider/support 21a is located at the exit from the collection region.

The substrate is formed from PDMS and is bonded to a flat glass plate to close the flow channel. The interior surfaces throughout the collection region are derivatized with amine groups (Inventors: Is the amine group specific to PDMS or can there be other active groups, e.g. SH—that can be derivatized. I seem to remember one can coat supports with polylysine to attach cells or positively charged proteins) by incubating for 30 minutes at room temperature with a 3% solution of 3-aminopropyltriethoxysilane. After washing with ethanol the amine groups on the channel are derivatized for 30 minutes with bifunctional PEG linker molecule containing an NHS ester on one end and a maleimide group on the other end. In this reaction the NHS group reacts with the amine groups on the channel. After washing the channel with PBS a solution of 0.5 mg/mL thiolated streptavidin is added which will react with the maleimide groups on the other end of PEG linkers attached to the channel. Thiolated streptavidin is prepared by treatment of streptavidin with Traut's reagent as is commonly known in the art. After incubation for 60 min, the excess thiolated streptavidin is washed from the micro-channel with PBS/1% BSA and stored for future use.

In a typical example, 10 mLs of blood is obtained and the buffy coat is isolated by density gradient sedimentation as is commonly known in the art. The buffy coat contains the nucleated white blood cell fraction of the blood and also contains epithelial or other nucleated cells present in the blood. The buffy coat contained in a volume of approximately 0.5 mL in a centrifuge tube is incubated with the first binding entity of the present invention for 30 min, and then the tube is filled with approximately 30-fold excess of PBS/BSA and centrifuged to pellet the buffy coat cells. The sample is resuspended in approximately 200 μL and passed through the avidin-coated micro-channel by hooking the micro-channel device up to outlet tubing from a syringe pump which is filled with about 50 μL of the cell suspension. The syringe pump is operated to produce a slow continuous flow of the sample liquid through the micro-channel device at room temperature and a rate of about 10 μL/min. During this period, the avidin attached to the surfaces in the collection region where the random pattern of transverse posts are located, captures the target cells of interest in the sample. After the entire sample has been delivered by the syringe pump, a slow flushing is carried out with a PBS/1% BSA aqueous buffer. About 100 μL of this aqueous buffer is fed through the device over a period of about 10 minutes, which effectively removes all non-specifically bound biomaterial from the flow channel in the device. Two additional washings are then carried out, each with about 100 μL of PBS/1% BSA over a period of about 10 minutes.

At this time, inasmuch as the device is made of optically clear material, microscopic examination can be made of the effects of the capture using photomicroscopy. Captured cells may be treated further with additional antibodies and fluorescent probes and analyzed by fluorescence microscopy.

Figure 2:
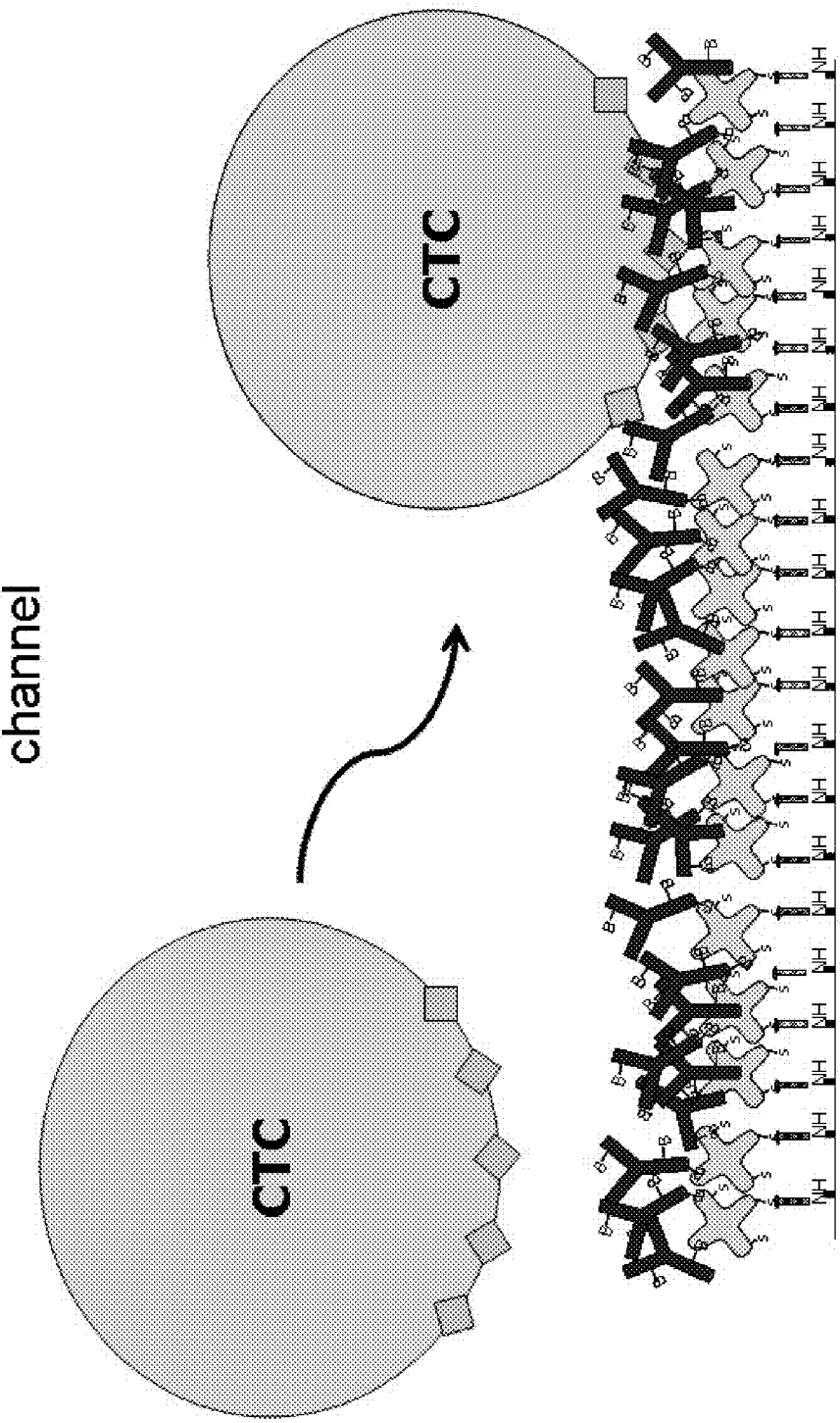
FIG. 2 is a schematic depicting capture of a circulating tumor cell (CTC) in a micro-channel device that has been coated with an antibody specific to an antigen on the CTC. B designates biotin.

Example 2. Comparison of Cell Capture Rates Between Pre-Labeled Micro-Channels and Pre-Labeled Cells As described in U.S. Published Application No. 2006/0160243, filed Jan. 18, 2005 and elsewhere (Nagrath et al. (2007) Nature, Vol. 450(7173):1235-9), previous devices for capturing cells of interest comprised a micro-channel that was derivatized with an antibody that was specific to antigens on the cells of interest. The suspension containing the rare cells of interest was then passed through the channel and cells were captured by the cell-specific antibody (FIG. 2).

While the level of antigen expression can be determined in cultured cells and on clinical tissue samples such as tumors, it is not known precisely how many antigens are available on the surface of a circulating tumor cell (CTC). It is known that tumors are highly heterogeneous and that cells detached from the tumor into the blood can change their expression levels of antigen. Therefore, it is most likely that CTCs are a highly heterogeneous population with specific antigen levels varying from very low to very high in any given sample. To obtain maximum capture of CTCs from a sample, it is best to optimize the system to capture cells with the lowest antigen expression levels.

Figure 3:
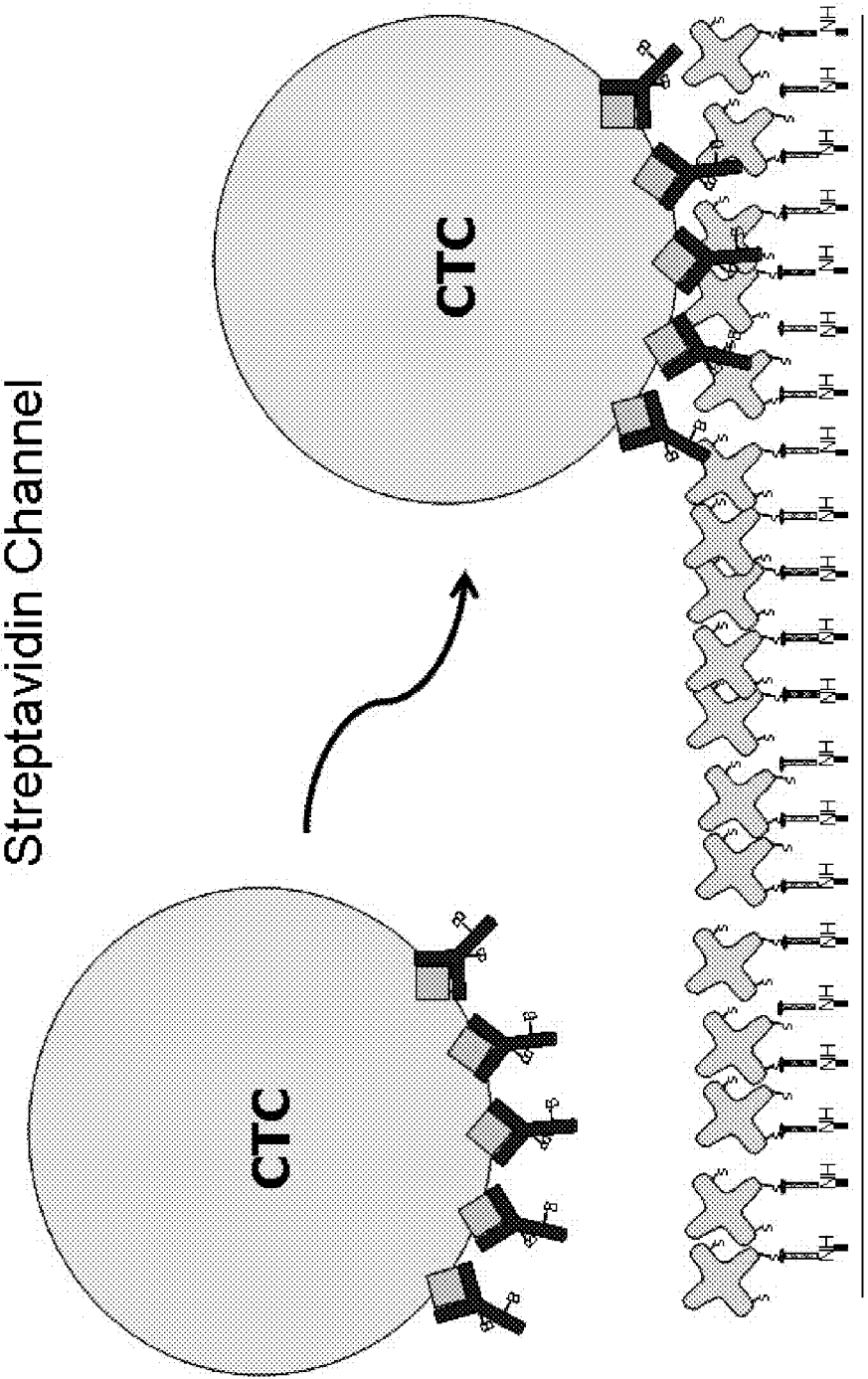
FIG. 3 is a schematic depicting capture of a circulating tumor cell (CTC) in a micro-channel device where the CTC has been pre-labeled with an antibody specific to a CTC antigen and the micro-channel device has been coated with a protein capable of binding the cell-specific antibody. B designated biotin.

The devices of the present invention comprise a micro-channel derivatized with a general antibody or protein that can bind to cell-specific antibodies as described in Example 1. The cell-specific antibody is added to the sample containing the cells of interest prior to passing the sample through the micro-channel, thus pre-labeling the cells. The cells of interest are then captured when the general antibody or other protein coating the channel binds to the cell-specific antibody bound to the cells of interest (FIG. 3).

The following set of experiments were conducted to determine whether pre-labeling a sample containing CTCs with antigen-specific antibodies result in a better capture rate on micro-channel devices as compared to micro-channel devices coated with the antigen-specific antibody. A common antigen used to capture CTCs is EpCAM, an epithelial cell surface adhesion molecule. For these experiments, the bladder cell line, T24, was used, which is known to express low levels of EpCAM.

In the traditional device, the micro-channel was derivatized with streptavidin and then biotinylated antibody for EpCAM was pre-loaded onto the channel (EpCAM channel). The EpCAM antibody was able to bind the EpCAM antigen on the surface of the T24 cells, thus capturing the cells in the micro-channel. In the device of the present invention, the micro-channel was derivatized with streptavidin (Strep channel) and the biotinylated antibody for EpCAM was incubated with the sample of T24 cells at approximately 1 µg/mL for 30-60 mins. prior to passage of the cells over the streptavidin-coated channel. The streptavidin binds to the biotinylated EpCAM antibody bound to the surface of T24 cells, thus capturing the cells in the micro-channel. Thus the reagent components of the two devices are identical except that they are applied to the devices in a different order.

Figure 4:
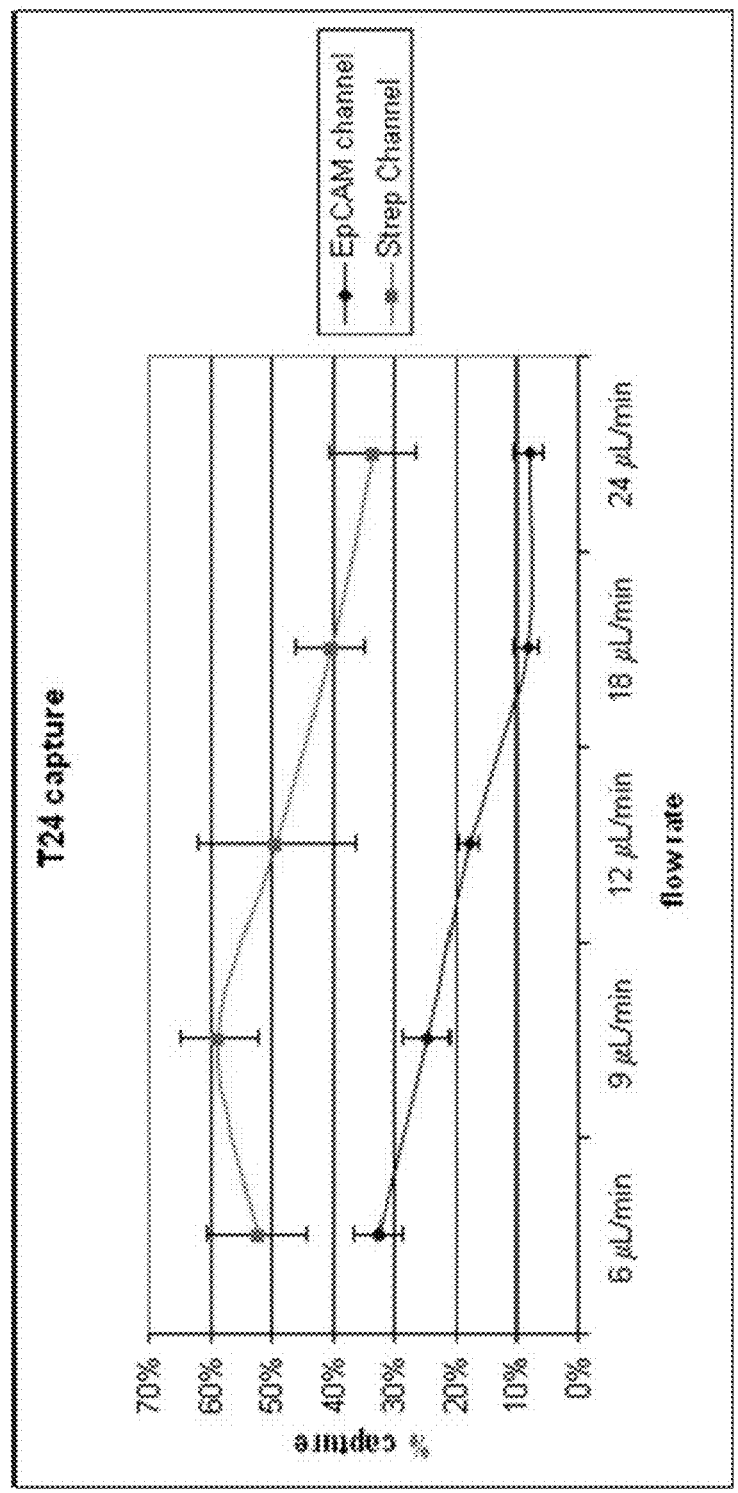
FIG. 4 is a graph showing percentage of T24 EpCAM positive cells captured on either a micro-channel coated with EpCAM antibodies (EpCAM channel) or a micro-channel coated with streptavidin (Strep channel) at different flow rates. In the case of the Strep channel, the T24 cells were pre-labeled with a biotinylated EpCAM antibody prior to passage over the Strep channel.

As shown in FIG. 4, use of the streptavidin-coated channel with cells pre-incubated with the biotinylated EpCAM antibody unexpectedly produced capture percentages about twice as high as those obtained with the EpCAM channel and unlabeled cells. The increased capture percentage is about 2-3 fold higher when cells are passed through the channel under multiple flow rates.

Figure 5:
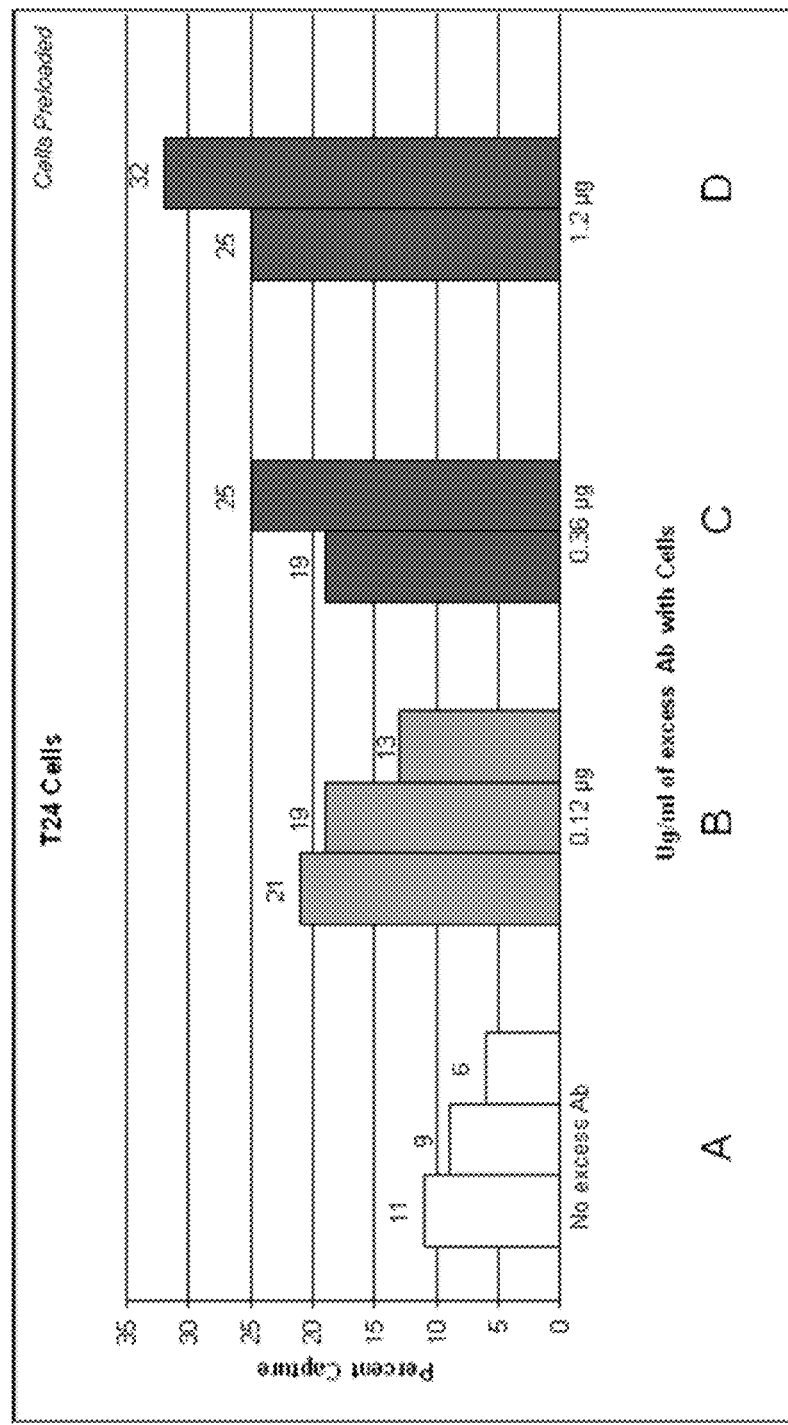
FIG. 5 is a graph showing the percentage of T24 cells pre-labeled with biotinylated EpCAM that were captured on a micro-channel coated with stretpavidin in the presence of different concentrations of excess biotinylated EpCAM antibody. A sample of 250 µL containing approximately 200 cells was applied to the channel.

In a next series of experiments, 1.2 µg/mL of the biotinylated-EpCAM antibody was pre-incubated with the cells for 30 mins. This concentration of antibody was about 100 to 1000 fold molar in excess over the total antigens present on the T24 cells and therefore, significant excess antibody remained in each suspension. After a 30 mins. incubation, the excess antibody was diluted to less than 0.05 µg/mL by dilution of the cells to approximately 200 cells for application on the channel. This sample of cells served as a control sample and was applied directly to the channel in 250 µL PBS/BSA (sample A in FIG. 5). In samples B-D excess antibody at the indicated concentrations were added back to the 250 µL cell suspension prior to running on the channel. As shown in FIG. 5, free antibody does not interfere with binding to the streptavidin on the channel, and does not decrease cell capture as expected, but in fact increases cell capture.

Figure 6:
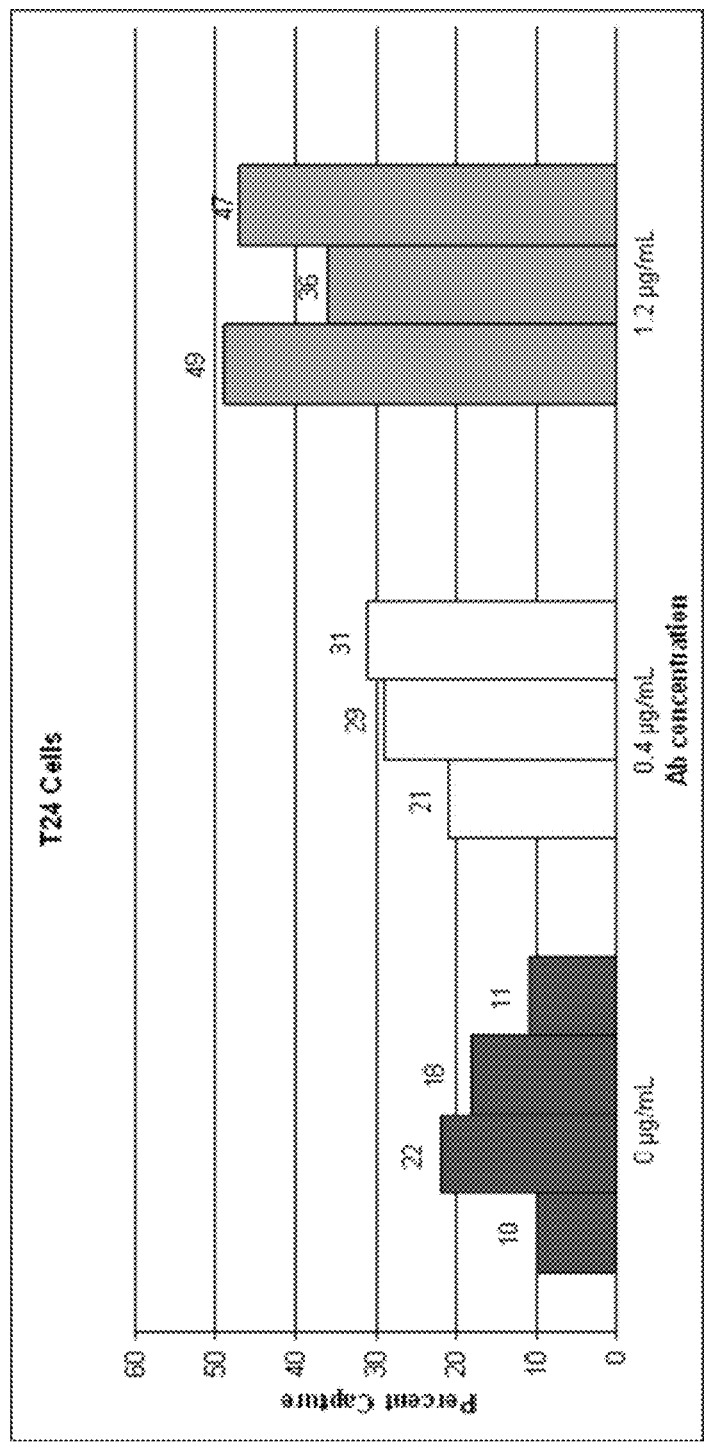
FIG. 6 is a graph showing the percentage of T24 cells pre-labeled with biotinylated EpCAM that were captured on a micro-channel coated with stretpavidin in the presence of different concentrations of excess biotinylated EpCAM antibody. A sample of 2 mL containing approximately 200 cells was applied to the channel.

In a similar experiment, the volume of the initial cell suspension applied to the channel was increased from 250 µl to 2 mL. Since the µg per mL of the added extra antibody remained the same as in FIG. 5, the total µg of absolute antibody in the sample with approximately 200 cells was nearly 10 times higher than in FIG. 5. As shown in FIG. 6, the added extra antibody shows a similar increase in cell recovery relative to the concentration of the antibody that was observed in the results depicted in FIG. 5. This result indicates that the observation of higher recovery is related to the concentration of excess antibody in the cell suspension and not the absolute µg of total antibody in the cell suspension.

The results of this series of experiments show unexpected advantages in collecting cells of interest in a micro-channel flow device when the cells are pre-labeled with antibody. As seen in FIG. 4, pre-incubating the cells with antigen-specific antibody significantly improves capture in the micro-channel device as compared to capture in micro-channels coated with the antigen-specific antibody. In addition, the presence of excess antibody in the cell sample during the run does not limit this methodology but can in fact mediate increased binding of the cellular antigens to the streptavidin matrix on the channel, thereby enhancing capture.

Example 3. Use of Multiple Antibodies Increases the Capture Rate of Target Cells It has traditionally been considered most efficient to pre-load an antibody onto the channel. However, the negative effects on cell capture of loading a channel with multiple antibodies have not been previously considered. An advantage of using a micro-channel coated with a general binding partner (e.g. antibody or protein) of an antigen-specific antibody is that multiple antibodies can be added to a cell suspension to pre-label cells without lessening the availability of any single antibody. Because multiple antigen sites on a cell are not mutually exclusive, when adding multiple antibodies to the cell suspension the capture efficiency on the channel is not diminished for any single antibody. By way of example, if the channel could accommodate 100 antibody sites and a mixture of 5 different antibodies were added to coat the channel, then each antibody would occupy ~20% of the channel space. Thus, the potential binding efficiency for each individual antibody is only 20% of what it would be if it covered the entire channel. Regardless of the number of antigens on the cell, the channel is inherently less efficient at capturing those cells with only 20% of that individual antibody. When the cell has a low number of target antigens, the efficacy in capturing these low antigen expressing cells can be amplified by the addition of the antibodies specific for other target antigen in the cell suspension prior to binding to the substrate or support of the micro-channel device. For example, if the same 5 antibodies are added to the cell suspension, then each antibody can maximally bind to all cognate cell surface antigens independently, without interference or reduction due to the presence of other antibodies bound to different epitopes on the cell. By derivatizing each of the five different antibodies with a common capture tag (e.g. biotin), a channel coated with a binding partner for the capture tag (e.g. streptavidin) can bind all 5 antibodies simultaneously to their respective antigens on the cell, thus producing an additive effect on cell capture.

Figure 7:
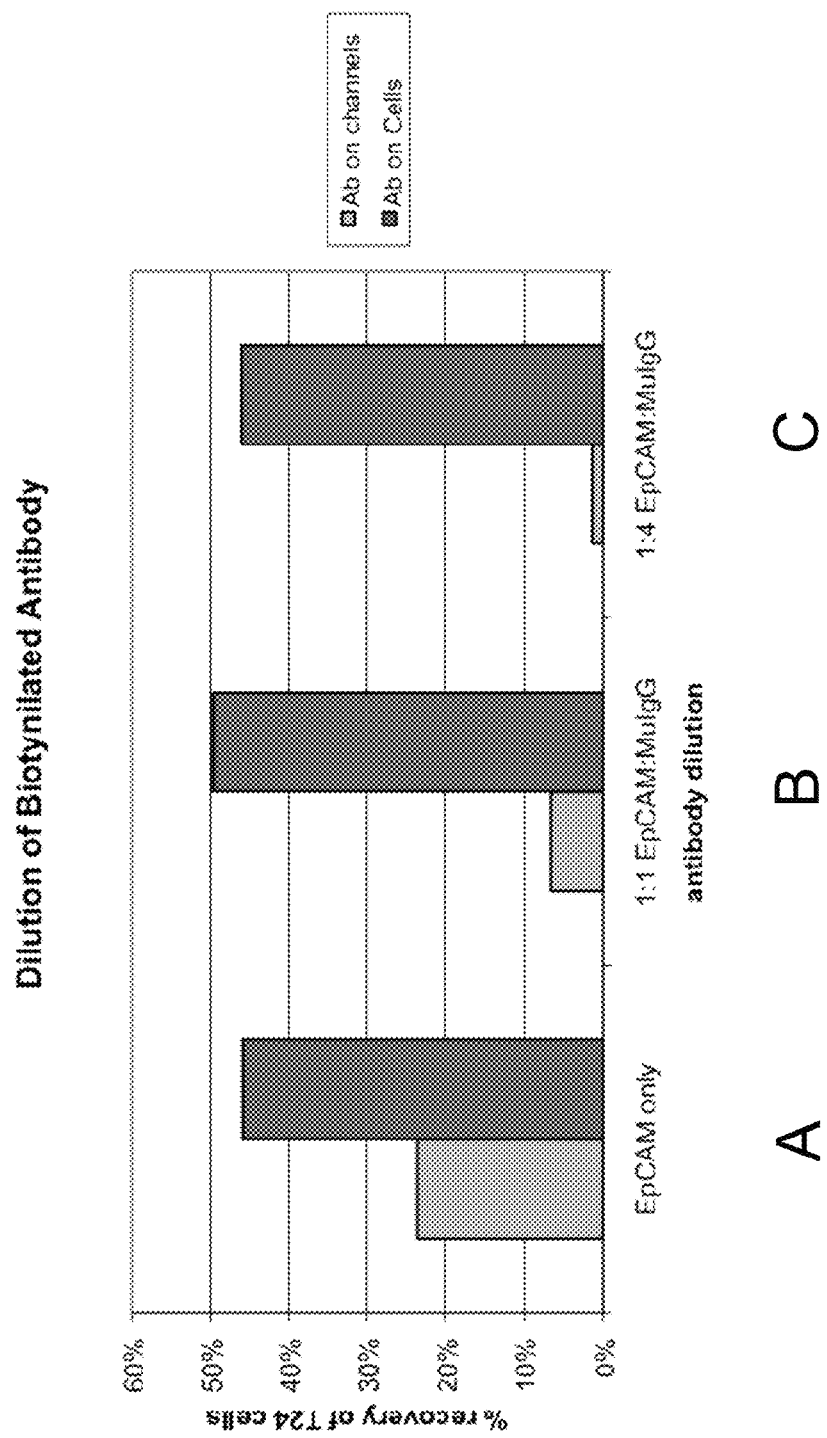
FIG. 7 is a graph showing the dilution of the EpCAM capture antibody that is coated onto the micro-channel compared to the capture of T24 cells as a function of the same dilution mixture used to pre-label cells prior to application onto the micro-channel.

FIG. 7 shows a reduction in the capture of T24 cells when the ratio of EpCAM antibody to murine IgG on the channel is lowered when the antibodies are first coated on the substrate/support of the micro-channel device. To determine the effect of EpCAM capture in the presence of additional biotinylated antibodies, the biotinylated EpCAM antibody was diluted with irrelevant biotinylated mouse IgG and the resulting mixture was used, either to coat the channel with antibody or added to the cell suspension prior to passage over the channel. FIG. 7 (sample A) shows that the percentage of T24 cell-capture is about twice as high when the cells were pre-labeled with biotinylated EpCAM antibody only. This observation is consistent with the results seen in FIG. 4. However, when the EpCAM antibody was diluted in a 1:1 ratio with an irrelevant antibody and used to either label the cells directly or to coat the channel, the channel recovery drops from 24% to 7%, while the recovery of pre-labeled cells is unaffected (FIG. 7, sample B). When the EpCAM was diluted in a 1:4, the recovery drops to 1% when the antibody mixture was first coated on the channel while the recovery is unchanged when the cells were pre-labeled with the antibody mixture prior to binding to the substrate or support of the microchannel device (FIG. 7, sample C). These results demonstrate that dilution of the EpCAM antibodies by additional antibodies do not interfere with the maximal binding of the EpCAM antibodies to the cells when the cells were prelabeled with the soluble antibodies, but that precoating of the channel with the diluted EpCAM antibodies shows a significant reduction in the capture of the low EpCAM expressing T24 cells. It is therefore evident that if the EpCAM antibody were mixed with 2 or 3 or 4 different antibodies for binding on the channel, even if the other antibodies were relevant to a surface antigen on the cell, the EpCAM antibody itself would be commensurately diminished in its binding effectiveness. Therefore, when adding multiple antibodies to the channel, the effect of each antibody cannot be expected to be additive. The overall effect on cell capture is unpredictable in this configuration since circulating tumor cell (CTC) antigen levels are variable. By definition the antibody in a mixture that might be directed towards the highest level antigen on the CTC will be diminished by the addition of antibodies to the lesser antigen levels on the CTC. If only one antibody in a mixture recognizes a dominant epitope on a particular CTC, then diluting with several other antibodies on the channel will adversely affect capture instead of enhancing it. By contrast, mixtures of soluble antibodies added to cells prior to passage over the channel are additive.

Figure 8:
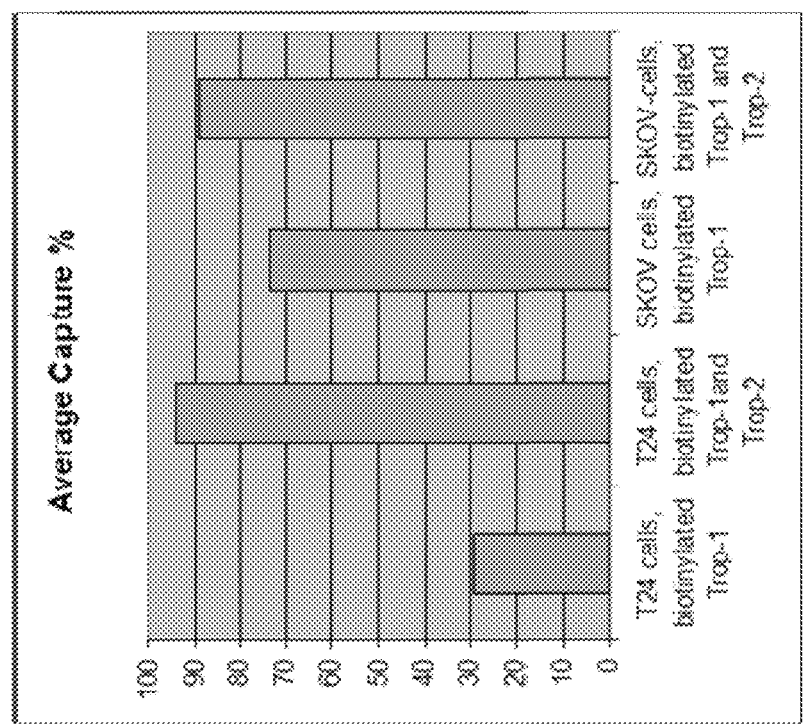
FIG. 8 is a graph depicting the percentage of T24 or SKOV cells captured on a streptavidin-coated micro-channel when pre-labeled with either biotinylated Trop-1 antibody alone or in combination with biotinylated Trop-2 antibody.

To demonstrate the additive effect of multiple antibodies on prelabeled cells prior to passage over the channel, two different antibodies to two different cell surface adhesion antigens, Trop-1 and Trop-2, were added to cell suspensions of either T24 bladder cells or SKOV ovarian cells. Each of the antibodies was biotinylated and cells were captured using a micro-channel device coated with streptavidin. When Trop-1 antibody was used to pre-load T24 cells, 29% of the cells are captured (FIG. 8). When Trop-2 antibody, which binds to a different antigen than Trop-1 antibody, was added in combination with the Trop-1 antibody, 94% of the cells are captured. A similar result is obtained with SKOV cells. A capture of 74% of the cells is observed with pre-labeling with Trop-1 antibody alone. However, a capture of 89% of the cells is observed when both Trop-1 and Trop-2 antibodies were added simultaneously (FIG. 8). The results show that addition of more than one antibody to more than one target site on the surface of the cell increases the effective number of channel-detectable molecules attached to the target cell and produces an additive effect on cell capture.

Figure 9:
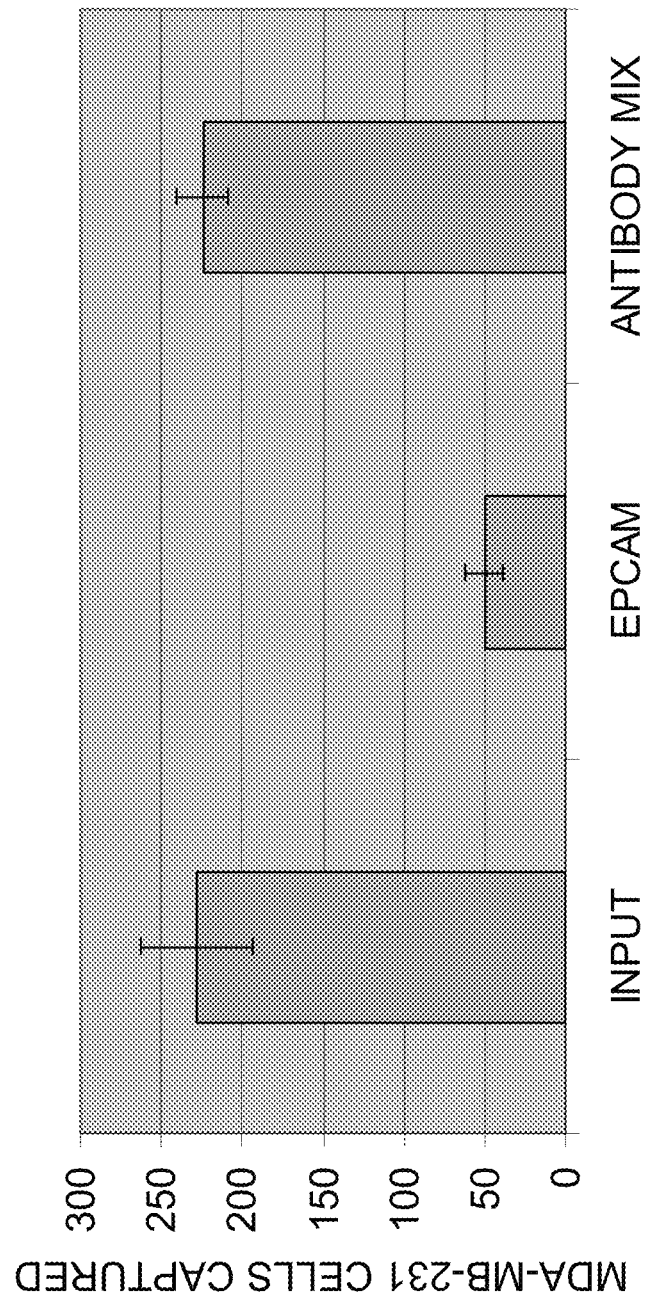
FIG. 9 is a graph depicting the capture of MDA-ND-231 cells on a streptavidin-coated micro-channel when pre-labeled with either biotinylated anti-EpCAM antibody alone or in combination with a mixture of biotinylated capture antibodies.

In FIG. 9 the same additive effect is observed using a different cell line and with a different antibody mixture. In this case the breast cancer cell line, MDA-MB-231, which has a low EpCAM expression was tested. In FIG. 9, the % capture with EpCAM antibody alone is low, but adding a mixture of 6 antibodies specific for the antigens: EpCAM, Trop-2, EGFR, MUC-1, CD318 and HER-2 improves capture to essentially 100%. FACS analysis of the MDA-MB-231 showed that this cell line has very low antigen expression of EpCAM, Trop-2, Her-2, and MUC-1 but higher expression of EGFR and CD318. Therefore, the antibodies to the higher expressing antigens were diluted 3-fold with antibodies to low expressing antigen. The diluted antibodies are still highly effective in capturing this low EpCAM-expressing cell line. This result is consistent with the results shown in FIG. 7 where antibodies were used to pre-label the cells.

Example 4. Secondary Antibody Labeling of Target Cells can Effect Capture in the Micro-Channel Device In some instances, a non-derivatized primary antibody may more efficiently bind to the antigen of interest or may be easier to employ. With some antibodies their activities are adversely affected by derivatization procedures which modify their surface amino acids. In cases, where one desires to use a non-derivatized primary antibody to bind to cellular antigens, a derivatized secondary antibody may be added to the cell suspension to form a complex with the primary antibody which is bound to the cellular target antigen. Thus, primary antibody mixtures, semi-purified or non-clonal hybridoma supernates can be added to the cell suspension and any antibodies that attach to antigens on the cell can be labeled by the addition of a derivatized (e.g. biotinylated) secondary antibody. Antibodies that do not bind to the cell are simply washed away.

To illustrate this approach, the cultured ovarian SKOV cell line was pre-labeled with either biotinylated Trop-1 antibody (Sample A in FIG. 10) or non-biotinylated Trop-1 plus a 3-fold molar excess of biotinylated anti-mouse secondary antibody. The primary antibody (Trop-1) concentration was 1 µg/mL and the cells were incubated for 30 mins. either with or without 3 µg/mL secondary antibody before cell capture and purification on a micro-channel device. The difference between samples B and D was that a longer biotin linker on the secondary antibody was used in sample D. In sample C, the cells were washed with PBS/BSA to remove excess primary and secondary antibody before applying the cells to the channel. In all samples, approximately 200 cells were suspended in 250 µL of PBS/BSA for application to the channel.

Figure 10:
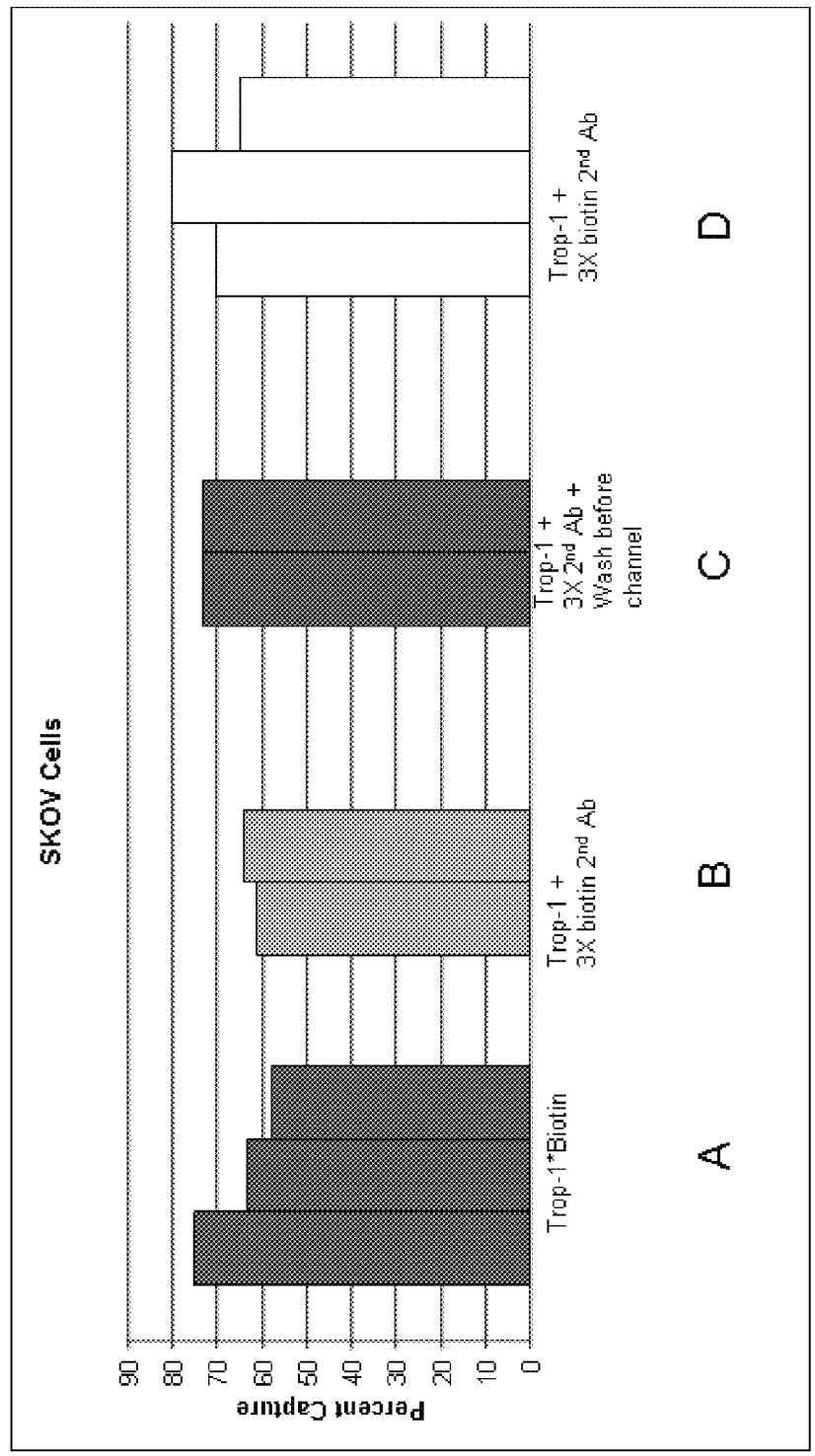
FIG. 10 is a graph depicting the percentage of captured SKOV cells on a streptavidin-coated micro-channel when pre-labeled with biotinylated primary antibody or a combination of non-biotinylated primary antibody and biotinylated secondary antibody.

As shown in FIG. 10, all samples have similar recovery. These results demonstrate that biotinylated secondary antibody can be used in combination with unlabeled primary antibody to pre-labeled cells for effective capture in a micro-channel device. The presence of some excess biotinylated secondary antibody did not adversely affect the capture percentage compared to direct pre-labeling with 1 µg of biotinylated Trop-1. Secondary antibodies may include intact IgG antibody, or antibody fragments such as Fab'2, Fab', Fab or engineered antibody fragments such as single chain Fab or single chain variable fragment.

Example 5. Stabilization of Captured Cells on Channel Surface

The process of capturing cells on a micro-channel device involves flow of cells suspended in a liquid. Therefore, the cells are subjected to sheer forces from the liquid flow that can also dislodge the cells from the channel after they are captured. This effect is more pronounced with cells that have lower surface antigen levels because there are relatively fewer attachment points between the cell and the specific cell surface antigens bound to the channel surface by the antibody. Therefore, it is advantageous to provide an additional external attachment of the cell to the channel surface by means of cross-linking reagents to better stabilize the attachment of the cell to the channel. Since the channel is typically coated with a binding protein (e.g. streptavidin or an antibody), a facile means of further anchoring the cell to the channel is through protein cross-linking reagents.

Reagents known in the art for this purpose can be homobifunctional NHS esters to crosslink amino groups on proteins. Another way of cross-linking is through the thiol or disulfide groups on the proteins with thiol reactive reagents, such as heterobifunctional molecules with a maleimide and an NHS ester. In addition, reagents such as EDC can be used to cross-link carboxyl and amino groups. The length of these cross-linkers can be varied by the use of polymeric regions between the two reactive groups, which typically take the form of chemical linkers such as polymeric ethylene glycol or simple carbon chains, but can also include sugars, amino acids or peptides, or oligonucleotides. Polymer chain lengths of from 5 to 50 nm are typical for this purpose but can be shorter or longer as needed. The common property of all of these protein cross-linking reagents is to covalently bind cellular proteins so as to anchor the cell to the surface of the channel by multiple covalent attachment points.

To examine whether externally added cross-linking reagents enhance retention of the captured cells on the coated micro-channels, cells were captured on coated micro-channels and subjected to high flow rates in the absence or presence of a protein cross-linker. Streptavidin-coated surfaces of micro-channels were prepared. The cultured T24 cell line, which is known to have a low expression level of surface EpCAM, was used as a model cell line. One µg/mL biotinylated anti-EpCAM antibody was incubated with the cells for 30 mins. at 4° C. and approximately 325 cells were suspended in 250 µL of PBS/BSA buffer and passed in triplicates over coated micro-channels at 12 µL/min. The exact number of cells applied to the channel was determined microscopically by counting the cells in duplicate aliquots. After the cell suspension was passed through the channel, the channel containing bound cells was washed once with PBS/BSA and then a solution of homobifunctional NHS ester (bis N-succinimidyl-[pentaethylene glycol] ester) at 2 mM was passed over the channel and allowed to incubate for 20 mins. The control channel without NHS ester received only PBS/BSA solution. The cells were then washed with a 5% PEG solution in PBS for 2 mins. at various flow rates. The 5% PEG/PBS solution increases the solution viscosity and along with higher flow, provides more sheer force on the cells for purposes of this comparison. The cells captured in the channel were then stained with the nuclear staining dye, DAPI and counted.

Figure 11:
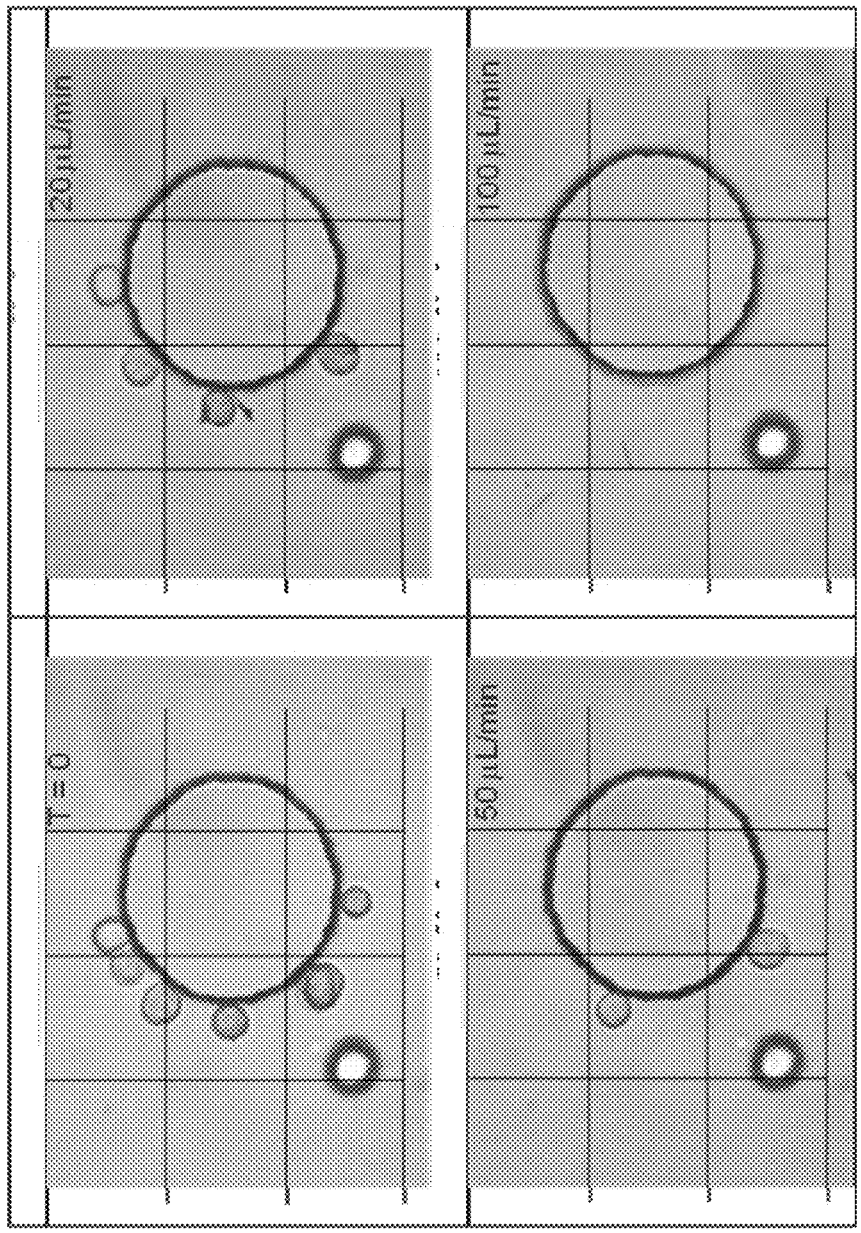
FIG. 11 shows a series of photomicrographs of cells captured in a coated micro-channel that were subsequently subjected to washes with a viscous solution at different flow rates (20, 50, and 100 µL/min).

FIG. 11 shows photomicrographs of captured cells subjected to different flow rates in the absence of protein cross-linker. Almost 50% of the cells are lost at a flow rate of 20 µL/min and all of the cells are lost at a flow rate of 100 µL/min.

Figure 12:
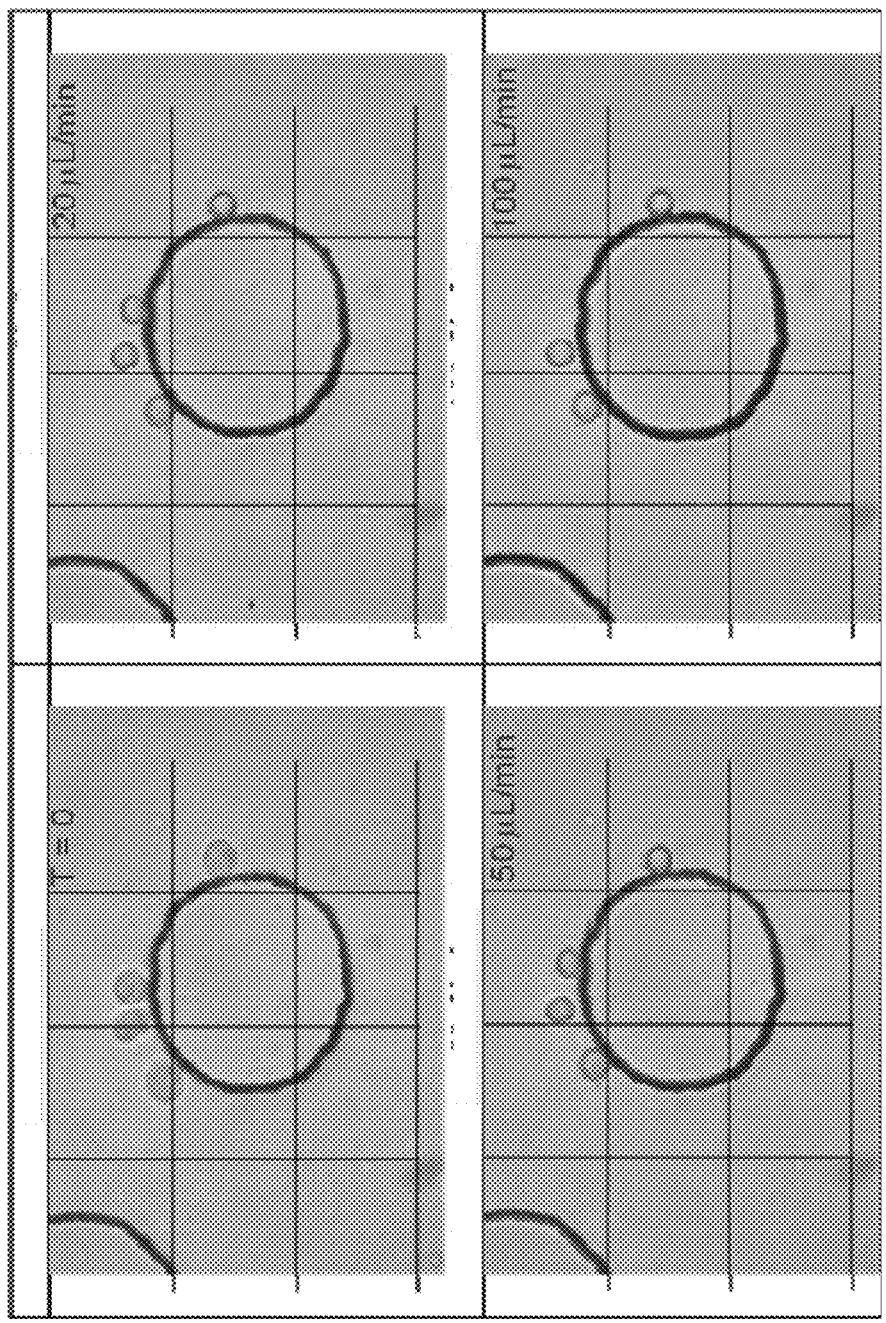
FIG. 12 shows a series of photomicrographs of cells captured in a coated micro-channel. The cells were exposed to a homobifunctional NHS protein cross-linking reagent prior to being subjected to washes with a viscous solution at different flow rates (20, 50, and 100 µL/min).

FIG. 12 shows photomicrographs of captured cells subjected to different flow rates after exposure to a NHS protein cross-linker. All cells are retained on the channel at flow rates of up to 50 µL/min and only one cell was lost at a flow rate of 100 µL/min.

Figure 13:
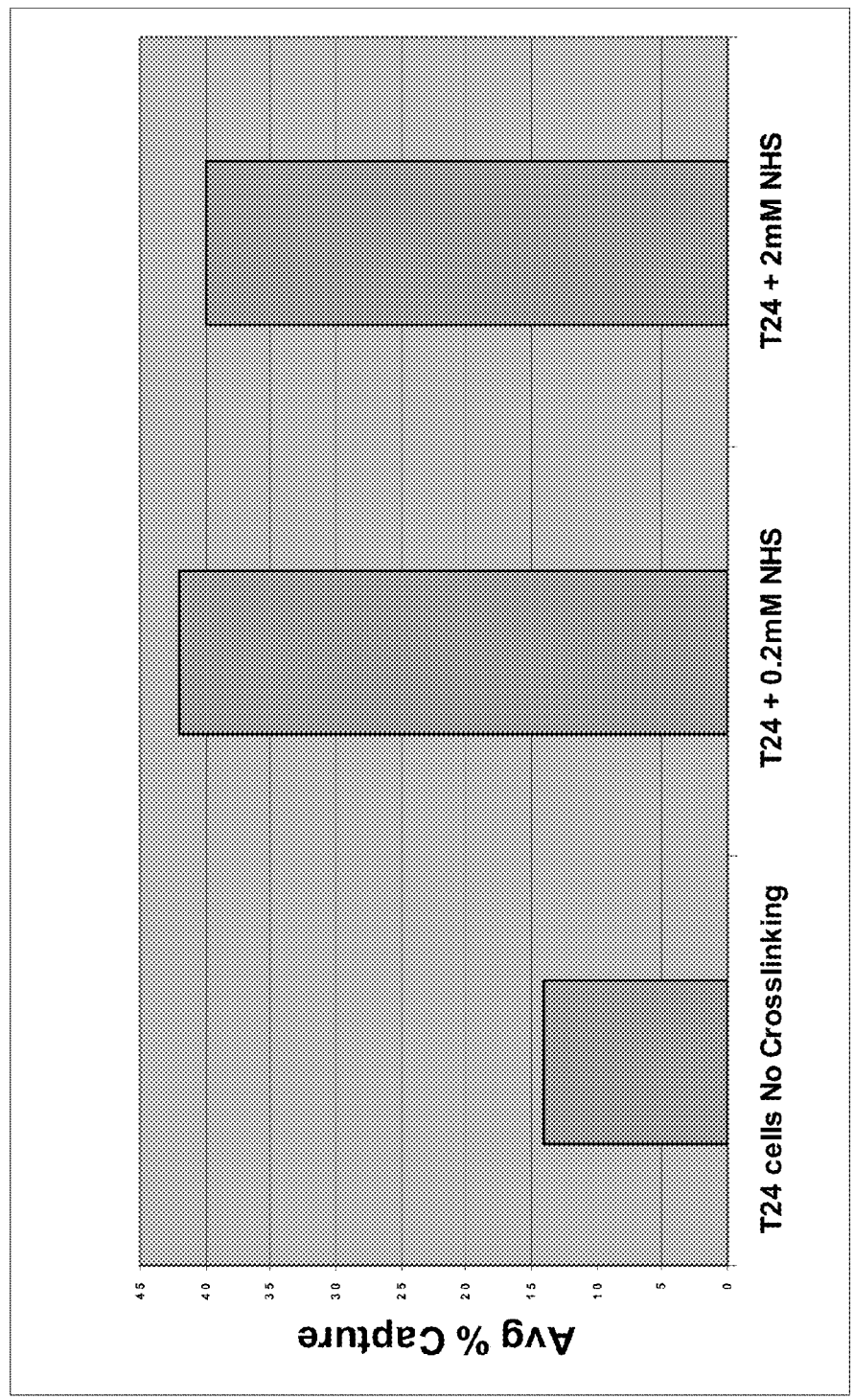
FIG. 13 is a graph showing the percentage of captured cells on a coated micro-channel in the absence or presence of a NHS protein cross-linking reagent.

A quantitative comparison of capture with and without cellular stabilization by protein cross-linking is shown in FIG. 13. As in previous experiments, approximately 200 T24 cells were applied to the micro-channel and after capture, the cells were washed with 5% PEG in PBS. FIG. 13 shows that less than 50% of the cells which not treated with crosslinking reagent are recovered compared to the percentage of cells recovered in channels treated with a crosslinker. Thus, the addition of protein cross-linking reagents significantly stabilizes cell attachment to the micro-channel. It should be noted that this result is independent of how the cells were captured on the micro-channel, whether by pre-loading antibody on the cells or on the channel, since the crosslinking agent stabilizes the cell on the micro-channel after the cells have been captured.

A second experiment similar to the above was employed to test for cell stability on the channel. After treatment of the cells with the protein crosslinker as above, the SKOV cells on the channel were subsequently stained with anti-cytokeratin (to visualize epithelial cells) and DAPI (to visualize cells with a nucleus). The difference in this experiment was that the tubing connected to the outlet was disconnected, a process that can cause transient but abrupt pressure pulses that can sheer and dislodge cells from the micro channel.

Table 1 shows the increasing numbers of cells lost when cells were not crosslinked to the channel were subjected to exogenous mechanical forces as a result of removing the outlet tubing. If cells were fixed to the channel with methanol treatment prior to removal of the tubing connections, there is no significant difference in cell recovery regardless of whether crosslinker was used (data not shown). However, methanol fixation (or any alcohol or acetone fixation) has several undesirable side-effects for the purposes of some subsequent cell analyses. Cells fixed with methanol are permeabilized due to disruption of the cell membrane and therefore cell surface studies cannot be distinguished from internal cell reactions. In addition, cells fixed with methanol become fused to the channel matrix making cell removal difficult and inefficient. Such cells can be subjected to extensive proteolysis to aid in cell removal, but cellular digestion has several undesirable side-effects for some types of subsequent cellular analysis. The procedure of crosslinking cells to the channel allows stabilized cells on the channel to be retained without alcohol fixation during normal channel operations and manipulations including higher flow rates, higher viscosity buffers and removal of channel connections.

TABLE 1

| Conditions | 2 mM Crosslinker + methanol | 2 mM Crosslinker No methanol | 0.2 mM Crosslinker No methanol | 0.07 mM Crosslinker No methanol |
| --- | --- | --- | --- | --- |
| % retained on channel | 100% (control) | 96% | 60% | 28% |

Example 6. Antibody Mixtures (Antibody Cocktail) Enhances Capture of Epithelial-Like and Mesenchymal-Like Cancer Cells Urothelial carcinoma (UC) cell lines have lower expression of EpCAM in more invasive tumor models. Such cells in circulation would be expected to limit the utility of EpCAM-based CTC capture. A cohort of 5 UC cell lines (UMUC3, UMUC5, UMUC9, T24, and KU7) were selected based on gene expression heat map analysis as being either more epithelial or more mesenchymal-like. In the latter case, these cells have undergone the epithelial to mesenchymal transition (EMT) which results in epithelial cells with mesenchymal expression and morphological characteristics. This EMT has been proposed as a mechanism by which epithelial cells can dissociate from the tumor and become more migratory and invasive in circulation.

These EMT cells were further tested by FACS for a variety of cell surface antigens. After identifying expression differences in these cell lines, an antibody mixture of EpCAM and 5 additional antibodies was selected to improve cell capture of all UC cell types. We subsequently compared cell capture rates using microfluidic channels with the antibody mixture compared to EpCAM alone. Cells were also immunostained with cytokeratin and vimentin antibodies to help further distinguish cells having epithelial or mesenchymal-like expression characteristics, respectively.

Figure 14:
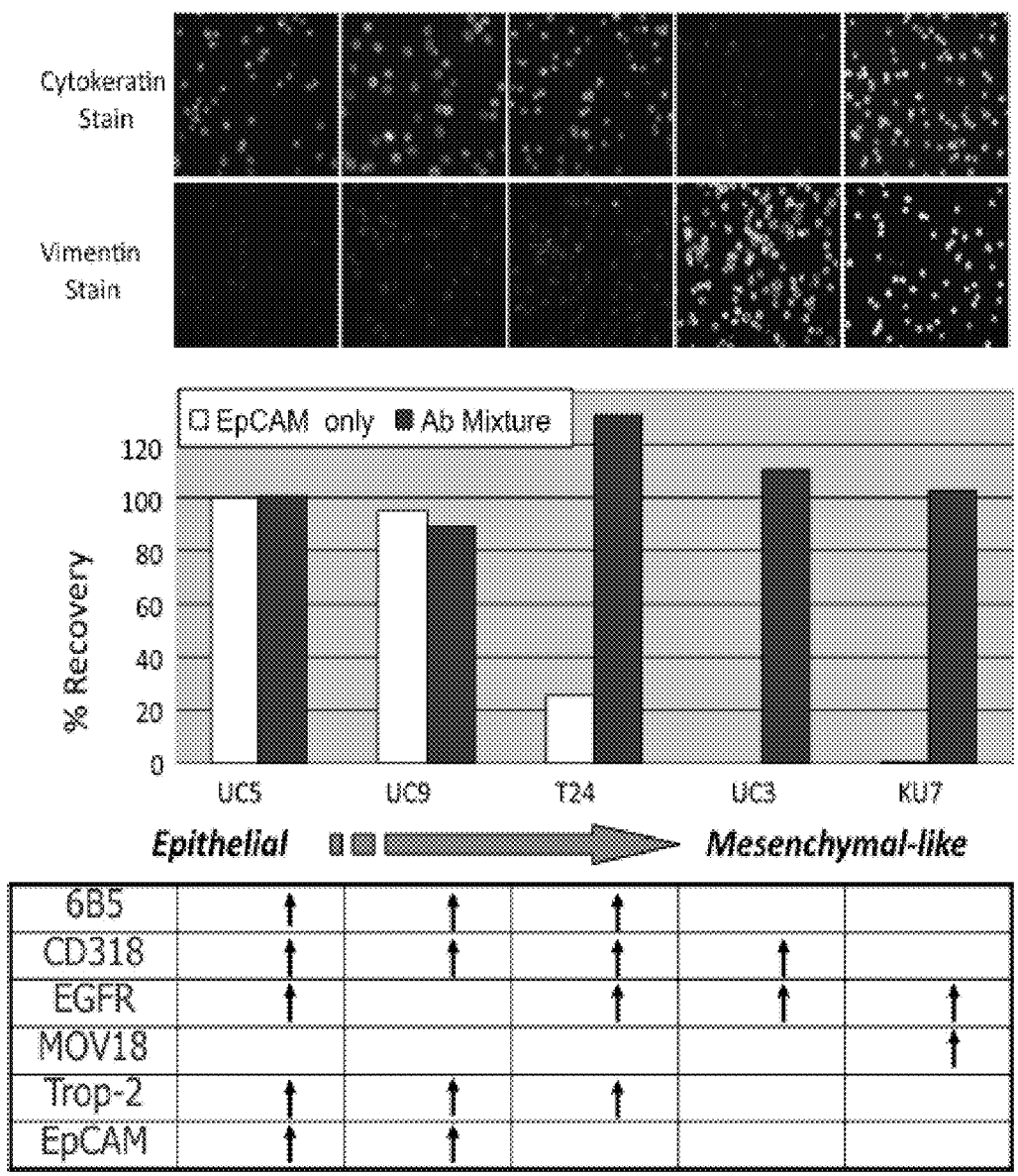
FIG. 14 is a graph showing the percentage of captured bladder cancer cells on a coated micro-channel when using EpCAM only as the capture antibody compared to using a mixture of antibodies. The graph also shows the staining of the cell types with anti-cytokeratin and anti-vimentin antibodies.

FIG. 14 shows the staining of the 5 UC cells lines with vimentin and cytokeration. Among the 5 UC cell lines, 2 (UC3 and KU7) stained with vimentin and had minimal to no expression of EpCAM. While these cells lines retained some degree of cytokeratin staining, one cell line stained only with vimentin (FIG. 14). The remaining 3 lines (UC5, UC9 and T24) stained only for cytokeratin and had significant EpCAM expression. Those cell lines with no EpCAM expression (UC3 and KU7) had no cell recovery when EpCAM alone was utilized as the capture antibody. However, when the antibody mixture, comprising 6b5, CD318, EGFR, MOV18, Trop-2 and EpCam) was used, all 5-cell lines achieved nearly 100% cell capture rates. In the case of KU7, the most mesenchymal-like of this group of cell types, the folate binding receptor (MOV18) was unique and not expressed in the other cell lines.

The results show that the use of a mixture of antibodies allows capture of both bladder epithelial cells and bladder epithelial cells that had undergone EMT. The study shows that the use of antibody mixtures provides a dramatic improvement over cell recovery compared to the use of a single antibody alone, such as EpCAM alone. Because of the heterogeneity of tumor cell types expected in circulation, such an approach is expected to significantly improve the capture and isolation of CTCs from patient samples.

Example 7. Capture of Low-Antigen Expressing Cells on a Micro-Channel Device Increases with Antibody Mixture or Cocktails Common detection methods are needed when cocktails of antibodies are used to simultaneously bind to several different cancer cell types. While cytokeratin stain works well for epithelial cells, some epithelial cells have lost cytokeratin expression as described in Example 6. With other cells types, such as stem cells, there is no specific method for staining these cells that does not have significant crossreactivity to other blood cell types which may be non-specifically bound to the channel. However, high levels of biotinylated primary or secondary antibodies on the surface of the cells are common to all cells captured specifically by the avidin on the microchannel. The benefit of using cocktails of biotin-conjugated antibodies is the additive effect in increasing surface biotins on target cells, which is useful for increasing the capture of low antigen-expressing cells or cells expressing variable levels of one or more antigens in a heterogenous cell population, such as those found in tumor patients. See FIGS. 8, 9, and 13.

Figure 15A:
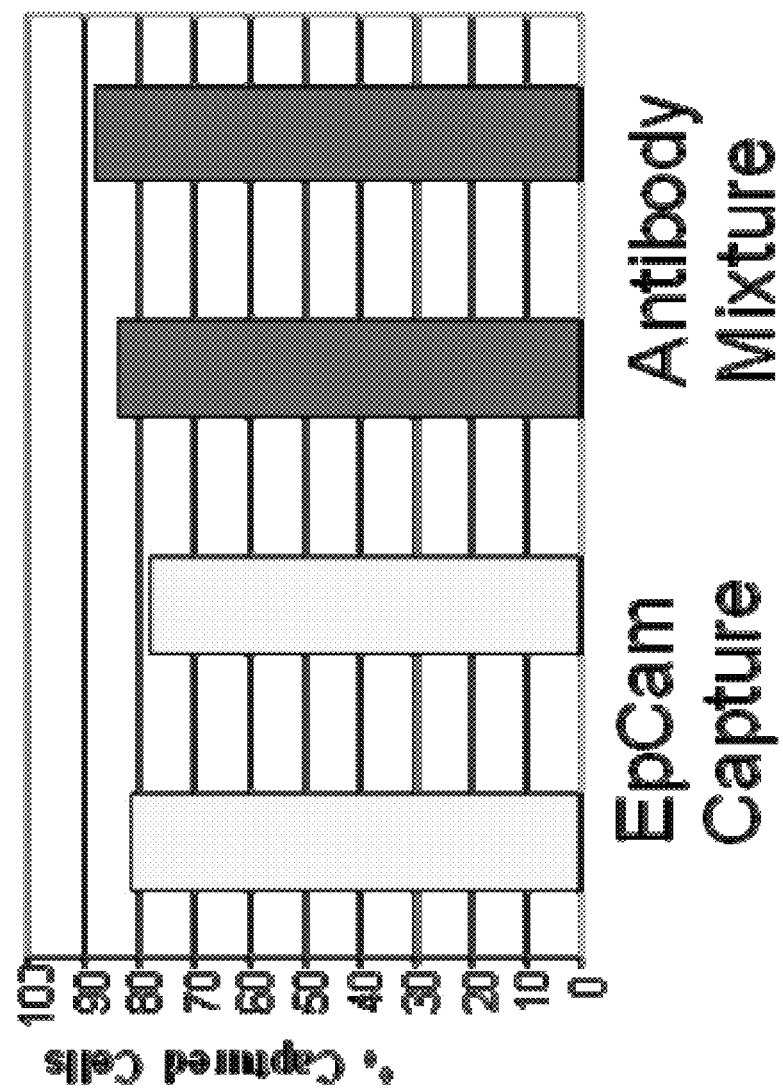
FIG. 15A is a graph showing the capture of SKOV cells by EpCAM antibody compared to capture by an antibody mixture.
Figure 15B:
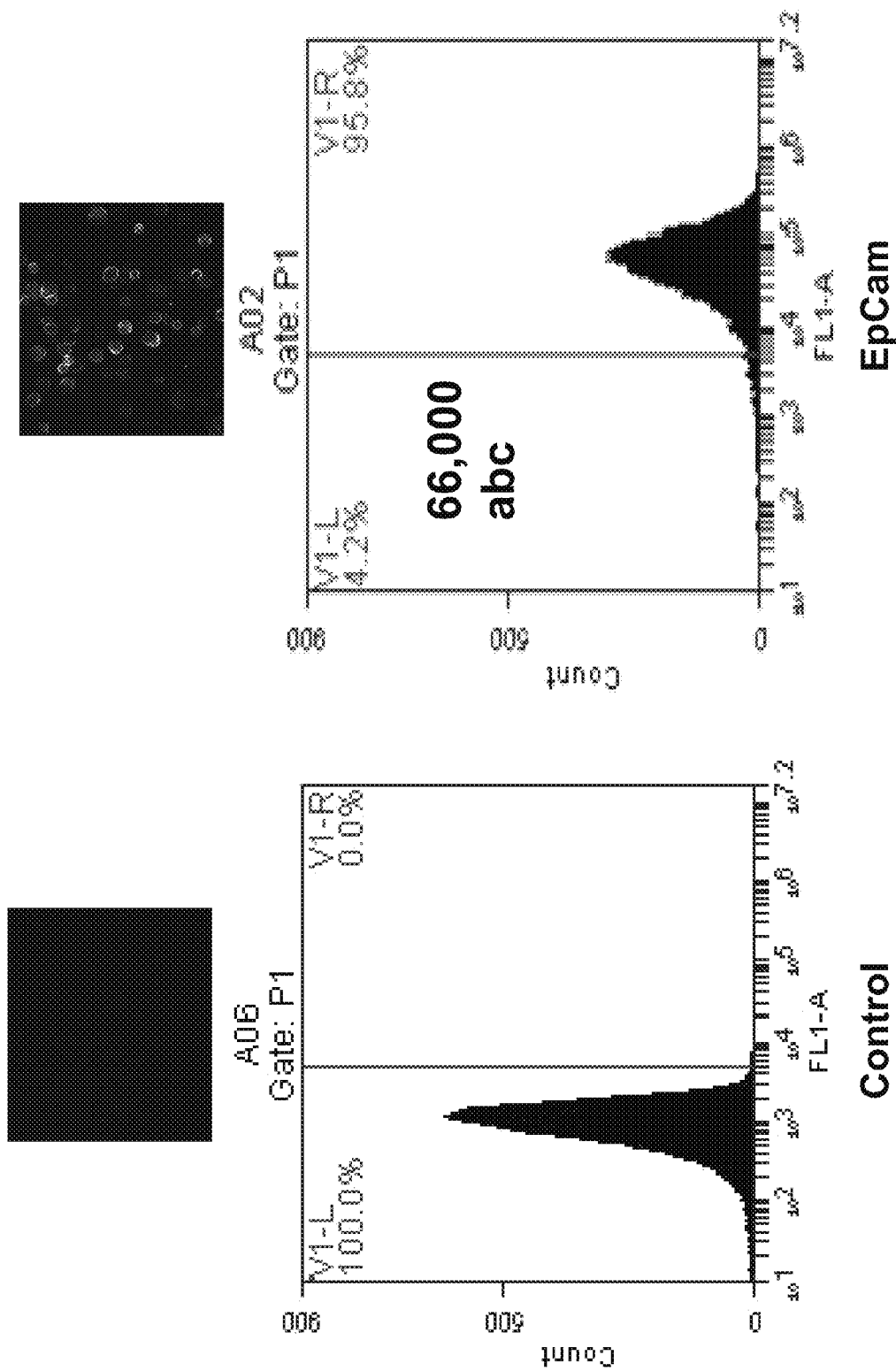
FIG. 15B shows the staining of SKOV cells after incubation with EpCAM antibody or antibody mixture and detected with fluorescently labeled secondary anti-mouse antibody. FACS analysis of the same cells shows the number of surface antigens labeled with labeled secondary anti-mouse antibody.
Figure 15B:
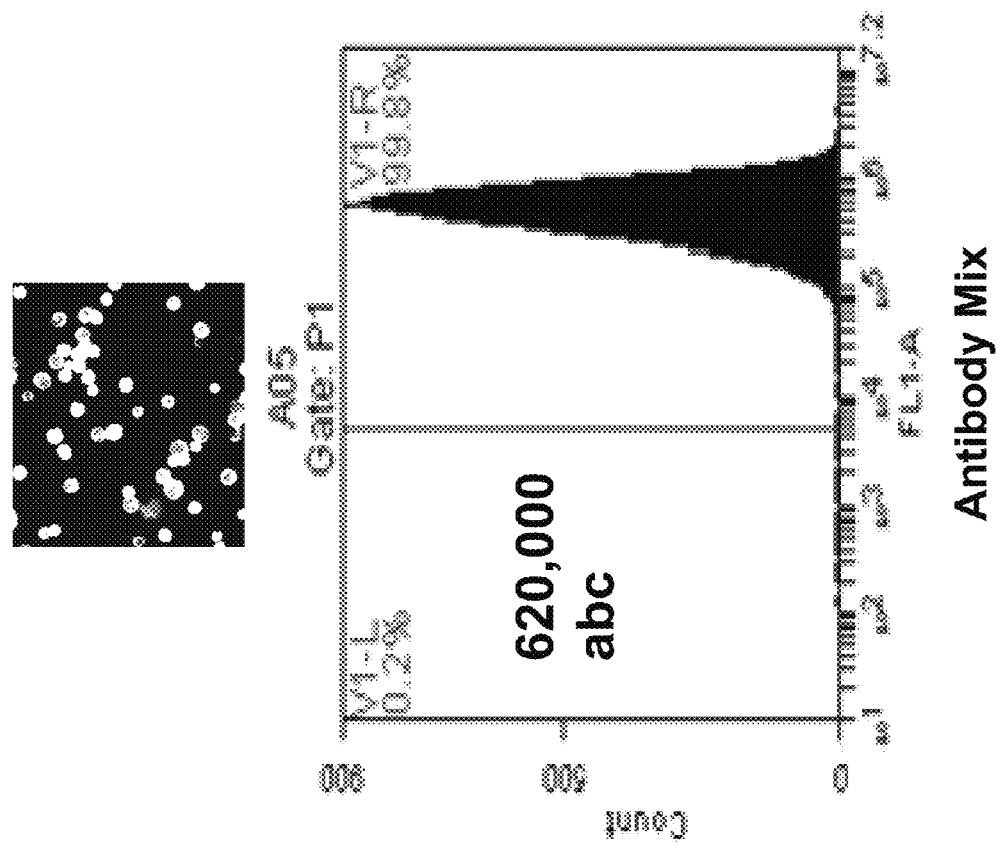

The unexpected additional advantage of using multiple antibodies in a cocktail is that this provides a common detection method for a heterogenous population of cells that have variable level of antigen expression An example of this is shown in FIG. 15.

FIG. 15A shows the percentage capture of SKOV cells, which is known to express a high level of EpCam antigen (approximately 40-70,000 EpCam antigens per cell (apc)), with EpCam alone or with a mixture of antibodies specific for other surface antigens expressed by the cells, including EpCAM, Trop-2, EGFR, MUC-1, CD318 and HER-2. The results show that there is no significant improvement in the percent number of SKOV cells captured with EpCam antibody alone or a mixture of antibodies specific for other antigens in addition to EpCam.

In contrast, FIG. 15B shows the fluorescence staining intensity of the same SKOV cells by FACS and on slides. These cells stain with very different intensities depending on whether they have been pre-mixed with EpCam alone (~66,000 surface antigens) or with an antibody mixture which are directed against Her-2, CD24, CD44, combined surface antigen level of ~600,000 antigens as determined by the FACS analysis. Fluorescently labeled anti-mouse antibody was used to label the primary antibodies. While there was minimal increase in the capture of these antibody cocktail-incubated SKOV cells using biotinylated secondary antibody as shown in FIG. 15A, using fluorescently labeled secondary antibody in FIG. 15B shows that the staining intensity is significantly higher when using the antibody mixture. In a similar manner, this differential would be obtained if cells were reacted with primary antibody, followed by biotinylated secondary antibody and fluorescently labeled biotin-reactive avidin. Thus there is an significant advantage in using antibody cocktail mixtures even when additional antibodies are not necessary for capture of the cells. In the case of a low EpCam-expressing cells, the capture using EpCam antibody alone is reduced (FIGS. 4-6, 14), but is significantly increased when using an antibody cocktail. In this case the staining intensity based on the number of antibodies bound to the surface of the cells would also be increased. Therefore the use of fluorescently-labeled molecules that target the multiple antibodies used to better capture the cells has the universal advantage of better detection of those same cells. The use of antibody cocktails has the unique advantage in allowing detection of cells for which there may not be a known specific marker for detection such as cytokeratin in epithelial cells, or where the cytokeratin has been lost as shown in FIG. 14. The multiple antibodies used in a mixture for better capture of cells with variable expression of surface markers can still be targeted for fluorescence labeling based solely on their increased levels of bound antibodies from the antibody cocktail.

Figure 16:
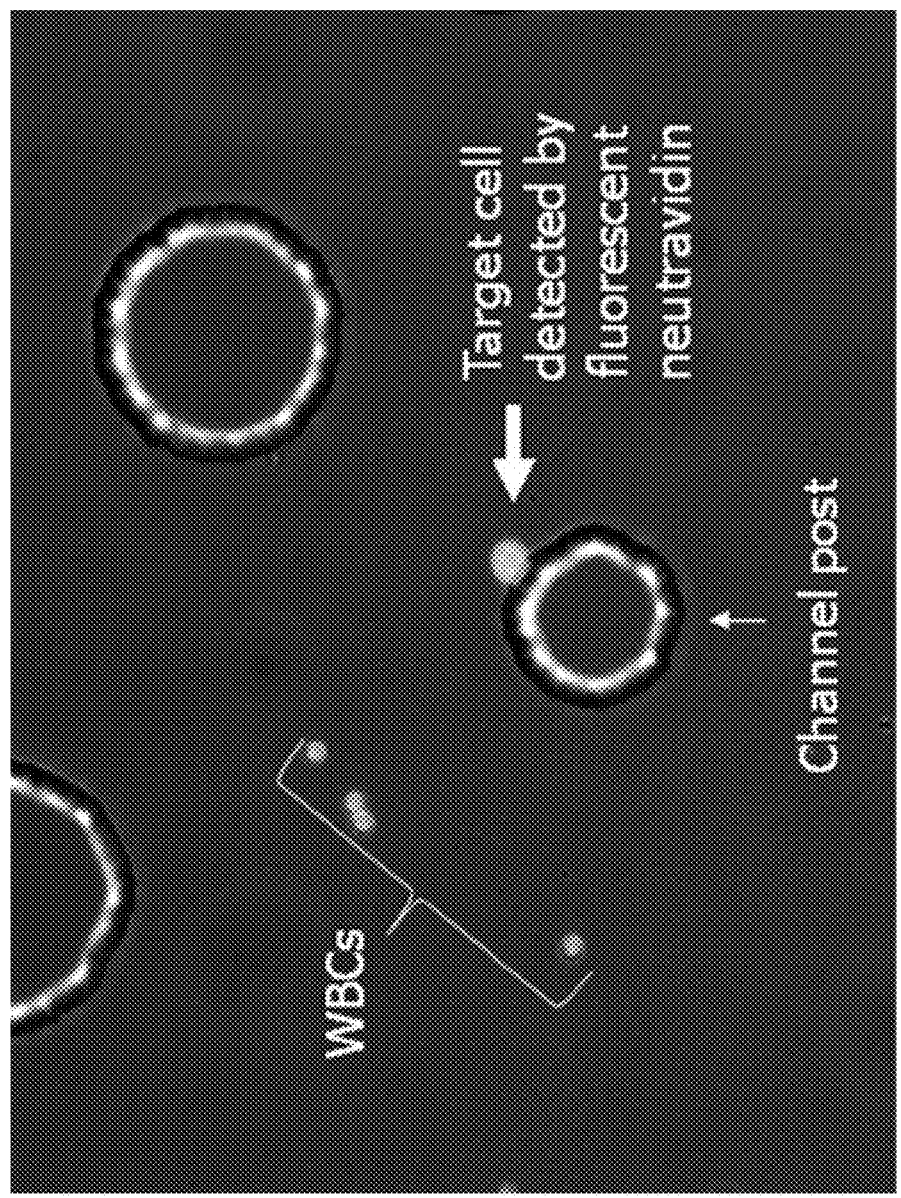
FIG. 16 is an image of SKOV cells spiked into blood and captured on a microchannel using a primary antibody mixture and biotinylated secondary anti-mouse antibody. Cells were stained on the channel with fluorescently labeled neutravidin which tightly binds biotin. Image shows SKOV cell stained green with NeutrAvidin and nearby white blood cells that did not stain with neutravidin but stained only with DAPI to detect the nucleus.

FIG. 16 shows the additive effect of multiple antibodies in a cocktail, which contain antibodies specific for the SKOV target cells and which are shown to associate minimally to the non-specific cells present in a blood sample, when the blood sample was spiked with SKOV target cells. The antibody cocktail contained antibodies directed against CD340, EGFR, CD318, Muc-1, Trop-2, EpCam, Mov-18, MSC, c-met and N-Cadherin. Although some of the non-specific cells in the sample may have adsorbed some of the biotinylated antibodies (either primary or secondary) added to the samples, the level of antibodies adsorbed is far too low to be visualized using fluorescently-labeled neutravidin. The differential staining between specific target cells and non-specific cells favors the visualization of the target cells which have higher numbers of biotinylated antibodies from the antibody mixture bound or captured by the target cells. FIGS. 15 and 16 demonstrate that addition of multiple antibodies in a cocktail provides a common and universal method of detecting rare cell types that express low levels of antigens on the microchannel. Thus, the antibody cocktail used to enhance and thereby increase capture of circulating tumor cells that are highly variable in heterogenous cell population in a sample, also enhance detection of any of the captured cells.

Example 8. The Micro-Channel Device is Superior at Capturing Cells from Biological Samples that are Present in Low Cell Numbers In FIG. 17, blood samples were spiked with a variable number of SKBr3 cells, a cell line expressing high levels of EpCAM, ranging from about 10-250 cells per 10 mL blood sample. EpCAM antibodies were added to the spiked blood sample and the EpCAM Ab-bound cells were captured on a micro-channel device using the method described in Example 1.

Figure 17:
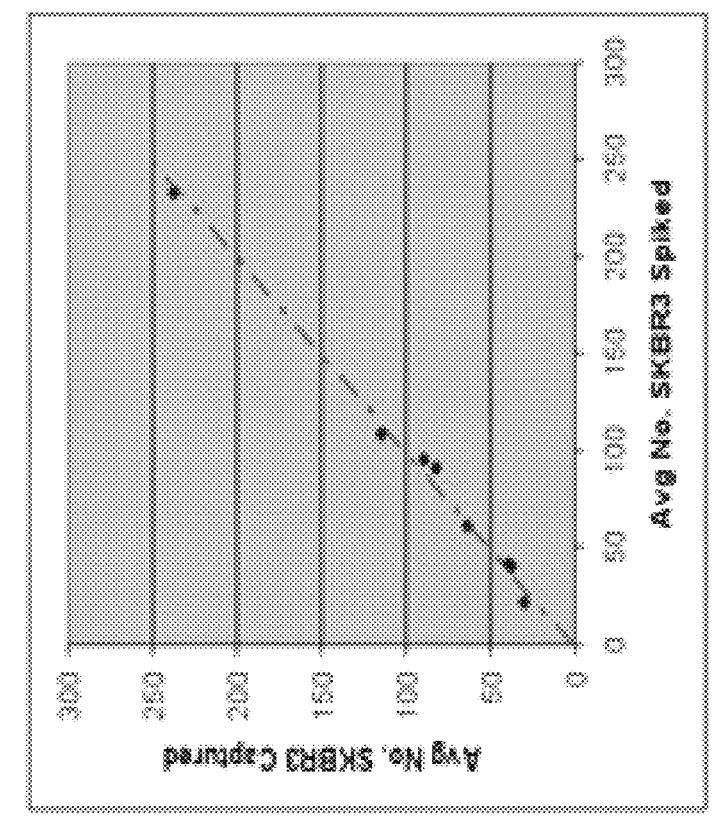
FIG. 17 shows the recovery of SKBr3 in a blood sample spiked with varying numbers of SKBr3 cells. The results show that the percent capture is independent of the cell input.

The results in FIG. 17 shows that approximately a 100% of the SKBr3 cells were recovered from the spiked samples. The data shows that the percent capture of cells by the micro-channel device is independent of the cell input.

Example 9. Antibody Cocktail is Superior at Capturing Circulating Tumor Cell (CTC) from Patient Blood Samples Using Micro-Channel Device Table 2 shows the results of circulating tumor cells (CTCs) captured on a micro-channel device from 10 mL blood samples from patients diagnosed with prostate, lung, pancreatic, renal cell, colorectal, breast and ovarian cancers. The blood samples were pre-labeled with a cocktail of soluble antibodies containing antibodies directed against CD340, EGFR, CD318, Muc-1, Trop-2, EpCam, Mov-18, and MSC, or a anti-EpCAM only. Cells were identified by staining with fluorescently labeled anti-cytokeratin.

TABLE 2

| Sample No.* | Anti-EpCAM only | MAb Cocktail |
| --- | --- | --- |
| 1 (16283 - Prostate) | 0 | 2 |
| 2 (16302 - Prostate) | 0 | 3 |
| 3 (16318 - Prostate) | 95 | 77 |
| 4 (16291 - Ovarian) | 1 | 1 |
| 5 (16278 - Colo/rectal) | 0 | 4 |
| 6 (16288 - Lung) | 0 | 5 |
| 7 (16297 - Breast) | 1 | 3 |
| 8 (16296 - Breast) | 0 | 3 |

*Samples from prostate, lung, pancreatic, renal cell, colorectal, breast and ovarian cancers.

Table 2 shows that the blood samples pre-labeled with a soluble antibody cocktail is superior at capturing CTCs compared to samples pre-labeled with a single type of antibody alone.

Example 10. The Micro-Channel Device is Superior at Capturing CTCs when Blood Samples Obtained from Breast Cancer Patients that are Pre-Labeled with a Soluble Antibody Cocktail on a Micro-Channel Device as Compared to Capture of CTCs Using a Ferro-Magnetic Label Antibody Blood samples were pre-incubated with anti-EpCAM antibody for capture on a micro-channel device or pre-incubated with antibodies that are joined to microscopic iron particles (immunoferromagnetic Abs) and captured using CellSearch® (VERIDEX, LLC). The captured cells were stained for CK, CD45 markers and DAPI, a nuclei stain. The cells that were stained in-situ with $CK^+/CD45^-/DAPI^+$ were counted.

TABLE 3

| Sample ID | Total #CTCs by CEE ($CK^+/CD45^-/DAPI^+$)* | Veridex |
| --- | --- | --- |
| 16163 | 0 | 0 |
| 16170 | 0 | 0 |
| 16171 | 60 (34) | 54 |
| 16172 | 5 | 0 |
| 16173 | 0 | 1 |
| 16176 | 549 (325) | 1267 |
| 16187 | 104 (37) | 54 |
| 16196 | 0 | 0 |
| 16198 | 87 (27) | 32 |
| 16202 | 5 | 8 |
| 16203 | 2008 | 923 |
| 16205 | 78 | 51 |

*No Significant difference by Two Tailed t-test (P = 0.715)
Total CTC counts indicated in bold include robust, apoptotic and micronuclei; whereas numbers in parenthesis indicate robust CTCs.

Table 3 shows that the total number of CTCs captured on the micro-channel device that are $CK^+/CD45^-/DAPI^+$ are consistently more than the CTCs captured by the VERIDEX systems, indicating that the invention provides for superior capturing of CTCs.

Example 11. Post-Capture Molecular Analysis of Captured Cells Increases Identification of CTC as Cancer Cells in Stage III and IV Breast Cancer Patients Circulating tumor cells (CTCs) were captured from blood samples of Stage IV (Table 4) and III (Table 5) breast cancer patients. The CTCs were pre-labeled with an antibody cocktail, containing antibodies to CD340, EGFR, CD318, Muc-1, Trop-2, EpCam, Mov-18, and MSC, and were released from the micro-channel device. The captured cells were analyzed by fluorescent in-situ hybridization (FISH) for aneuploidy in chromosome 8 and 17, and amplification of the breast cancer marker, Her2 (Table 4) These cells were never released from the microchannel and all FISH is performed in the channel with cells relocated following enumeration for FISH analysis. The total number of CTCs found positive for aneuploidy were compared to the total number of cells stained positive for CK marker.

TABLE 4

| Sample # | #CTCs ($CK^+$) | #Aneuploid cells (Chrom 17 & 8) | Her2/chromosome 17 Ratio |
| --- | --- | --- | --- |
| 1 | 3 | 7 (6 $CK^-$) | 1.05 |
| 2 | 1 | 1 ($CK^-$) | 1.0 |
| 3 | 0 | 3 ($CK^-$) | 1.0 |

TABLE 4-continued

| Sample # | #CTCs (CK+) | #Aneuploid cells (Chrom 17 & 8) | Her2/chromosome 17 Ratio |
|---|---|---|---|
| 4 | 0 | 3 (CK−) | 1.0 |
| 5 | 0 | 4 (CK−) | 1.0 |
| 6 | 2 | 13 (CK−/CK+) | Mixed |
| 7 | 1 | 1 CK−) | 1.0 |
| 8 | 1 | 7 (CK−) | 0.95 |
| 9 | 510 | 7 (CK+) | 1.0 |
| 10 | 16 | 16 (CK−/CK+) | >6 |
| 11 | 1 | 2 (CK−) | 1.0 |
| 12 | 0 | 4 (CK−) | 1 |
| 13 | 0 | 2 (CK−) | 1 |
| 14 | 0 | 14 (CK−) | 1 |
| 15 | 0 | 1 (CK−) | 1.5 |
| 16 | 0 | 24 (CK−) | 1.98 |
| 17 | 3 | 9 (CK−) | 5.714 |

Table 4 shows that post-capture molecular analyses of CTCs from stage IV breast cancer patients for aneuploidy and Her2 amplification status are superior in detecting breast cancer cells from the captured CTCs compared to CK staining.

In Table 5, captured CTCs from the blood samples of patients diagnosed with Stage III cancer were analyzed for aneuploidy in chromosome 8, 11 and 17. The total number of CTCs found positive for aneuploidy were compared to the total number of cells stained positive for CK marker. The details of aneuploidy on chromosomes 8, 11 and 17 are shown.

captured CTCs are aneuploid cells indicating that these CTCs are tumor cells. In-situ hybridization study using FISH to detect Her2 (Table 4) amplification and aneuploidy (Table 4 and Table 5) confirms that captured CTCs which are CK− are breast cancer cells. The results in Tables 4 and 5 show that post-capture molecular analyses, such as amplification of the Her2 marker and detection of aneuploidy of the captured cells released from the micro-channel device, positively identify cancer cells in CK− cells from Stage III and IV cancer patients. This study shows that CTCs captured within the micro-channel device provide a robust method for identifying cancer cells which would otherwise be left undetected.

Example 12. Post-Capture Molecular Analysis of Captured Cells Increases Identification of CTC as Cancer Cells in Bladder Cancer Patients Circulating tumor cells (CTCs) were captured from blood samples of bladder cancer patients. The CTCs were pre-labeled with an antibody cocktail, containing antibodies to CD340, EGFR, CD318, Muc-1, Trop-2, EpCam, Mov-18, MSC, c-met and N-Cadherin. Captured cells were analyzed

TABLE 5

| Sample ID | #CTCS (CK+) | #Aneuploid cells | Aneuploid Details (Chromosomes 8, 11 and 17) |
|---|---|---|---|
| 16610 | 0 | 93 | 4—Monosomy 8; 6—Monosomy 11; 83—Monosomy 17 |
| 16620 | 0 | 55 | 26—Monosomy 8; 11—Monosomy 11; 16—Monosomy 17; 2—complex aneuploidy |
| 16621 | 0 | 54 | 8—Monosomy 8; 22—Monosomy 11; 23—Monosomy 17; 1—Trisomy 17 |
| 16631 | 0 | 169 | 11—Monosomy 8; 11—Monosomy 11; 265—Monosomy 17; 3—complex monosomies |
| 16632 | 0 | 61 | 9—Monosomy 8; 10—Monosomy 11; 40—Monosomy 17; 2—complex Monosomy 8, 11, 17 |
| 16633 | 0 | 6 | 2—Monosomy 8; 1—Monosomy 11; 3—Monosomy 17 |
| 16686 | 0 | 55 | 13—Monosomy 8; 13—Monosomy 11; 21 Monosomy 17; 1—Trisomy 8; 1—Trisomy 11; 1—Trisomy 17 |
| 16687 | 0 | 686 | 12—Monosomy 8; 82—Monosomy 11; 582—Monosomy 17 |
| 16720 | 0 | 56 | 8—Monosomy 8; 23—Monosomy 11; 25—Monosomy 17 |
| 16747 | 0 | 58 | 11—Monosomy 8; 19—Monosomy 11; 26—Monosomy 17; 1—Tetrapolid 8; 1—Trisomy 17 |
| 16754 | 0 | 531 | 21—Monosomy 8; 123—Monosomy 11; 380—Monosomy 17; 7—complex aneuploidy |

Although none of the CTCs captured from the blood of Stage III breast cancer patients were stained positive for CK marker (CK+), post-capture analyses for aneuploidy at chromosome 8, 11 and 17, showed that a large number of the captured CTCs directly within the micro-channel device by fluorescent in-situ hybridization for aneuploidy in chromosome 3, 7 and 17, and compared to staining for CK marker on the captured CTCs.

TABLE 6

| Sample ID | #CTCS (CK+) | #Aneuploid cells | Aneuploid Details (Chromosomes 3, 7 and 17) |
|---|---|---|---|
| 16660 | 0 | 17 | 12—Trisomy 3; 1—Monosomy 3; 2—Monosomy 7; 2—Monosomy 17 |
| 16664 | 0 | 13 | 1—Trisomy 3; 2—Monosomy 3; 4—Monosomy 7; 6—Monosomy 17 |
| 16708 | 0 | 27 | 14—Trisomy 3; 2—Monosomy 3; 8—Monosomy 17; 2—Monosomy 7; 1—Tetraploid 3 |
| 16714 | 0 | 78 | 7—Monosomy 3; 3—Monosomy 7; 68—Monosomy 17 |
| 16719 | 0 | 8 | 2—Monosomy 3; 1—Monosomy 7; 5—Monosomy 17 |

TABLE 6-continued

| Sample ID | #CTCS (CK+) | #Aneuploid cells | Aneuploid Details (Chromosomes 3, 7 and 17) |
|---|---|---|---|
| 16729 | 0 | 29 | 2—Monosomy 3; 5—Monosomy 7; 10—Monosomy 17; 12—Trisomy 3 |
| 16746 | 0 | 20 | 1—Monosomy 17; 13—Trisomy 3; 1—Trisomy 7; 2—Trisomy 17; 1—Monosomy 3; 2—Monosomy 7 |
| 16762 | 0 | 18 | 2—Monosomy 3; 12—Monosomy 17; 3—Trisomy 3; 1—complex aneuploid (triploid for 3, 7, 17) |
| 16761 | 0 | 46 | 1—Monosomy 3; 5-0 Monosomy 7; 8—Monosomy 17; 26—Trisomy 3; 2—Trisomy 17; 4—Tetraploid 3 |

Table 6 shows that the many of the captured cells from samples obtained from patients with bladder cancer which are stained negative for CK ($2^{nd}$ column) are aneuploid cells (monosomy, trisomy and/or tetraploid at chromosome 3, 7 and 17). The results in Table 6 show that the method is capable of identifying CTCs from blood obtained from different cancer types.

The results from these experiments show that the ability to identify aneuploidy and expression of specific markers in CTCs captured on a micro-channel device provide a means for predicting and managing diseases, such as cancer during the early stages of tumorigenesis or late stages of tumorigenesis where tumor cells have metastasized and escaped into the circulation. In addition, the method described is also applicable for monitoring treatment efficacy or failure.

Example 13. Efficient Capture of Circulating Tumor Cells with a Novel Immunocytochemical Microfluidic Device Ability to perform cytogenetic interrogations on circulating tumor cells (CTCs) from the blood of cancer patients is vital for progressing toward targeted, individualized treatments. CTCs are rare compared to normal (bystander) blood cells, found in ratios as low as $1:10^9$. The isolation techniques used have been immunocytochemical technologies that label CTCs for separation based on unique surface antigens that distinguish them from normal bystander cells. The method discussed here utilizes biotin-tagged (directly or indirectly) antibodies that bind selectively to CTCs. The antibodies are introduced into a suspension of blood cells intending that only CTCs will display surface biotin molecules. Next, the cell suspension is passed through a microfluidic flow channel that contains about 9,000 transverse, streptavidin coated posts. A CTC that makes contact with a post has the opportunity to engage in a biotin-streptavidin reaction that immobilizes the cell. Bystander blood cells remain in suspension and pass through the channel. The goal of the present example is to establish the technical performance of these channels as a function of antigen density and operating conditions, especially flow-rate. At 18 µL/min, over 70% of cells are captured at antigen densities greater than 30,000 sites/cell while 50% of cells are captured at antigen densities greater than 10,000. It is found that lower flow-rates lead to decreasing cell capture probabilities, indicating that some streamlines develop which are never close enough to a post to allow cell-post contact. Future modeling and streamline studies using computational fluid dynamics software could aid in optimization of channel performance for capture of rare cells.

Physicians have long noted the presence of circulating tumor cells (CTCs) in the blood of cancer patients (Liotta, L. A., et al., *Cancer Research* 34:997-1004 (1974)). CTC detection plays an increasing role in cancer diagnosis, prognostication, and surveillance (Racila, E., et al., *Proceedings of the National Academy of Sciences*, 95:4589-4594 (1998); Allard, W. J., et al., *Clinical Cancer Research* 10:6897-6904 (2004); Meng, S., et al., *Clinical Cancer Research* 10:8152-8162 (2004); and Pantel, K., et al., *Nature Reviews Cancer* 8:329-340 (2008)). With the advent of individualized, targeted cancer therapies which depend on genetic analysis of tumor cells, a non-invasive and inexpensive platform for CTC capture and interrogation has become a necessity. In a blood sample containing approximately $10 \times 10^9$ healthy cells, there may be 1 to 1000 CTCs (Allard, W. J., et al., *Clinical Cancer Research* 10:6897-6904 (2004)). Thus, high-yield, high-purity isolation is difficult. The leading CTC isolation technologies have been reviewed (Pantel, K., et al., *Nature Reviews Cancer* 8:329-340 (2008); U.S. Pat. No. 7,666,308 and Nagrath, S., et al., *Nature,* 450(7173): 1235-9 (2007)) and two broad separation criteria—physical and immunocytochemical—can be seen to encompass the many approaches to the problem. Physical separation methods include filtration, addressing primarily cell size, and density gradient centrifugation, addressing the differences in density amongst cell types. Density gradient is commonly used as a pre-enrichment step where it may reduce the ratio of background blood cells to CTCs by several orders of magnitude, primarily by removing red blood cells (RBCs) and heavier white blood cells such as granulocytes. This example describes immunocytochemical approaches with reference to a system developed in the inventors' laboratory.

Immunocytochemical technologies exploit the selective binding of particular antibodies to surface antigens present on CTCs that are not present on bystander blood cells. Since association with an antibody does not, per se, render a cell separable, the antibody must be predisposed to participate in a subsequent separation process. Two approaches have been taken: either (1) the antibodies are admixed with the cell sample to bind to cells with complexation occurring throughout the suspending volume, in which case the complexes must subsequently be captured, or (2) cells are interrogated as they follow a directed flow path over antibody that has been immobilized onto a collecting surface.

The Veridex CellSearch® system uses the first approach, introducing antibody-bearing magnetic particles ("ferrofluids") into the blood to search out and bind to CTCs (Riethdorf, S., et al., *Clinical Cancer Research* 13.3:920-928 (2007)). The ferrofluid-CTC complexes are collected under an applied magnetic field onto the surface of a plate for quantification and recovery. Several studies indicate that CellSearch recovers CTCs from the blood of up to 70% of patients with metastatic breast and prostate cancer (Riethdorf, S., et al., *Clinical Cancer Research* 13.3:920-928 (2007) and Danila, D. C., et al., *Clinical Cancer Research* 13.23:7053-7058 (2007)). However, in one study, CellSearch only recovered CTCs from 20-40% patients with metastatic breast, ovarian, colorectal, lung, and other metastatic cancers (Allard, W. J., et al., *Clinical Cancer Research* 10:6897-6904 (2004)). Nevertheless, this product has shown success in predicting patient survival rates, and is serving as an important diagnostic tool for clinicians. (Allard, W. J., et al., *Clinical Cancer Research* 10:6897-6904 (2004); Riethdorf, S., et al., *Clinical Cancer Research* 13(3):920-928 (2007); Danila, D. C., et al., *Clinical Cancer Research* 13(23):7053-7058 (2007); Cohen, S. J., et al., *Journal of Clinical Oncology* 26(19):3213-3221 (2008)). The Veridex method allows for different biotinylated antibodies to be used solely or in combination, allowing for the modulation of surface antibody density and offering flexibility in selecting different cell types.

The second method is exemplified by the "CTC-chip," a microfluidic device developed by the bio-MEMS Resource Center at Harvard Medical School, Boston, Mass. (de Bono, J. S., et al., *Clinical Cancer Research* 14(19):6302-6309 (2008)). The CTC-chip platform is a microfluidic channel with 78,000 micron-scale, transverse posts ordered in a regular geometric array. These posts are coated with antibodies specific to a CTC surface antigen so that given sufficient contact, antibody-antigen reactions occur, binding CTCs to the interior surface of the chip. Suspended cells flow over the posts, allowing for cell-post contact (Sequist, L. V., et al., *Journal of Thoracic Oncology* 4(3):281-283 (2009)). Published data report recovery of CTCs from up to 99% of metastatic lung, prostate, pancreatic, breast and colon cancer patients, with captured CTCs at a purity level of 50% (de Bono, J. S., et al., *Clinical Cancer Research* 14(19):6302-6309 (2008)).

Each method for isolating CTC's based on their surface antigens has advantages and disadvantages. Ligating free antibodies gives an one of skill, maximum choice of antibodies including "cocktails" with differently proportioned antibody components. Capturing with immobilized antibodies avoids the need for subsequent collection of ligated cells and allows for the choice of a desirable display of captured cells, allowing location and identification by staining with fluorescent secondary antibodies and subsequent analysis by fluorescence in-situ hybridization (FISH) (Handy, B. C. *Biomarkers Medicine* 4.1: 129-131 (2010); Maheswaran, S., et al., *The New England Journal of Medicine* 359:366-377 (2008); and Lee, R. J., et al., *ASCO*. Orlando, Fla.: *Journal of Clinical Oncology*, 2009. 5149). A combination of these two methods in which cells are captured onto a display surface via the use of biotinylated soluble antibodies using a channel labeled with streptavidin offers special advantages. Antibody selection and specification of the cocktail remains with each investigator, with biotinylation as the only extra step. Ligation time is controlled by the investigator and is not coupled to channel size and flowrates. The more difficult task of preparing the channel surface is left to the manufacturer who uses only one, standard capturing agent, streptavidin. The capture kinetics within the chamber vary principally with the number of antibodies associated with a cell and not the nature of the ligated antibody, since only the biotin-streptavidin reaction occurs during capture.

This example describes an analytical and quantitative modeling approach to a novel technology of this type. This device, called Cell Enrichment and Extraction™ (CEE) channel, was developed in the inventors' laboratories. It allows for a wide, investigator-driven choice of antibody or antibodies—a feature that may be crucial in obtaining comprehensive capture of heterogeneous cell populations. As described above, captured cells are displayed desirably for further investigations, such as FISH.

The technology calls for pre-enrichment of a blood sample using density centrifugation to remove RBCs. The enriched cell fraction is then incubated with biotin-labeled antibodies targeted toward specified CTCs. Next, a suspension of blood cells is drawn through a microfluidic channel manufactured out of polydimethylsiloxane (PDMS), using standard soft lithography manufacturing techniques for microelectromechanical systems (MEMs) and the channel is bonded to a glass coverslip. The entire inner lumen of the covered channel (both the PDMS and glass coverslip) is derivitized with streptavidin, tethered to the PDMS via a long polyethylene glycol (PEG) chain.

The channel interior contains about 9,000 transverse, randomly sized, randomly positioned posts, which are 75-150 μm in diameter. The distribution of post sizes, dimensions, and positions relative to each other have been designed to minimize straight-line, regularized streamline flow, and thus to encourage frequent and unbiased collisions between posts and cells (U.S. Pat. No. 7,695,956). The total volume occupied by the posts is about 25% of the total volume of the channel. The channel itself holds 15 μL of fluid volume, discounting the volume of the inlet and outlet ports. While density of posts in the channel could be higher, a minimum post separation was set at 70 μm for this example in order prevent clogging when encountering cell clumps, debris, micro emboli, etc. The height of the channel is ~55 μm, with posts spanning the entire height. All channels are exact replicates, which aids post capture analysis where captured cell positions are recorded.

Cells are seen to make contact with a post, slow, and roll around the post. Because the CTCs are coated in antibodies derivatized with biotin, which rapidly and nearly irreversibly binds to streptavidin, when a cocktail of biotinylated antibodies is used the number of possible sites of adhesion to a post per cell is increased because a common ligand pair (biotin/streptavidin) spans all antigen-antibody pairs of interest.

Cell capture can be conceptualized as the number of opportunities for capture afforded each cell in a sample, multiplied by the number of cells exposed, multiplied by the probability of each opportunity to result in actual capture. In flow fields seen in the CEE chamber (as well as the CTC chip), a uniform flow field is established within an array that can be roughly defined as a number, R, of rows (each containing W posts spaced to span the width of the chamber). Cells zig-zag, row-to-row. The opportunity for any one cell to be captured is then proportional to the number of rows, so long as wholesale bypassing of the posts is avoided. The number of cells exposed can be obtained as the product of cell concentration multiplied by the volume of suspension flowed through the chamber.

The most important and difficult component of cell capture to define and optimize is the local probability, k, of capture. This probability will be affected by antigen expression level on the particular cell, density of surface tethered recognition elements, streptavidin in this case, on the antibody, the antibody-antigen affinity constant and the flow conditions. Among similar cells and in fully developed (not row-dependent) flows, capture probability is likely to be independent of row number and to depend on geometry (post size and spacing) and flow-rate as well as the density and molecular configuration of ligands on the target cells and their molecular cognates affixed to the wetted surfaces of the chamber. Fast flows may inhibit capture by not providing sufficient time for reaction at any point along a cell's path and by exerting a shearing effect on partially ligated cells, but some fluid movement is necessary, and some inertial effects abetted by faster flows could improve capture.

Whatever the complex relationships defining the capture probability, it is experimentally measurable and the measured value provides a fundamental ruler with which to compare any of the different circumstances described above. Thus we formally define k as the chance of capture as a cell passes each row of posts and n as the number of cells in suspension flowing past a given row. Therefore if n cells are in suspension flowing past a given row, the number of cells captured in that row is k×n, where k is the probability of cell capture while passing a given row. The change in the number of cells left in suspension with respect to the number of rows passed is expressed $$\frac{dn}{dr} = -k \times n$$

so that the number of cells captured in an arbitrary section of channel is $$\int -k \times n dr$$

If $n_0$ is the number of cells flowing into a channel segment, it follows that the number of cells which are left in suspension after an arbitrary number of rows is $$n = n_0 - \int k \times n dr$$

This directly leads to an equation for $n$:

$$n = n_0 e^{-kr}$$

This experiment calls for a count of the cells captured in distinct regions of r rows along the microchannel. This value $n_{obs}$, the compliment of n is defined as:

$$n_{cap} = n_0 - n_0 e^{-kr}$$

This leads to an equation for the capture probability per row of a cell under a given condition in a channel segment of r rows:

$$k = \frac{-\ln \frac{n_0 - r_{cap}}{n_0}}{r}$$

The k values are expected to remain constant, whence different k's observed for different channel segments may be indicative of unexpected flow effects or a change in the cell population, e.g., because the cells most likely to adhere are depleted, leaving a population which is then less adherent. Whether k values vary or remain constant, profiles of captured cells in comparison to the exponential distribution expected for constant k permits assessing effects of local changes in flow and in adherence probability because of changes in the remaining cell population. These data may aid in improvement of channel design and may assist in the assessment of the labeled cell population.

General Protocol.

Figure 18:
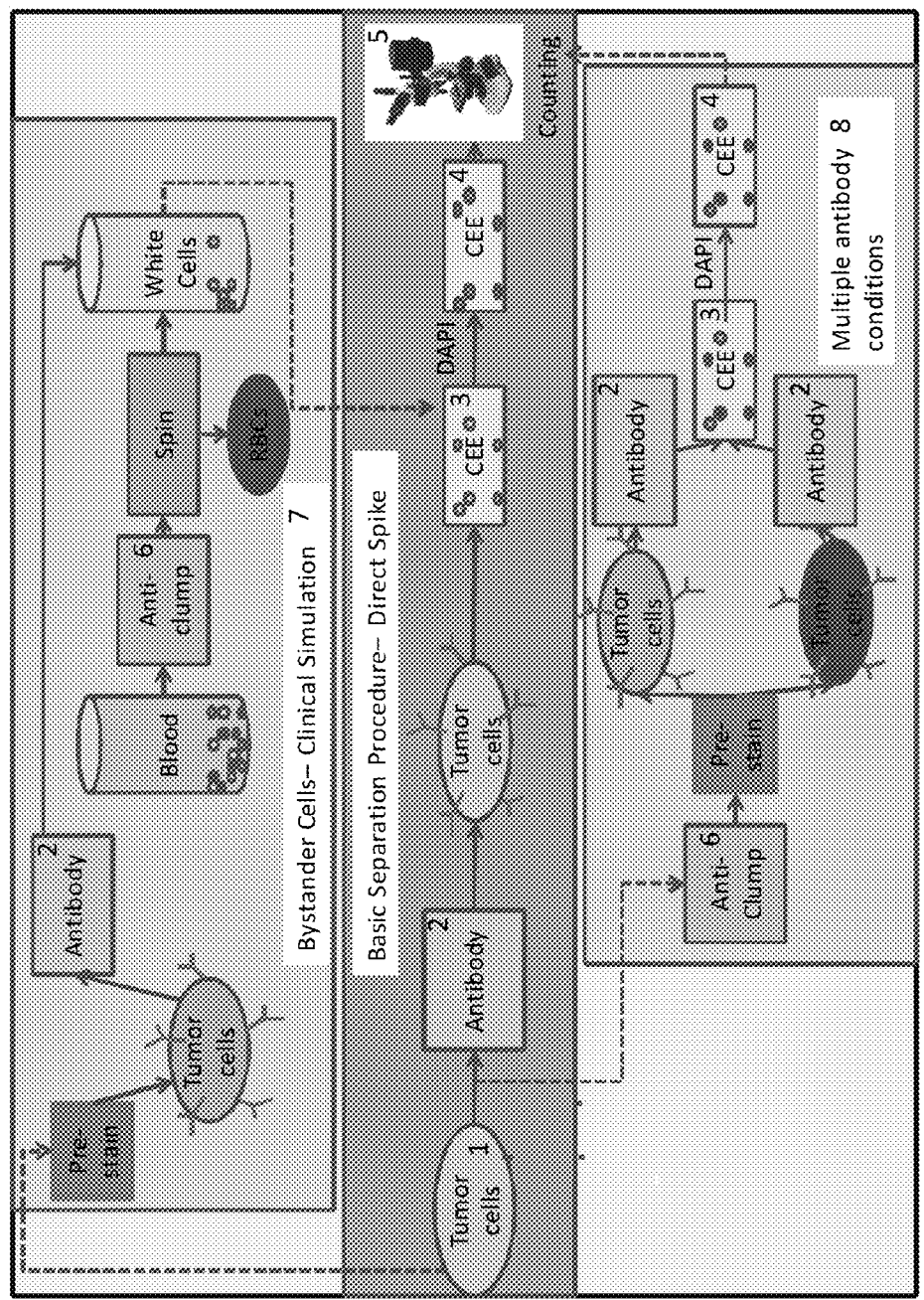
FIG. 18 shows the General Protocol. Tumor cells (FIG. 18:1) are incubated with biotin-tagged antibody.

Cell suspensions of buffy coat cells, CTCs or CTC proxies (FIG. 18: 1) are incubated with biotin-tagged antibody. (FIG. 18: 2) Next, a suspension of cells is drawn through the channel. Wherever a CTC makes contact with a post, the biotin on its surface reacts with streptavidin, thus immobilizing labeled cells. (FIG. 18: 3) Next, the captured cells are fluorescently stained (FIG. 18: 4) and counted using fluorescent microscopy (FIG. 18: 5). Modifications to this procedure allow for measurement of the effects of anti-clumping reagent (FIG. 18:6) and bystander white blood cells (FIG. 18: 7), as done in Part I. An additional pre-labeling step allows for tumor cells to be incubated with multiple antibodies so cells selected according to different antigens can be simultaneously captured in one channel at a particular flow rate, as done in Part II (FIG. 18: 8). Cell lines, antibody preparation and microchannel set-up are identical for all experiments.

CEE Microchannel Manufacturing.

Figure 21:
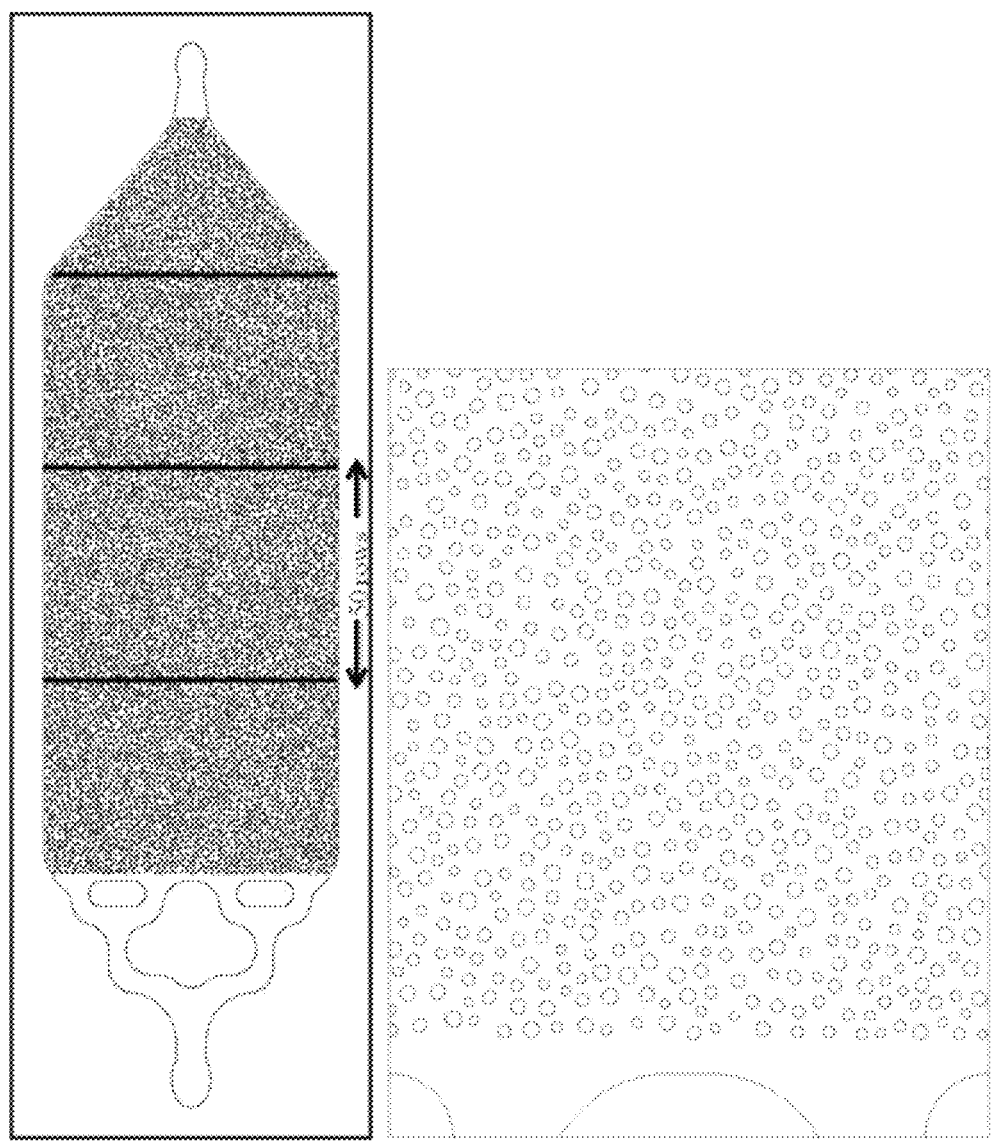
FIG. 21 shows schematic of capture zones.

CEE microchannels were manufactured in-house at Biocept, Inc. (San Diego, Calif.). A brief description of the process follows. A negative mask is created from an epoxy resin (EPON SU-8), spun onto silicon wafer substrates as a 50 µm thick film of photoresist, and hardened by baking A desired pattern is exposed onto the photoresist through a Contact Mask Aligner. The exposed photoresist is developed in an SU-8 developer, a process which creates a negative-pattern mold that is then used as a master for replication of the channel geometry in PDMS. (FIG. 21)

PDMS prepolymer and a curing agent (Sylgard 184 kit, Dow Corning) are mixed at a 10:1 ratio by weight. In order to avoid air bubble generation, the mixed polymer is first degassed in a vacuum chamber and then poured onto the master mold, which has been secured inside a molding cavity that also holds pins predetermining inlet and outlet ports. The PDMS is then cured at 90° C. and removed from the molding cavity.

The lumen of the channel is created by adhering the patterned face of the PDMS body to a glass coverslip after treatment of both surfaces with an oxygen plasma. A coverslip is used instead of a glass slide to enable high-resolution fluorescence microscopy. With coverslip thicknesses of 100 to 150 µm, magnifications up to 1000×(100× objective, plus a 10× eyepiece) are possible.

The assembled channels are then chemically derivitized with primary amines using amino-silane (3-aminopropyltriethoxysilane 99%, Aldrich). PEG is then attached to the amines through the NHS (N-hydroxysuccinimide) end of an NHS-PEG27-Maleimide linker. A thiolated streptavidin is then reacted to the maleimide end of the linker to finish the derivitization of the channel.

Microchannel Set-Up.

Figure 19:
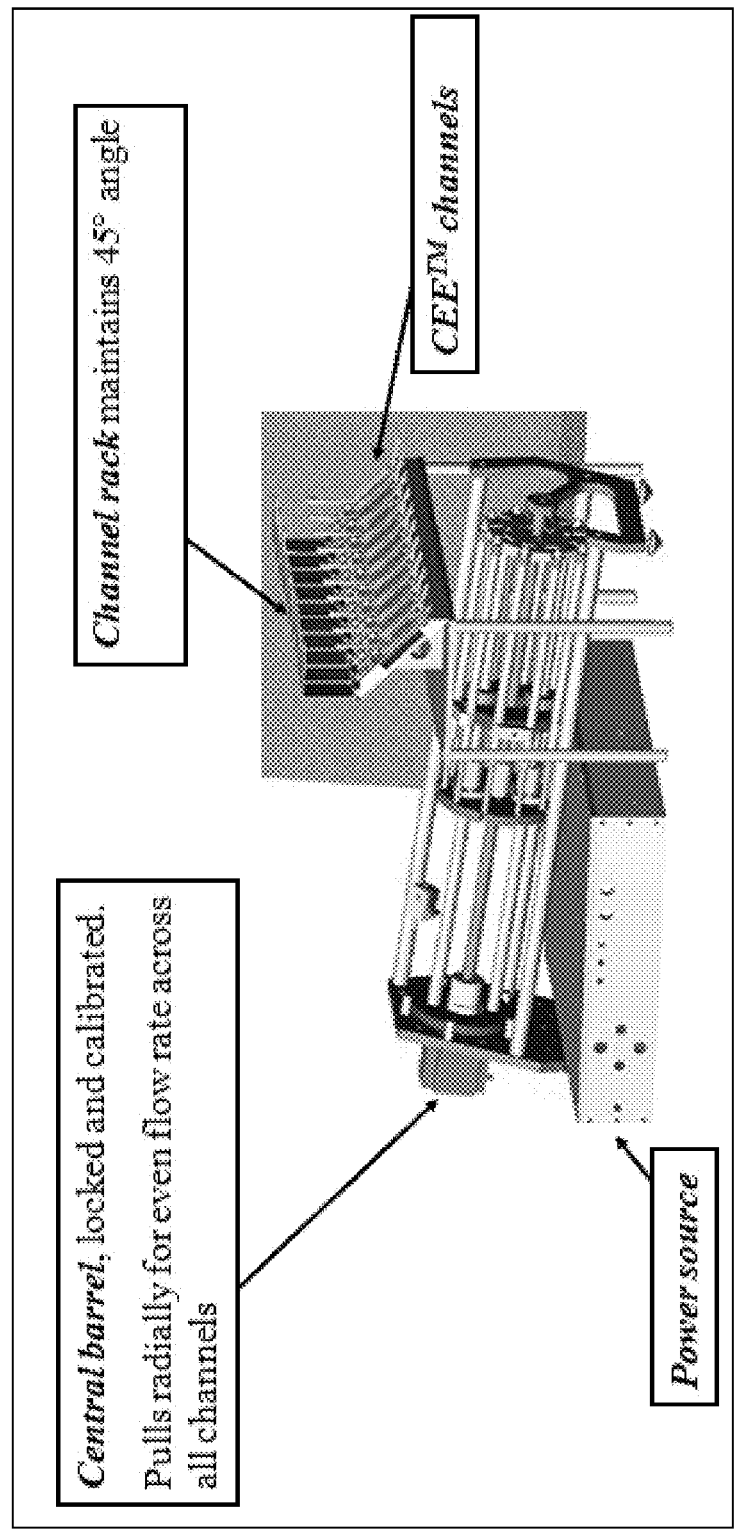
FIG. 19 shows the Channel rack set up.

For each experiment, four microchannels are run for each antibody condition. A customized syringe pump which can accept up to 10 channels was designed at Biocept which uses a Vextra stepping motor from Oriental Motor Company (Tokyo, Japan). Microchannels are attached to channel holding racks (also designed by Biocept) which maintain the channel angle at 45 degrees with each microchannel is connected to one of the pump's syringes via Teflon tubing connecting the outlet to a syringe. The 10 syringes are arranged radially around a central barrel which is locked, calibrated, and set to pull equally on all syringes simultaneously (FIG. 19). All reagents used in the cell capture and staining process are degassed in vacuum chambers at 27-29 in. Hg vacuum for 3-5 minutes. After microchannels are attached to pumps, they are flushed twice with running buffer (PBS/BSA/EDTA) at high flow rates (150 µL/min).

Cancer Cell Lines.

Standardized tumor cells are used as CTC proxies. In order to eliminate day-to-day variability inherent in cell lines, a single batch of frozen SKOV (human ovarian cancer cells) (ATCC ID # SK-OV-3-IP1) are used to control for ovarian cells and normalize for expression of surface epithelial cell adhesion molecule (EpCAM). The cell line is grown according to standard in-house protocols, aliquoted into 50,000 cell pellets and kept frozen at −81° C. (FIG. 18:1).

Using fluorescence-activated cell sorting, (FACS) EpCAM expression was estimated to be 60 000 antigen molecules per cell. Measurement of EpCAM surface antigens was performed by incubating non-permeabilized SKOV cells with mouse anti-human EpCAM antibody, followed by incubation with PE-labeled anti-mouse IgG, according to standard flow cytometry protocol. After additional washes, to remove excess antibody, the cells were analyzed by flow cytometry. Flow cytometric estimation of antibodies bound per cell was determined by using BD Quantibrite™ PE beads (BD Biosciences). By using known ratios of PE to antibodies, PE molecules per cell were converted to antibodies per cell.

SKOV cells are suspended in either fetal bovine serum (FBS) purchased from ATCC or media (as indicated in the procedures below) to yield suspensions of 2,000-5,000 cells/mL. The cells are incubated in serum overnight to mimic the clinical sample conditions.

Antibody Preparation and Incubation.

To create cell samples with varying surface biotin density, cells are incubated in solutions of anti-EpCAM, composed of set ratios of biotinylated and non-biotinylated antibody (FIGS. 18:2 and 20). Although selections of cell lines with different EpCAM expression were available, this approach was determined to be more repeatable and more controllable than attempting to vary either cell line or antibody.

To ensure that all binding sites are occupied, anti-epithelial cell adhesion molecule antibody (anti-EpCAM) 0.25 mg/mL (T1; BD Biosciences, biotinylated in-house) is added in excess t a ratio of binding sites to antibodies of about 1:2,000. Since biotin is small compared to the antibody (244 g/mol compared to 40,000 g/mol) we assume no difference in binding due to steric hindrance. Because the same antibody clone is used in both cases, and because the solution is incubated for sufficient time (greater than 30 minutes), we assume no kinetic difference in binding. These assumptions have been validated by flow cytometry, where both biotinylated and non-biotinylated versions of EpCAM antibody were titered on cell lines and showed no significant differences in binding. Thus, by controlling the percentage of antibodies which are biotinylated, the surface biotin density can be manipulated. For the remainder of this example this parameter will be referred to as "effective antigen density" which has units of biotinylated antibodies per cell.

Part I: Variable Effective Antigen Densities.

The first part of the experiment seeks to determine the correlation between capture efficiency and effective antigen density variation at a fixed channel flow rate.

Direct Spike Experiment Preparation.

Untreated SKOV aliquots are suspended in RPMI-1640 medium purchased from ATCC (Manassas, Va.) (FIG. 18: 1-5). Cells are aliquoted into 1.7 mL Eppendorf tubes and each is incubated with an antibody solution as described above (FIG. 18: 2). The number of cells per µL is manually counted and a volume of cell suspension containing approximately 150 cells is calculated for each antibody solution. Aliquots of this volume are analyzed with the microchannel (FIG. 18: 3) and then by staining and microscopic visualization (FIG. 18: 4-5). These procedures are described in detail below.

Bystander Cell Experiment (Clinical Simulation) Preparation.

SKOV aliquots are thawed at 37° C. and added to a vacutainer containing FBS (FIG. 18:7). Anti-clumping reagent is added to this suspension at a concentration of 2 w/vol. %. Tumor cells pre-labeled with cytosolic label Cell Trace Kit Green (Invitron; Eugene, Oreg.) are subsequently aliquoted into 1.7 mL Eppendorf tubes and incubated with an antibody solution. For each microchannel, one Eppendorf tube containing approximately 150 labeled SKOV cells is used. The total number of input cells is confirmed for each antibody solution by counting the cells in an equal volume on a microscope slide.

Bystander cells are prepared from mononuclear cells (PBMC) using a Percoll density gradient method and Leucosep tubes (Greiner). Each Leucosep tube is pre-filled with Percoll Plus (GE Healthcare, UK) at a density of 1.083 g/mL (adjusted to normal saline levels) and stored at room temperature (RT). Each 10 mL blood sample is diluted three fold with a 1×PBS/1× Casein/Arginine/EDTA buffer and poured directly into a Leucosep tube and centrifuged. After separation, the upper layer (above the separation barrier) is recovered by decanting into a 50 mL conical tube through a 70 µm cell strainer (BD). The decanted sample is washed and pelleted. Following supernatant aspiration using a vacuum wand, a 1 mL cell pellet is resuspended and incubated with antibody cocktail for 30 min at room temperature. The final 1 mL cell pellet is washed three more times with PBS/Casein/EDTA. Each wash step consists of a 400G 10 min centrifugation, followed by supernatant aspiration. The resulting 1 mL pellet is resuspended in 1×PBS and counted so that a volume corresponding to ~$10^7$ cells can be added to each Eppendorf tube containing an SKOV aliquot. These aliquots now contain about 25×$10^6$ WBCs and about 150 tumor cells, which is approximately the ratio expected in a clinical sample. Next, aliquots are analyzed using the microchannel as described below.

Microchannel Capture and Staining.

Each microchannel loading tip is filled with PBS/BSA/EDTA and the pump is switched on at a volumetric flow rate of 18 µL/min (FIG. 18: 3-4). The desired aliquot is loaded into the tip of each channel and run continuously until loading tip has emptied, refilled with running buffer, and emptied again. A final rinse is done with 1× phosphate buffer solution (PBS) from Mediatech, Inc. (Manassas, Va.).

Next, the cells are fixed to posts with a Polyethylene glycol N-hydroxysuccinimide (PEG-NHS) protein cross-linker (Pierce. Rockford, Ill.) for 10 min followed by quenching in methanol (MeOH) buffer for an additional 10 min. The channel is rinsed with 1×PBS to remove remaining MeOH. The cell nuclei are then stained using 4',6-diamidino-2-phenylindole (DAPI III) counterstain (Abbott Molecular Inc.; Des Plaines, Ill.).

Microchannel Enumeration and Capture Position.

Each microchannel is scored on an Olympus Bx51 fluorescent microscope at 200× magnification using a DAPI filter (excitation/emission λ=350[±50]/470[±40] nm) to determine the number of cells captured as well as their positions. For the bystander cell experiment, captured cells are confirmed to be green-labeled SKOVs by visualization (excitation/emission λ=480[±40]/631 [±23] nm light). The capture position of a cell is recorded according as lying in the inlet, outlet, or in one of 3 bulk capture zones (FIG. 21).

Part II: Variable Flow Rates.

The second group of experiments, described here, seek to determine the correlation between capture efficiency and one of 5 different channel flow rates.

Variable Flow Rate Experiment Set Up.

In these experiments two SKOV cell populations differing only in their concentration of biotinylated antibody are to be spiked together into each channel studied. SKOV cells are first diluted and divided into two tubes (FIG. 18: 8). The cells in one tube are labeled green using Cell Trace Kit Green and those in the other tube, red, using Cell Trace Kit Red, both from Invitrogen (Eugene, Oreg.). Next, the cells in each tube are incubated with a different concentration of biotinylated antibody. From each tube, volumes of suspension corresponding to a set number of cells is aliquoted. One of each of these aliquots is to be spiked into each CEE channel to be analyzed and visualized by the procedures described below. Thus, each channel will receive two distinguishable cell populations differing in biotinylated antibody density. Each channel thus yields information on two cell populations of known difference, each subjected to the same channel conditions.

Microchannel Capture and Staining.

One pump containing four channels is run at each of the pre-determined flow rates (FIG. 18: 3-4). Each microchannel loading tip is then filled with running buffer and the pump is switched on at the desired running rate, and an aliquot is loaded into the tip of each channel. Microchannels are run continuously at the designated volumetric flow rate until loading tip has been emptied, then twice refilled with buffer and emptied to rinse the channel. A final rinse is done with 1×PBS. Fixing and staining procedures are as described in Part I.

Microchannel Enumeration and Capture Position.

Each microchannel is then scored on an Olympus Bx51 fluorescent microscope using a triple DAPI/red/green filter (excitation/emission λ=350[±50]/470[±40]; λ=480[±40]/631[±23]; and λ=460 [±13]/535[±50] nm light, respectively) in order to distinguish the green-labeled cells from the red-labeled cells (FIG. 18: 5). Again, capture position is recorded according to whether the cell has been found in the inlet, outlet, or one of 3 bulk capture zones.

The results are, then, the number of cells counted (captured) in each of the three capture zones after the loading tip has been emptied. These data are analyzed along with the known number of cells delivered to the chamber.

Capture efficiency, C.

The simplest measure of performance for a CTC capture device is its yield of evaluable cells relative to the total number of CTCs or CTC surrogates with which the device has been challenged. This ratio is called capture efficiency:

$$C = \frac{n_{cap}}{n_0}$$

Figure 22:
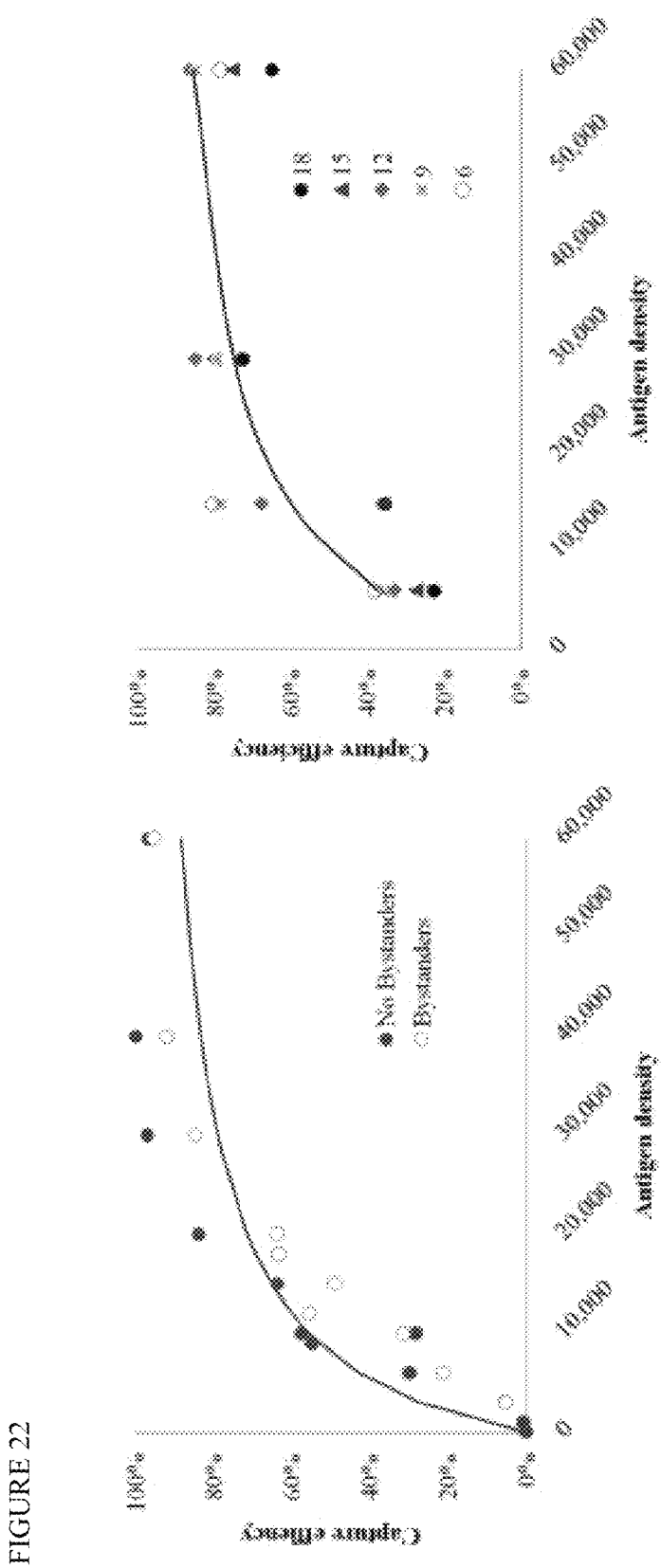
FIG. 22 shows capture efficiency vs. antigen density. Plot of capture efficiencies against effective antigen density. Series corresponds to trials with and without bystander cells. Series corresponds to flow rate. Both plots show high capture at antigen densities as low as 30,000, which falls off rapidly as antigen density is decreased below 10,000.

While this measure is expected to be responsive to antigen loading and the appropriateness of operating conditions relative to the device' design, one expects predictable high efficiency that is robust against the presence of bystander cells and small variations in preparative technique and operating conditions. This is supported by FIG. 22, which shows a plot of capture efficiency versus effective antigen density for two different conditions: with and without bystander cells. FIG. 22a compares trials with and without bystander cells. FIG. 22b, shows the variation of capture efficiency with flow rate. Both plots show high capture at antigen densities as low as 30,000, falling off rapidly as antigen density is decreased below 10,000. Capture efficiencies remain above 70% for effective antigen densities higher than 30,000, but drop to 50% at effective antigen densities of about 10,000.

Probability of Capture, k.

For ease of in situ inspection of cells under the microscope, it is desirable that they be captured and displayed with appropriate spacing, not overlapping in the field of view, but short enough to be efficiently scanned by the technician. Thus, an important characterization for a channel intended for in-situ inspection is the relationship between the number of rows of posts in a channel and the number of cells which adhere under specific conditions. The parameter k can be used to unambiguously compare data collected in various geometries at varying flows, and with different types and number per cell of binding moieties. In these experiments, each k value is assumed constant within each capture zone i (i=1, 2, 3) (FIG. 20) and is calculated for each zone as follows:

$$k_i = \left. \frac{-\ln\frac{n_{out}}{n_0}}{r} \right|_i = \frac{-\ln\left(1 - \frac{n_{cap,i}}{n_{0,i}}\right)}{r_i}$$

where r is the number of rows in the zone, now the number of cells that leave zone i, and $n_0$ the number of cells which enter it. The value of r is 50 for each zone.

Differences in adherence among cells entering a field of posts can depend upon cell properties. Without differences no useful distinction is made. Differences relevant to a cell's properties are useful while those depending upon the particular path that a cell follows are not. Thus, since many paths are possible, they should be identical. However, near a particular post in a field of posts the chance of adherence depends not only on the cell's "stickiness" but also on how the cell approaches the particular post.

Figure 20:
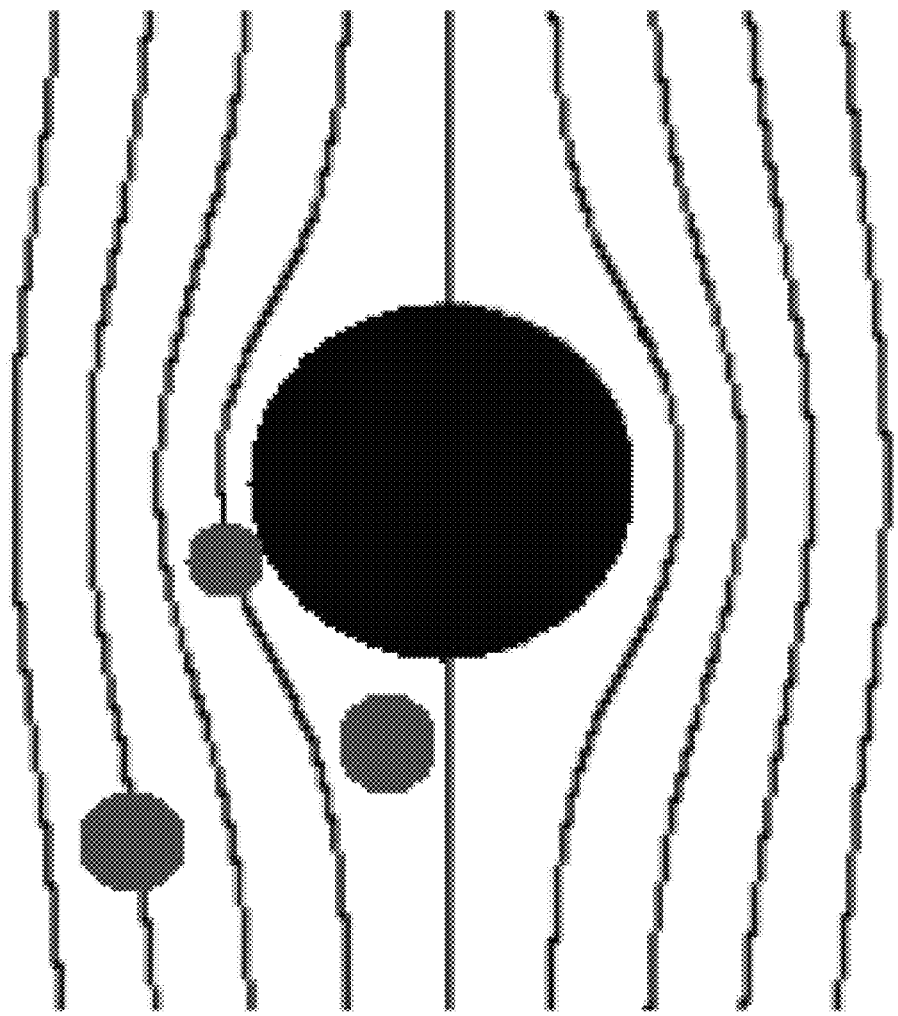
FIG. 20 Streamlines around post.

Cells travel along streamlines that are well defined (Adams, A. A, *J. Am. Chem. Soc.* 130(27):8633 (2008)). As seen in FIG. 20, for a cell of a given diameter, perhaps 10 μm approaching a post whose diameter is about 10× larger, there are three possibilities: (i) a direct hit when the cell is on or near a streamline that points to the center of a post; or (ii) a glancing blow when the cell travels around the post but at some angle comes close enough to the post to adhere, or (iii) a total miss when the cell is on a streamline that does not bring the cell near enough to the post surface to allow adherence. If a cell passes many rows of posts and if the orientation of the cell relative to the posts does not depend upon how the cell passed an antecedent post, all cells should have, on average, the same chance of adherence, some sooner, some later, and some never if the number of rows is too small. In fact, the streamlines in an ordered bed of posts are regular and a cell on a streamline that bypasses a post in one row will be disposed to pass the next post it encounters. This consistent bypassing creates a difference for some cells that depends upon the particular path that these cells followed. It is possible for cells to move across streamlines but that is unlikely when cell concentrations and flow velocities are both low.

Both the Toner group (Sequist, L. V., et al., *Journal of Thoracic Oncology* 4(3):281-283 (2009) and Lee, R. J. et al., *J. Clin. Oncol.* (2009),) and the present invention have recognized this problem, the former by "staggering" the alignment of rows at intervals along the flow path and we by designing a bed in which, as noted above, the diameter and spacing of posts is randomized by a computer generation of the photolithographic mask that defines the bed. Computational fluid dynamic (CFD) studies, in progress, in the authors' laboratory indicate that randomization is more effective than staggering. The following results show the effect of varying flow rate and the effect of varying antigen density upon the capture efficiency.

Results Obtained at Different Flow-Rates.

Figure 23:
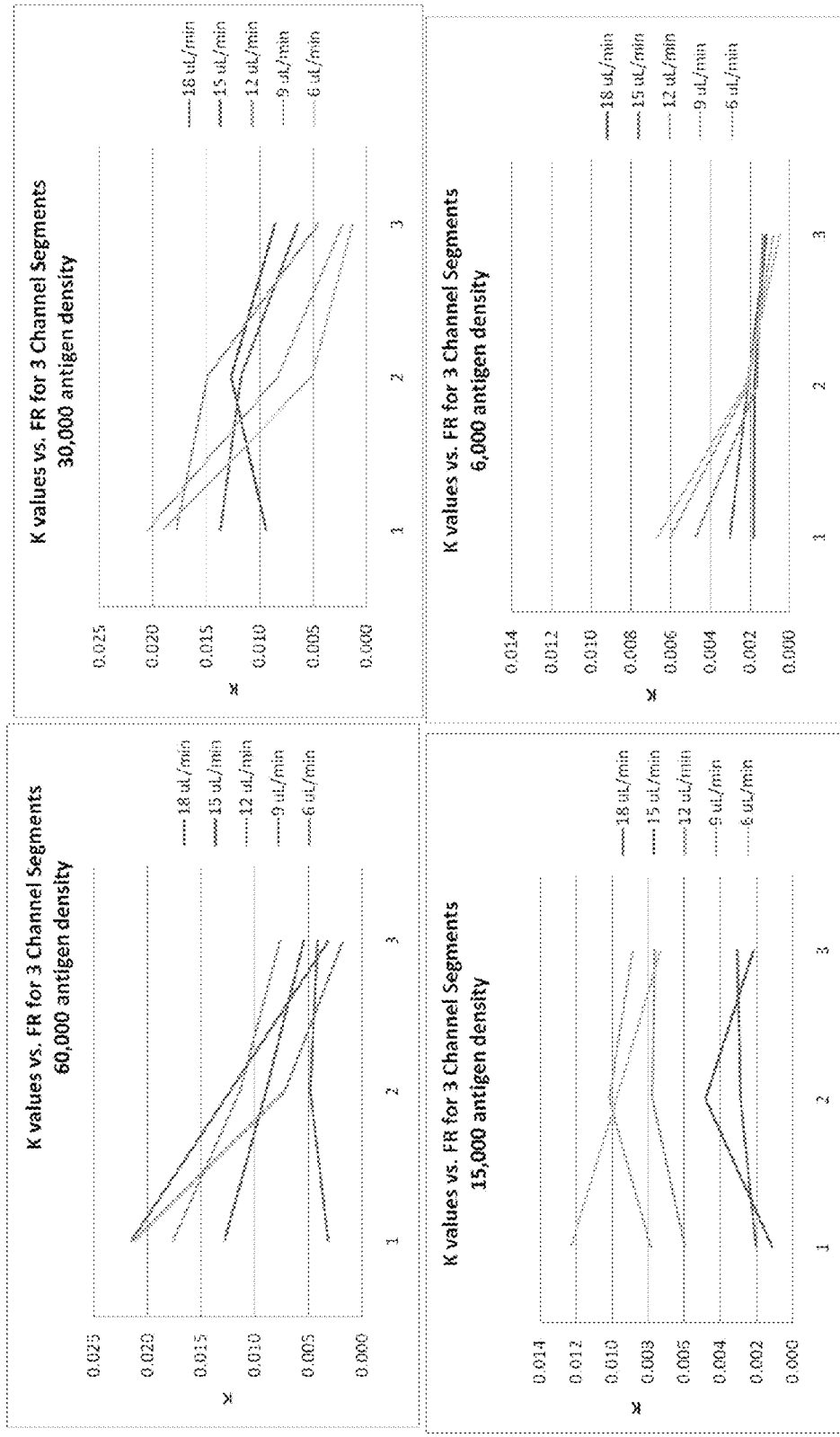
FIG. 23 shows k values as calculated for each channel segment. Series represents various flow rates. Data shows that in low flow-rate regimes, many of the k values decrease as cells travel along the channel. k values vs. channel segment at various flow rates, plotted for four different effective antigen densities: (a) 60 000, (b) 30 000, (c) 15.
Figure 24:
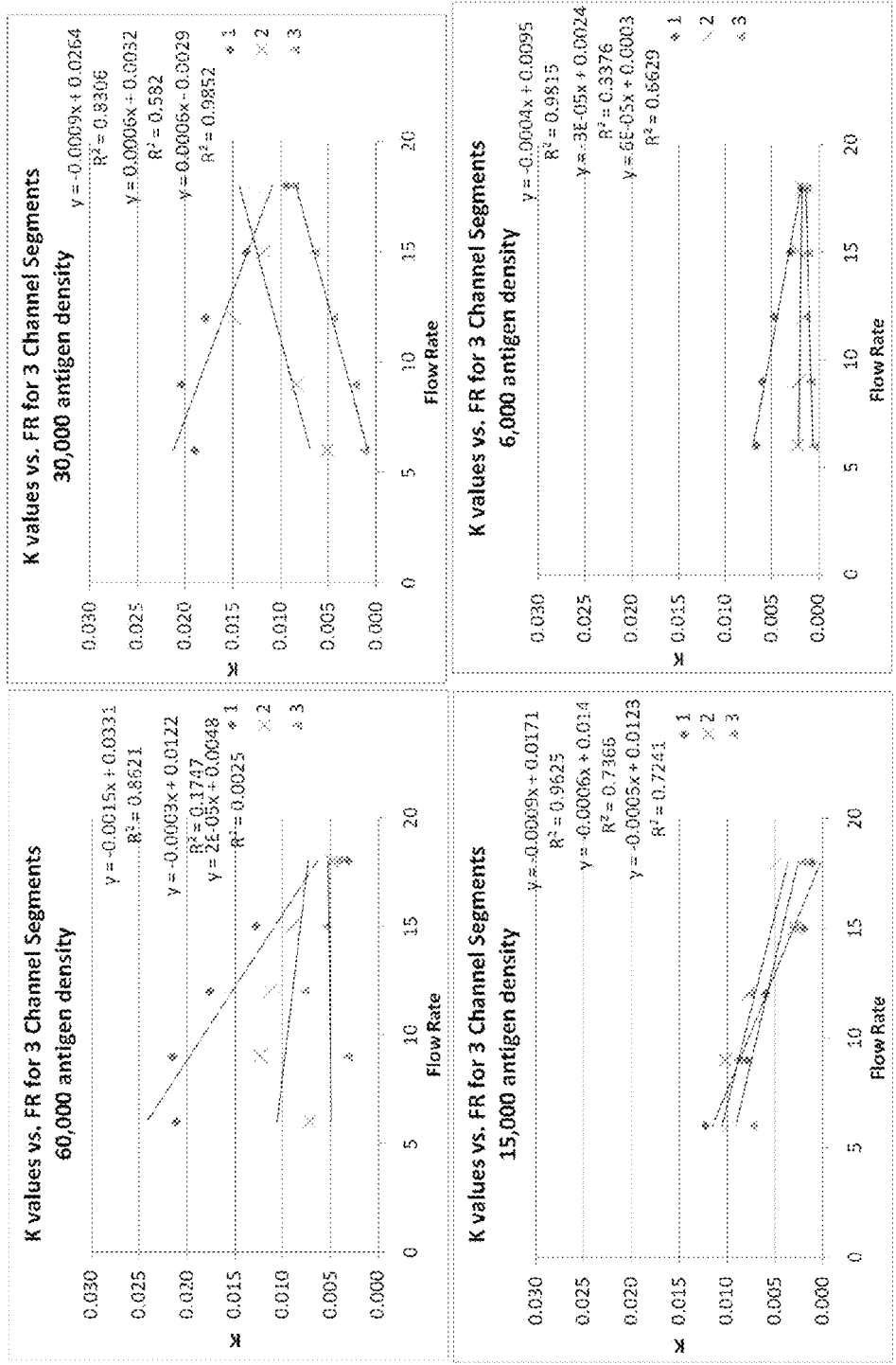
FIG. 24 shows k values as calculated for each flow rate. Series represent each channel zone. Data shows that the entrances of channels in low flow-rate regimes have high k values, while the k values at faster flow rates are lower and remain constant throughout the channel segments. k values vs. flow rate of various channel segments, plotted for four different effective antigen densities: (a) 60 000 (b) 30 000 (c) 15 000, and (d) 6000.
Figure 25:
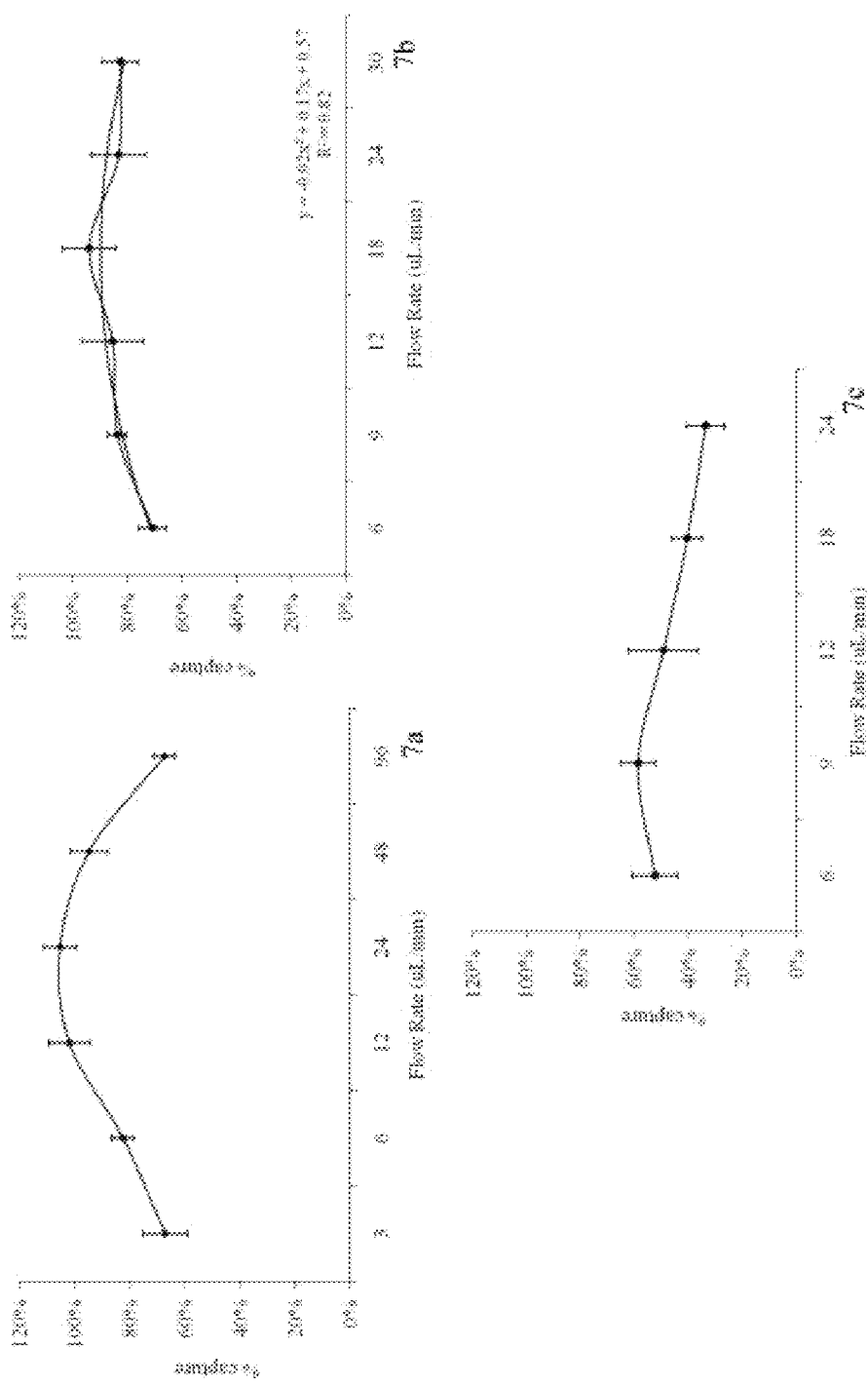
FIG. 25 shows the impact of flow rates upon percent of cells captured in: (a) K562 cells, (b) SKOV cells, and (c) T24 cells.

At each flow-rate, 6, 9, 12, 15, and 18 μL/min, k values are calculated for the three zones along the length of the channel. Decreasing k values indicate a decrease in capture probability as cells travel along the channel. FIG. 23 displays the k values as calculated for each channel segment of SKOV populations with different effective antigen densities. The series represent various flow rates. In low flow-rate regimes, many of the k values decrease as cells travel along the channel. These charts show that for all antigen densities presented, excepting only 15 000, k values in low flow-rate regimes (6-15 μL/min) decrease as cells move through the channel. At the higher flow-rate of 18 μL/min antigen density did not change discernibly along the length of the channel. FIG. 24 shows k values as calculated for each flow rate of SKOV populations with different effective antigen densities. Each channel zone is represented. The entrances of channels in low flow-rate regimes have high k values, while the k values at faster flow rates are lower and remain constant throughout the channel segments.

Figure 26:
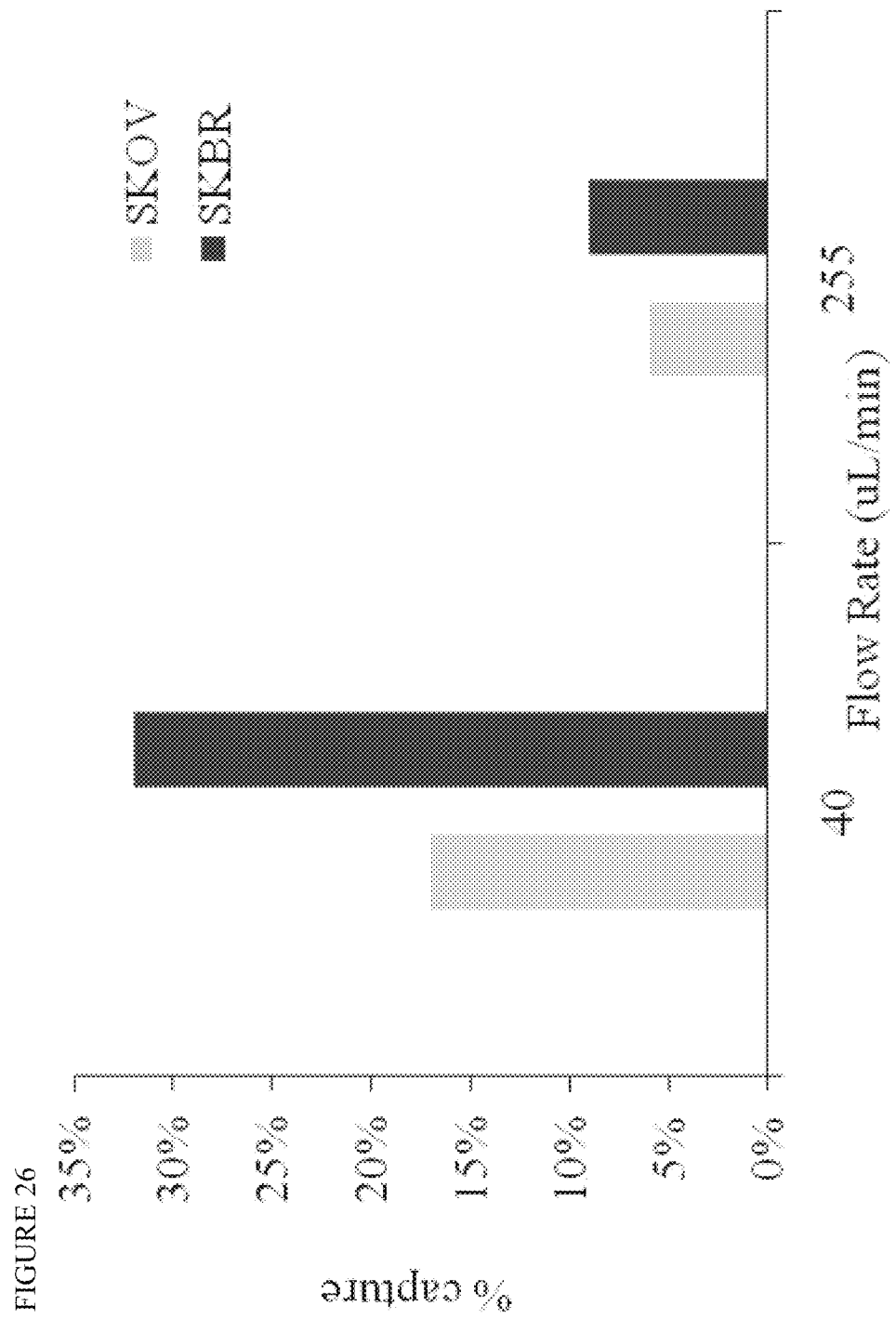
FIG. 26 shows the effect of high flow rate on percentage of SKOV and SKBR cells captured with T2 antigen. Cells not fixed to the posts after capture can be removed from the channel by increasing flow rates.

The maximum flow rate of 18 μL/min was determined from previous experiments with K562, SKOV, and T24 cell lines. K562 were tested with Gly-A, which is over-expressed on these cells to the order of 1×10$^6$ antigens per cells. FIG. 26(*a*) shows how capture varies with flow rate in that cell line, where maximum capture is achieved between 12 and 24 μL/min. The relationship is similar for SKOV cells with EpCAM, FIG. 26*b*, but changes drastically for low-expressing T24 cells with EpCAM, FIG. 26*c*.

The k value dependence on antigen density is likely caused by two effects. First, the chance of a biotin-streptavidin reaction scales with the number of surface ligands per cell. Also, the strength of the cell-post bond should be directly proportional to the number of ligand adhesions occurring as the cell moves past the post, and so should be the force opposing any shear effect. Knowledge of the linear effect of antigen density on capture probability is valuable in determining ideal performance parameters.

FIG. 26 shows the capture of SKOV and SKBR cells with T2 antigen. Cells not fixed to the posts after capture can be removed from the channel by increasing flow rates. More experiments can be done, however, to fully understand the relationship between antigen expression and shear rates.

Variable Antigen Density Results.

All experiments are run at 18 μL/min and trials are run with and without bystander cells as presented in FIGS. 28*a*, 28*b*, in which are shown plots k values for different effective antigen densities, for each channel segment. These data show that k values remain constant along the length of the channel as also observed in variable flow rate experiments. The results show a linear dependence of antigen density upon k as well.

The k value dependence on antigen density is likely caused by two effects. First, the chance of a biotin-streptavidin reaction scales with the number of surface ligands per cell. Also, the strength of the cell-post bond should be directly proportional to the number of ligand adhesions occurring as the cell moves past the post, and so should be the force opposing any shear effect. While it is outside the scope of this experiment to untangle the relative importance of these two effects, knowledge of the linear effect of antigen density on capture probability is valuable in determining ideal performance parameters.

Bystander Cells' Effects on Cell Binding.

Figure 28:
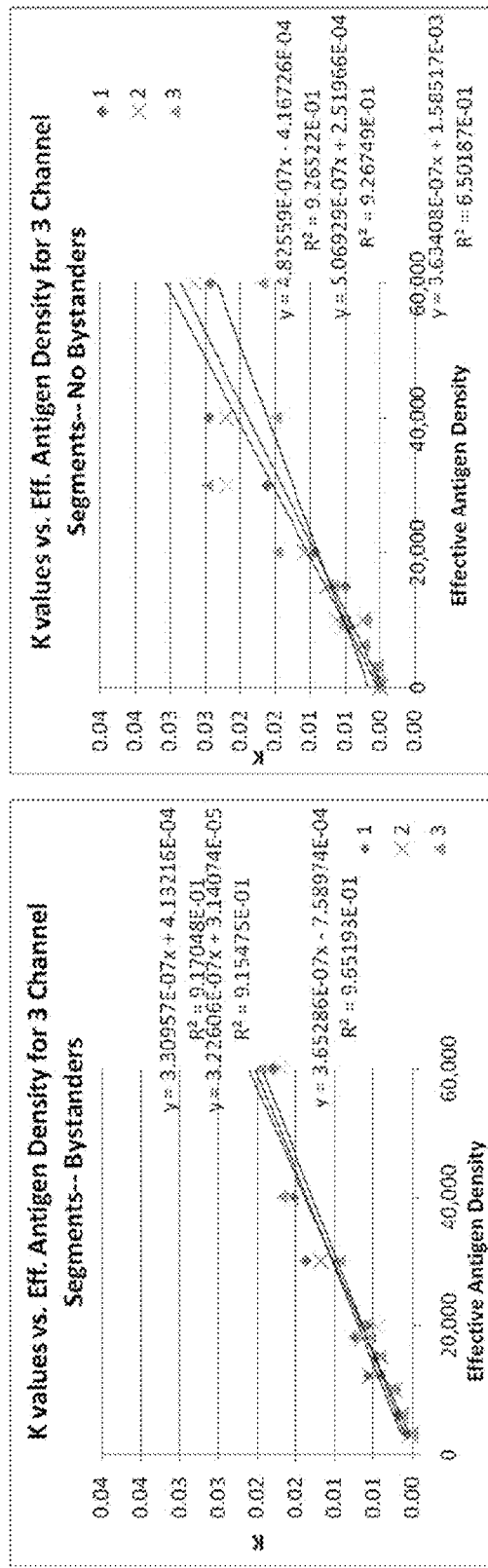
FIG. 28 shows k values plotted for different effective antigen densities. Series represent each channel segment. Data shows that there is a linear relationship between antigen density and capture probability. k value vs. effective antigen density of various channel segments, (a) with and (b) without bystander cells.

As seen in FIG. 28, at the bystander cell concentration studied here and at 18 μL/min, the k values appear to be only slightly lower than the in the control group. Due to the limited studies done with bystander cells, it is difficult to draw general conclusions about how they affect capture efficiency, but they could have contradictory effects: displacing tumor cells from posts, or forcing tumor cells off streamlines and into posts. Further studies would surely be of value.

Figure 27:
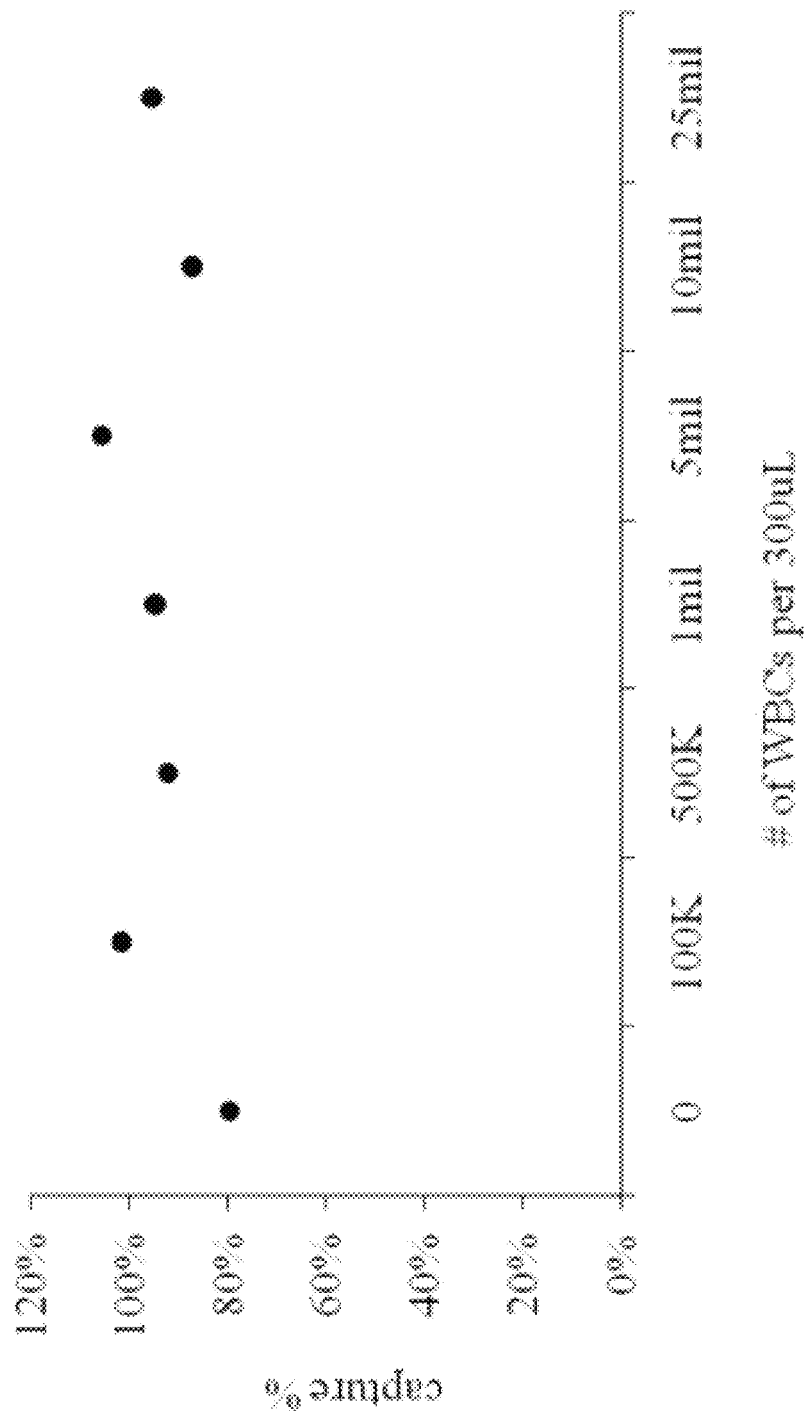
FIG. 27 shows the percent of cells captured as a function of bystander cell concentration.

FIG. 27, which plots concentration of bystander cells against capture of SKOV cells, shows no significant variation.

Decreasing k Values.

If each cell is identical and if each cell is exposed to identical conditions as it zigzags from row to row, the expectation is that the probability of capture will remain constant along the channel. Therefore, the decrease in k observed in most trials indicates heterogeneity. The cell population may be heterogeneous in morphology or surface biotin presentation, or there may be variations in the contact of cells with posts, described above. Both are heterogeneities that cause disposed cells to adhere first, leaving a constantly less disposed population for subsequent adherence, manifesting thus a decreasing k. Different intrinsic tendencies to adhere can be distinguished from bypassing, an extrinsic phenomenon, by how k varies with flow conditions.

As described above a decrease in k with distance is seen in all cases. The data of FIG. 24 add to this view. For cells with high antigen density, the largest k value variation from segment to segment is seen in low flow rate regimes, while there is very little variation at high flow rates. As FIGS. 22*a*, 22*b* show, sensitivity of capture to the density of biotin-labeled antigen is low beyond values of 30,000, which indicates that bypassing may, by default, be the dominant effect that decreases k with increasing distance down the channel.

On the other hand, FIG. 24 shows that k values of low antigen density cells do not vary significantly from segment to segment, no matter the flow rate. As can be seen from FIGS. 22*a*, 22*b*, at low antigen densities, small differences have a large effect on capture. Therefore, the decrease in k along the channel is likely due to heterogeneity of cell populations in this regime.

Whole Blood Experiments.

While preliminary processing of a blood sample by density gradient separation may engender the loss of some smaller or otherwise physically atypical CTC's, the processing of whole blood requires a much larger number of cells to be examined for each antigen-positive CTC that is captured. Gradient-separated cells occupy less than 1 mL. In contrast, the original sample volume of 8-10 mL would require a 7-9 h capture time at the 18 µLmin flowrate discussed in this paper, or a considerably larger capture device, with a concomitant increase in the amount and cost of post-capture reagents. Experiments with high-expression cells (SKBR) and low-expression (SKOV) cells showed high capture only with the former when the antibody was attached to the chamber, but high capture for both types when ligation with soluble biotinylated antibody was followed by capture in a streptavidin-bearing chamber.

Conclusion.

Overall, these data conclude that the CEE system conformed to simple physical principles and it robustly and efficiently captures tumor cells under a variety of operating conditions. The calculation of capture probabilities allows conclusions about the optimal running conditions as well as predictions about the likely capture efficiency of cells given their antigen density to be made.

It appears that there should be a balance between the dominance of cells which follow non-contact streamlines as seen at low flow-rates and the dominance of the obstacles to cell-post binding (such as shear and cell-post contact-time) that are seen at high flow-rates. In this example, maximum consistent capture probability was achieved at a flow-rate of 18 µL/min.

A detailed study of streamlines and subsequently of cell motion relative to these streamlines would aid in design and analysis of cell-capturing channels. Streamline prediction is well within the grasp of computational fluid dynamics and is underway in the inventors' laboratories. These data seem susceptible to combination with established theories that represent cell-cell interactions at higher cell concentrations, and so-called "lift" phenomena that illustrate the tendencies for cells near surfaces to cross streamlines. Actual binding reactions and their dependence on local shear and time have been developed for intravascular phenomena and give a starting point for perfecting models of cell capture in vitro.

While we will have limited knowledge of CTC antigen densities and of the biophysical behavior of endogenous CTC's, knowing how the flow parameters studied here affect capture over a wide range of antigen levels provides basic information of utility to anyone hoping to make a better microfluidic cell-capture system.

There is a clear two step recommendation. First, clinicians should employ antibody cocktails with a common capture principle, here biotin, in order to maximize relevant cell capture (Mikolajczyk, S. D., *J. Oncol.* 2011:252361 (2011)). Second, while the data presented here show that in most cases with sufficient surface antibody density, greater than 70% capture was achieved, a channel design which forces variations in flow velocities along the channel length may overcome potential inefficiencies in capture seen at low antigen densities.

Example 14. FISH-Based Determination of HER2 Status in Circulating Tumor Cells Recovered Using the Microfluidic CEE™ Platform Determination of HER2 status in patients with breast cancer is considered standard practice for selection of treatment options. Traditional methods of monitoring HER2 status include both immunohistochemistry (IHC) and fluorescent in-situ hybridization (FISH) performed on primary tumor tissue. Moreover, patients presenting with recurrent and/or metastatic disease are often re-evaluated for HER2. However, since biopsy is not feasible in many of these patients, circulating tumor cells (CTCs) are an attractive alternative source of tumor tissue for determining HER2 status to enable a more effective course of treatment.

54 patients diagnosed with late stage metastatic/recurrent breast cancer were enrolled from June 2010 to November 2010. Twenty to thirty mL of peripheral blood was collected prospectively and CTCs isolated using the Biocept CEE™ platform to assess reliability of the OncoCEE-BR™ assay to determine HER2 status. CTC capture was achieved using a cocktail of capture antibodies with the microfluidic CEE™ platform, followed by detection using an expanded fluorescent anti-cytokeratin (CK) cocktail mixture and anti-CD45. HER2 amplification was subsequently assessed by FISH on captured CK+/CD45− and CK−/CD45− cells.

CK+/CD45− cells were detected in 43 of 54 cases (80%). Among the 43 clinical cases in which CK+ cells were detected, high concordance (93%) in HER2 status between primary tumor (by IHC and FISH) and CTCs (by FISH) was observed. An overall sensitivity of 95% and a specificity of 92% were obtained using the OncoCEE-BR™ assay.

Recovery of CTCs from peripheral blood using the CEE™ platform is shown to be efficient and suitable for FISH-based testing. In addition, HER2 FISH on recovered CTCs is proven to be sensitive and accurate, permitting incorporation into standardized CLIA-laboratory testing.

Breast cancer (BC) is a heterogeneous disease, encompassing a number of distinct biological entities that are associated with specific morphological and immunohistochemical features and clinical behavior. The only way to classify invasive breast carcinomas for many decades has been based on histological type, grade, and expression of hormone receptors (Lacroix, M., et al., *Endocr Relat Cancer*, 11(3):497-522 (2004); Elston, C. W. and I. O. Ellis. *Histopathology*, 19(5):403-10 (1991); Todd, J. H., et al. Br J Cancer, 56(4):489-92 (1987); and Pereira, H., et al., *Histopathology*, 27(3):219-26 (1995)). More recently, following the success of the trastuzumab adjuvant clinical trials, characterization of HER2 expression has become an integral part of the pathological work-up for breast cancer patients. Oncologists categorize BC patients into three main groups: (i) those whose tumors that exhibit the presence of hormone (estrogen and progesterone) receptors who are subsequently managed with various estrogen receptor (ER) targeted therapies±chemotherapy; (ii) those with HER2 positive tumors (HER2+), in which amplification of the HER2 gene is demonstrated, and who will receive the HER2-directed monoclonal antibody trastuzumab or, in some situations, lapatinib (a dual tyrosine kinase inhibitor targeting HER2 and EGFR); and (iii) those with tumors that do not show evidence of either (i) or (ii) above, otherwise referred to as triple negative (negative for ER, PR, and HER2), for whom chemotherapy is often the only therapy available (Reis-Filho, J. S. and A. N. Tutt. *Histopathology*, 52(1):108-18 (2008)).

With BC, if the cancer recurs, enlarges, or spreads while the patient is on a given therapy, that therapy is often stopped and possibly altered. This is because the tumor may have changed its hormone receptor and/or HER2 status (e.g., HER2-negative tumors can transform/progress to positive status over the course of treatment in response to the selective pressure of the treatment, and as a result of clonal expansion). Selection of subsequent therapies is again dictated by HER2 and ER/PR status, indicating the need to frequently retest patients/tumors for such changes.

The presence of circulating tumor cells (CTCs) in peripheral blood of breast cancer patients has long been associated with metastasis and poor survival (Cristofanilli, M., et al., *N Engl J Med*, 351(8):781-91 (2004); Cristofanilli, M., et al.,

*J Clin Oncol,* 23(7): p. 1420-30 (2005); and Fehm, T., et al., *Clin Cancer Res,* 8(7):2073-84 (2002)). Though CTCs may serve as a surrogate for metastatic tumor tissue and offer an opportunity to perform tumor-based correlative studies without subjecting patients to the risk of serial biopsies (Reis-Filho, J. S. and A. N. Tutt, *Histopathology,* 52(1):108-18 (2008); Cristofanilli, M., et al., *N Engl J Med,* 351(8):781-91 (2004); Scher, H. I., et al., *Lancet Oncol,* 10(3):233-9 (2009); Nagrath, S., et al., *Nature,* 450(7173):1235-9 (2007); and Hayes, D. F., et al., *Clin Cancer Res,* 12(14 Pt 1):4218-24 (2006)), studying them has been challenging due to their extreme rarity in comparison to hematologic cells (about 1 tumor cell per 1 billion blood cells). While technical advances have made it possible for the detection of CTCs in whole blood, current techniques are limited in their capture efficiency and the ability to allow detailed phenotypic and genotypic evaluation of the CTCs (Paterlini-Brechot, P. and N. L. Benali, *Cancer Lett,* 253(2):180-204 (2007)). In fact, the commercially available CellSearch® CTC Test (Veridex LLC, North Raritan, N.J.) has permitted detection of CTCs in blood of patients with metastatic disease (Cristofanilli, M., et al., *N Engl J Med,* 351(8): p. 781-91 (2004); Cristofanilli, M., et al., *J Clin Oncol,* 23(7):1420-30 (2005); Hayes, D. F., et al., *Clin Cancer Res,* 12(14 Pt 1):4218-24 (2006); and Meng, S., et al., *Clin Cancer Res,* 10(24):8152-62 (2004)), with only an overall informative frequency (positive detection of CTCs) of less than 40-50% (Allard, W. J., et al., *Clin Cancer Res,* 10(20):6897-904 (2004)). In addition, flexibility in staining to improve detection and post-enumeration molecular analysis are limited with this platform (Hayes, D. F., et al., *Clin Cancer Res,* 12(14 Pt 1):4218-24 (2006)).

To allow more comprehensive and sensitive means of clinically utilizing CTCs, there remains a need for a methodology that can efficiently capture, enrich, and subsequently improve the detection rates of CTCs in blood. In this prospective study, we report the utility of a microfluidic platform that utilizes CEE™ (cell enrichment and extraction technology; Biocept Inc., San Diego, Calif.) for capture, enrichment, and subsequent molecular evaluation of HER2 amplification status in CTCs by fluorescent in situ hybridization (FISH). Using peripheral blood from women with metastatic/recurrent or late stage breast cancer, we tested analytical sensitivity of a CTC HER2 FISH-based test using OncoCEE-BR™ as compared to patient matched primary tumor.

Patients with advanced stage breast cancer were enrolled from June 2010 to November 2010. Peripheral blood was collected under appropriate third party institution review board approved protocols. Twenty-thirty mL blood was collected from 54 patients into 8.5 mL ACD vacutainer tubes (acid-citrate-dextrose solution A; BD, Franklin Lakes, N.J.) followed by the immediate injection of an anti-clumping reagent (CEE-Sure™, Biocept Inc., San Diego, Calif.) directly into the vacutainer tubes. Samples were stored at room temperature and processed within 24 hours of collection at Biocept's CLIA/CAP accredited laboratory. Control blood from normal donors (n=5) was obtained and used to demonstrate sensitivity/specificity of the HER2/17 probe set on normal interphase cells.

Leucosep tubes (Greiner bio-one, Monroe, N.C.) utilizing a Percoll density gradient method were used to recover the peripheral blood mononuclear cell fraction (PBMC) fraction. Fc blocker (100 µg/mL) and a capture antibody cocktail (1 µg/mL of each antibody in the cocktail: EpCAM and Trop-2, (BD Biosicences, San Diego, Calif.); c-Met and Folate binding protein receptor, (R&D Systems, Minneapolis, Minn.); N-Cadherin, (Sigma-Aldrich, St Louis, Mo.); CD318, MSC and Her2, (BioLegend, San Diego, Calif.); Muc-1 (Fitzgerald, Acton, Mass.); EGFR (Santa Cruz Biotechnology, Santa Cruz, Calif.)) were added for 30 minutes at room temperature to the recovered PBMC fraction. Following a wash and centrifugation, secondary antibody was added for 30 minutes at room temperature. Cell suspension was washed three times with PBS/Casein/Arginine/EDTA with centrifugation at 400 G for 10 minutes. The final pellets were subsequently captured onto the CEE™ microchannels.

Cell enrichment and extraction technology (CEE™) microchannels are manufactured at Biocept, Inc. (San Diego, Calif.). Each microchannel consists of a roughly rectangular chamber (40 mm×12 mm×55 microns) in which approximately 9000 variable diameter posts are strategically placed to disrupt laminar flow, and maximize the probability of contact between target cells and the posts, which are derivatized with streptavidin, resulting in their capture. Each microchannel is attached to a specially designed holding rack (Biocept Inc., San Diego, Calif.) which stabilizes the channels and maintains them at a 45 degree angle. Microchannels are attached via Teflon tubing which links the outlet of the microchannel directly to radially arranged syringes controlled by a pump (Biocept, Inc., San Diego, Calif.). The carefully calibrated and locked central barrel of the pump is set to pull equally on all syringes simultaneously allowing for uniform entry of all samples or reagents into the microchannels. The microchannels are flushed twice with storage buffer (PBS/BSA/EDTA) and once with running buffer (1×PBS/1× Casein/5 mM EDTA/100 mM Arginine; Casein/Arginine buffer) at a high flow rate of 150 µL/min prior to the addition of the cell fraction (isolated during cell separation with the capture antibody cocktail) into the microchannel.

The CEE™ microchannel platform is extremely versatile, allowing for easy manipulation of the capture antibodies used, and any immunocytochemistry (ICC) staining antibodies, as well as permitting the direct microscopic analysis of CTCs (ICC or FISH). The cell fraction is run through the microchannel and then stained with antibodies for a mixture of cytokeratins (CK; antibodies against cytokeratins 4, 5, 6, 7, 8, 10, 13, 17, 18 and 19) directly tagged with Alexa-488, and CD45 labeled with Alexa-594. The microchannels undergo manual microscopic analysis for enumeration of CK+/CD45−/DAPI+ (criteria for CTC identification), CK−/CD45+/DAPI+ (criteria for background white blood cells) and CK−/CD45−/DAPI+ (possible CTCs that lack CK) cells, with images and X/Y coordinates recorded using Olympus Bx51 fluorescent microscopes equipped with appropriate filters and the FISH imaging system v5.2 (Metasystems GmbH, Germany).

Following CTC enumeration, the CEE microchannels were processed for multi-color FISH using the FDA-approved PathVysion HER-2 DNA Probe Kit (centromere 17 specific probe; CEP 17—Spectrum Green, and locus specific HER2 probe; Spectrum Orange) and a centromere specific probe to chromosome 8 (CEP 8—Spectrum Aqua, Abbott Molecular, Abbott Park, Ill.) for use as an internal control for ploidy status. Evaluation of FISH signal patterns was performed on both CK+/CD45− and CK−/CD45− CTC populations. The ratio of HER2:CEP 17 was calculated and a ratio >2.2 in any CD45 negative CK+ or CK− cell was regarded as positive for HER2 gene amplification.

To assess the analytical performance of HER2 amplification by FISH, we calculated the sensitivity, specificity, positive predictive value, and negative predictive value for the patients involved in this study. Pearson's correlation coefficient was calculated to determine the degree of correlation between blood samples from the same patient. Cohen's kappa statistic was also calculated to adjust for chance in order to assess the agreement of HER2 status between the primary tumor and CTCs (Landis, J. R. and G. G. Koch, *Biometrics*, 33(1):159-74 (1977)).

A total of 54 peripheral blood samples were collected and processed for CTC enumeration and HER2 FISH characterization between June and November 2010. Patient characteristics are shown in Table 7 (patient characteristics). These samples were from late stage IV metastatic or recurrent breast cancer patients sourced through vendors under third party consent. Following enumeration, 43 patients were found to have ≥1 CTC identified based on a staining pattern of CK+/CD45-negative cells (prevalence 80% based on CK+ staining) Additional cells were noted to be candidate CTCs based on CK-negative/CD45-negative staining pattern; these cells failed to stain positive for CD45 and therefore classified as possible CTCs that may have down regulated CK expression. XY coordinates and images were taken of these cells for subsequent re-location and FISH analysis. The average number of CTCs isolated from peripheral blood was 1.33 per 1 ml (sample range, 1-316). HER2 amplification was not observed among normal blood lymphocytes (n=2500) obtained from normal non-cancer controls.

TABLE 7

| Characteristic, n (%) | All Patients N = 54 | Patients with ≥1 CTC in 10 mL of Blood (n = 43) |
|---|---|---|
| Median Age, Years (Range) | | 64 (29-86) |
| CTCs based on CK+ | | |
| 0 | | 11 (20) |
| 1-4 | | 15 (28) |
| 5-9 | | 9 (17) |
| ≥20 | | 19 (35) |
| HER2+ | 24 (44) | 20 (47) |
| HER2− | 30 (56) | 23 (53) |
| ER+/PgR+ | 31 (57) | 26 (60) |
| ER+/PgR− | 13 (24) | 10 (23) |
| ER−/PgR− | 10 (19) | 8 (19) |

Figure 29:
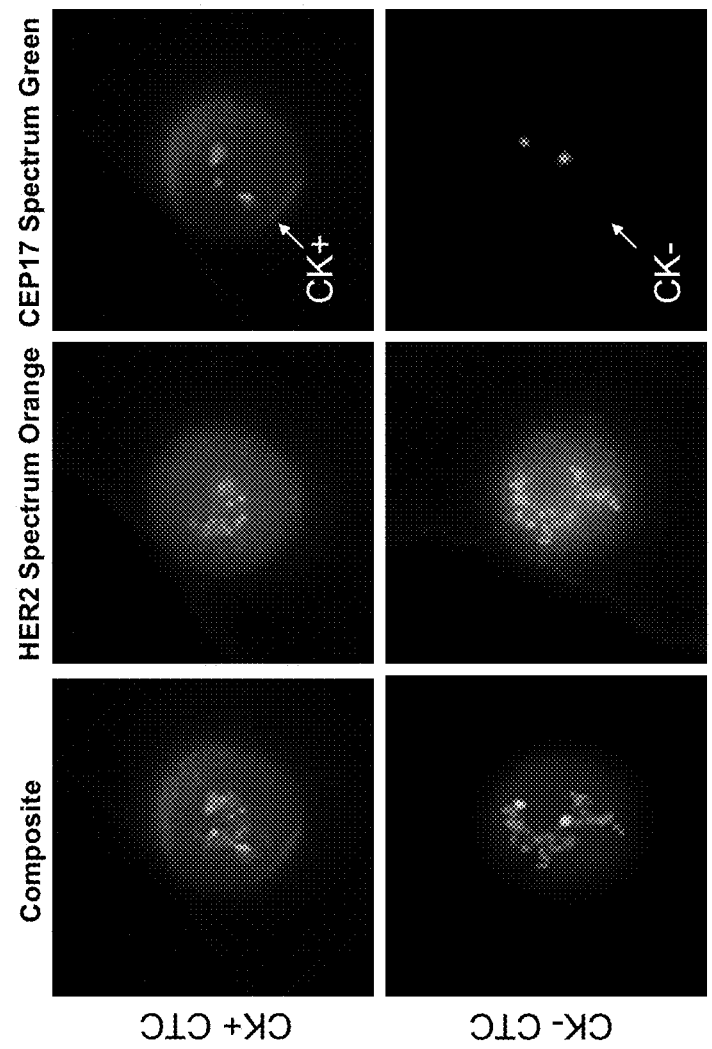
FIG. 29 shows representative images of HER2 amplified cells using the Pathvysion probe set. Top panels demonstrate HER2 amplification (Spectrum Orange) compared to centromere 17 (CEP17; Spectrum Green) in a CK+ cell (arrow indicates Alexa488 green staining). Bottom images demonstrate HER2 amplification (Spectrum Orange) compared to centromere 17 (CEP17; Spectrum Green) in a CK-negative cell (arrow).

Abbreviations:
CK = cytokeratin;
CTC = circulating tumor cell;
ER = estrogen receptor;
N = node;
PgR = progesterone receptor Concordance of HER2 Status. Among the 43 CK+ informative cases, an overall concordance of 93% was observed with regards to HER2 status. Concordance was observed in 18 of 19 cases with positive HER2 status (positive predictive value of 90%) and 22 of 24 cases with negative HER2 status (negative predictive value of 96%). Discordance was observed in three cases as shown in Table 7. One patient with positive HER2 amplification in the primary tumor displayed HER2 negative CTCs in the CEE™ microchannel and two patients with HER2 positive CTCs had a primary tumor classified as HER2 negative. An overall test sensitivity of 95% and specificity of 92% was observed. A substantial agreement approaching the range of perfect agreement (0.81-1.00) was found using the Cohen's κ statistic (κ=0.75) for concordance between HER2 status in the primary tumor and CTCs. A high degree of correlation was found between blood samples from the same patient as calculated by Pearson's correlation coefficient (r=0.95) with a 95% confidence interval (CI; 0.9067<=r>=0.9679). However, an important observation was made during the course of this study, which is that HER2 amplified cells enriched using the CEE™ platform were both CK+ and CK-negative. (FIG. 29). Thus, FISH detection of CTCs based on chromosomal content is feasible following enrichment and capture using CEE™.

TABLE 8

| Primary Tumor | CTCs, n (%) | | |
|---|---|---|---|
| | HER2− | HER2+ | Total, n |
| HER2− | 22 (51) | 2 (5) | 24 |
| HER2+ | 1 (2) | 18 (42) | 19 |
| Total | 23 (53) | 20 (47) | 43 |

Abbreviation:
CTC = circulating tumor cell

Table 8 shows the concordance of HER2 status between CTCs isolated using the OncoCEE-BR™ and primary tumor.

Many studies have reported the identification and characterization of mutations that occur frequently during breast tumorigenesis including the overexpression and amplification of the human epidermal growth factor receptor 2 (HER2/neu, CERBB2) (Bieche, I. and R. Lidereau, *Genes Chromosomes Cancer*, 14(4): p. 227-51 (1995); Iglehart, J. D., et al., *Cancer Res*, 50(20): p. 6701-7 (1990); Lacroix, H., et al., *Oncogene*, 4(2):145-51 (1989); Simon, R., et al., *J Natl Cancer Inst*, 93(15):1141-6 (2001); and Slamon, D. J., et al., *Science*, 235(4785):177-82 (1987)). HER2 status is now widely recognized as an important marker for aggressiveness and as such patients that exhibit overexpression and amplification are treated with the US Food and Drug Administration (FDA) approved humanized monoclonal antibody trastuzumab (Herceptin; Genentech, San Francisco, Calif.) (Sauter, G., et al., *J Clin Oncol*, 27(8):1323-33 (2009)). While HER2 status determined by FISH and immunohistochemistry (IHC) are correlated, current ASCO-CAP (American Society of Clinical Oncology-College of American Pathologists) guidelines recommend FISH for accuracy, reproducibility and precision (Sauter, G., et al., *J Clin Oncol*, 27(8):1323-33 (2009)). Furthermore, several investigators have recently reported that the status of HER2 can vary from the primary tumor to the metastatic site, as well as in CTCs. Therefore, monitoring the status of HER2 in CTCs becomes a viable option and can be viewed as a liquid biopsy during the course of treatment (Cristofanilli, M., et al., N Engl J Med, 351(8):781-91 (2004); Scher, H. I., et al., *Lancet Oncol*, 10(3):233-9 (2009)). A recent study by Nagrath et al. strongly suggests a microfluidic-based platform to be a more sensitive and specific approach for CTC recovery based on only EpCAM and CK selection criteria with positive correlation between CTC numbers and clinical course of disease as measured by standard radiographic methods (Nagrath, S., et al., *Nature*, 450(7173):1235-9 (2007)). Though similar, the CEE™ platform utilizes an antibody cocktail to enable capture of more heterogeneous tumor cell populations based on subsequent FISH analysis of HER2 in CK+ and CK− cells. We observed HER2 amplification in both CK+/CD45− and CK−/CD45− cells; demonstrating detection of both robust epithelial CK+ CTCs as wells as CTCs that have presumably down-regulated CK expression below visible detection levels. Thus, studies that are limited to use of EpCAM and CK for capture/enrichment and detection, respectively, will not observe sufficient concordance between CTCs and primary tumor. Though some discordance between tumor and CTCs is perhaps expected given tumor heterogeneity, biopsy size and robustness of the technical assay (i.e. IHC), a blood based CTC assay offers more reliable testing given the advantage of repeated testing and draw of higher blood volumes when needed to ensure informative results. We show that FISH offers a highly sensitive and accurate approach for identifying cytogenetically abnormal cells likely to be of tumor origin.

Clinically, CTCs have been demonstrated to provide measurable prognostic value for advanced breast cancer patients (Cristofanilli, M., et al., *N Engl J Med*, 351(8):781-91 (2004) and Cristofanilli, M., et al., *J Clin Oncol*, 23(7): p. 1420-30 (2005)). In the present study we report the utility of a microfluidic platform that utilizes the CEE™ technology (Biocept, Inc., San Diego, Calif.) for capture, enrichment and subsequent molecular evaluation of HER2 gene amplification in CTCs by FISH. The CEE™ technology provides a sensitive platform for enhanced capture, detection and characterization of both CK+ positive and negative CTCs. This platform allows for evaluation of HER2 gene amplification status by FISH in intact CTCs within the microchannels at sensitivity and accuracy levels suitable for standardized CLIA-laboratory testing. The clinical utility of this platform for phenotypic and genotypic characterization of CTCs in breast cancer needs to be tested in larger clinical trials.

Example 15. Detection of EpCAM-Negative and Cytokeratin-Negative Circulating Tumor Cells in Peripheral Blood Enrichment of rare circulating tumor cells (CTCs) in blood is typically achieved using anti-epithelial cell adhesion molecule (EpCAM), with detection using anti-cytokeratin (CK). However, EpCAM and CK are not expressed in some tumors, and can be down-regulated during epithelial-to-mesenchymal transition. A micro-fluidic system, not limited to EpCAM or CK, was developed to use multiple antibodies for capture followed by detection using CEE-Enhanced™ (CE), a novel in situ staining method that fluorescently labels the capture antibodies bound to CTCs. Higher recovery of CTCs was demonstrated using antibody mixtures compared to anti-EpCAM. In addition, CK-positive breast cancer cells were found in 15 of 24 samples (63%; range 1-60 CTCs) while all samples contained additional CE-positive cells (range 1-41; median=11; p=0.02). Thus, antibody mixtures against a range of cell surface antigens enables capture of more CTCs than anti-EpCAM alone and CE staining enables the detection of CK-negative CTCs.

In order to analyze rare CTCs in the blood of cancer patients, it is necessary to enrich, isolate and identify the tumor cells in the presence of billions of red blood cells and the tens of millions of nucleated hematopoietic cells. The most commonly used form of enrichment relies on antibodies against the epithelial cell adhesion molecule, EpCAM (Fehm T, et al., *Cytotherapy*. 7:171-85 (2005); Paterlini-Brechot P, Benali N L. *Cancer Lett*. 253:180-204 (2007)). The FDA-approved CellSearch system has set the standard for the use of EpCAM in the enrichment of CTCs using a magnetic ferro-fluid approach (Allard W J, et al., *Clin Cancer Res*. 10:6897-904 (2004); and Riethdorf S, et al., *Clin Cancer Res*. 13:920-8 (2007)). EpCAM is also used as a main capture component in other immuno-magnetic bead-based systems as well as microfluidic systems (Allan A L, Keeney M. *J Oncol*. 2010:1-11 (2010); Nagrath S, et al., *Nature*. 450:1235-9 (2007); Fehm T, et al., *Breast Cancer Res*. 11:R59 (2009)). Other emerging approaches do not depend on immuo-enrichment at all but instead use precise size filters to separate larger epithelial cells from smaller RBC and WBC (Hofman V, et al., *Clin Cancer Res*. 10.1158/1078-0432.CCR-10-0445 (2010)). Alternatively, approaches using only cell lysis to remove interfering RBC have been described (Marrinucci D, et al., *J Oncol*. 2010:861341 (2010); Camara O, et al., *J Can Res Clin Oncol*. 135:643-7 (2008)). In this case all remaining nucleated cells are layered onto several slides for further analysis. PCR-based systems do not enumerate based on visual cell detection but still use immuno-magnetic beads for enrichment and EpCAM markers, among others, for enrichment and detection (Fehm T, et al., *Breast Cancer Res*. 2009; 11:R59; Fehm T, et al., *Breast Cancer Res*. 2007; 9:R74; Helo P, et al., *Clin Chem*. 55:765-73 (2009)). Regardless of the system used for isolation or enrichment, detection almost always relies on staining for cells containing cytokeratin, an internal architectural protein that is largely associated with epithelial cells (Moll R, et al., *Histochem Cell Biol*. 129:705-33 (2008)). Most healthy control blood contains few or no CK-positive cells (Allard W J, et al., *Clin Cancer Res*. 10:6897-904 (2004)). Counterstaining with anti-CD45 is employed to rule out occasional nucleated white blood cells (WBC) that stain for CK. In those cases where EpCAM has not been used for enrichment, such as the RBC lysis approach, EpCAM can alternatively be used for detection (Camara O, et al., *J Can Res Clin Oncol*. 135:643-7 (2008); Pachmann K, et al., *J Can Res Clin Oncol*. 10.1007/s00432-010-0942-4 (2010)). PCR approaches generally use some combination of EpCAM or CK for enrichment or detection (Helo P, et al., *Clin Chem*. 55:765-73 (2009); Shaffer D R, et al., *Clin Cancer Res*. 13:2023-9 (2007) and Schroeder C P, et al. *Intl J Cancer*. 106:611-8 (2003)). Overall, there is a high dependence on just two epithelial markers for capture and/or detection of CTCs.

Based on the above criteria, it is implicitly understood that detection of CTCs is actually detecting circulating epithelial cells that are typically not present in blood and assumed to be tumor-associated. The description that all CK and/or EPCAM positive cells (that are by definition not CD45-positive) are CTCs has become axiomatic in the field since a number of studies using CellSearch have shown a good correlation between the numbers of these circulating CK-positive/EpCAM-positive cells and prognosis for cancer survival (de Bono J S, et al., *Clin Cancer Res*. 14:6302-9 (2008); Scher H I, et al., *Lancet Oncol*. 10:233-9 (2009)). There is also considerable evidence that some of the CK-positive cells contain cancer cytogenetic markers such as TMPRSS2-ERG, MYC, PTEN and Her2/neu (Attard G, et al., *Cancer Res*. 69:2912-8 (2009); Lilja H, et al., *Clin Chem*. 56:1375-7 (2010); Leversha M A, et al., *Clin Cancer Res*. 15:2091-7 (2009); and Pestrin M, Bessi S, Galardi F, Truglia M, Biggeri A, Biagioni C, Cappadona S, Biganzoli L, Giannini A, Di Leo A. Correlation of HER2 status between primary tumors and corresponding circulating tumor cells in advanced breast cancer patients. *Breast Cancer Res Treat*. 118:523-30 (2009)). The success in correlating CTC enumeration with patient survival has conferred a dependence on EpCAM and CK to virtually every other system. This has also imposed a clear bias on the study of CTCs, primarily the failure to include tumor cells that have reduced or absent CK and/or EpCAM. The failure to identify such cells limits investigations into additional tumor types.

EpCAM is expressed in most but not all tumors (Went P T, et al., *Hum Pathol*. 35:122-8 (2004)). There is evidence for upregulation and downregulation of EpCAM with cancer progression and metastasis, and it is likely that both are true, depending on the type and stage of cancer and other biological variables (Spizzo G, et al., Breast Cancer Res Treat. 86:207-13 (2004) and Tai K Y, et al., Oncogene. 26:3989-97 (2007)). CK is heterogeneously expressed in tissues, and may be downregulated or secreted (Alix-Panabiéres C, et al., Breast Cancer Res. 2009; 11:R39 and Woelfle U, et al. Clin Cancer Res. 10:2670-4 (2004)). During the progression of EMT both EpCAM and CK are downregulated as part of a pathway to increased invasiveness and metatstatic potential (Paterlini-Brechot P, Benali N L. Cancer Lett. 253:180-204 (2007)). EpCAM may be downregulated to allow epithelial cell dissociation from the tumor, and the structural cytoplasmic CK is downregulated to facilitate cell plasticity and migration.

Given the potential range of genotypic etiology it may be difficult to predict the predominant phenotype of any given CTC in a sample. Significant phenotypic heterogeneity may exist between samples, or even among the cells in a single sample. And yet the field has been slow to progress beyond the simple EpCAM capture, CK detection model because there is no clear alternative. In order to extend the range of possible tumor cell enrichment it is necessary to have a system with greater flexibility to enrich and detect additional types of CTCs.

In this example we describe a platform that can be used to simultaneously capture multiple tumor cell types by employing mixtures of antibodies that may include, but are not solely dependent on, EpCAM. In addition, we describe a novel universal staining method, CEE-Enhanced™ that can selectively detect tumor cells that have been targeted by the capture antibodies, regardless of their phenotypic expression of other known cancer markers.

Blood Collection.

Blood samples from cancer patients were obtained from Conversant Biologics Inc., Huntsville, Ala. All samples were collected using an IRB approved protocol and informed consent. As controls, healthy donors who had no history of cancer also provided consent prior to participation. Blood samples were collected into 10-mL Vacutainer tubes containing 1.5 mL acid-citrate-dextrose (ACD Solution A Vacutainers; Becton, Dickinson and Company, Franklin Lakes, N.J.). Within 60 minutes of blood collection, the addition of 250 µL of anti-clumping reagent (Cell-Sure™; Biocept, San Diego, Calif.) was injected into each tube before being shipped to Biocept for processing within 24 hours of collection. Samples were stored at room temperature (RT) before processing.

Blood Sample Processing.

Blood samples were initially processed for recovery of peripheral blood mononuclear cells by using a Percoll density gradient method and Leucosep tubes (Greiner Bio-One, Monroe, N.C.). Each Leucosep tube was pre-filled with Percoll Plus (GE Healthcare, Piscataway, N.J.) at a density of 1.083 g/mL (adjusted using normal saline) and stored at RT. Each 10-mL blood sample was diluted three-fold with phosphate-buffered saline (PBS) containing 1 mg/mL casein and 1 mM ethylenediaminetetraacetic acid (EDTA) and poured directly into a Leucosep tube. Samples were centrifuged for 15 minutes at 1000 g at RT in swinging bucket rotors (Allegra X-12R centrifuge; Beckman Coulter, Brea, Calif.), with brakes set to their lowest setting. After centrifugation, the upper layer (above the separation barrier) was decanted through a 70-µm cell strainer into a 50-mL conical tube. The decanted sample volume was adjusted to 45 mL with PBS/casein/EDTA and then centrifuged for 10 minutes at 400 g. Supernatant was removed by aspiration. The pellet was then resuspended and incubated with Fc blocker (100 µg/mL human IgG) and capture antibody cocktail (each antibody adjusted to 1 mg/mL) for 30 minutes at RT. After incubation, the pellet was washed by adjusting the volume to 45 mL with PBS/casein/EDTA and centrifuging for 10 minutes at 400 g at RT. Biotinylated anti-mouse secondary (Jackson Labs, Bar Harbor, Me.) was added to the pellet and after mixing, was incubated for 30 minutes at RT. The resulting pellet was washed three times with PBS/casein/EDTA. Each wash step consisted of centrifugation for 10 minutes at 400 g, followed by supernatant aspiration. The final pellet was suspended in 1 mL PBS/BSA/EDTA and subjected to capture and staining on the CEE™ micro-channel (manufactured at Biocept, Inc, San Diego). Samples were pulled through CEE™ micro-channels with syringe pumps (manufactured at Biocept Inc, San Diego) connected to the outlet at a volumetric flow rate of 18 mL/min. After the entire sample was processed through the channel, cells were cross-linked within CEE™ micro-channels with 2 mM NHS homobifunctional protein cross-linker and fixed with 80% MeOH.

Antibody Mixture.

Unless otherwise specified the antibody mixture contained the following individual antibodies: anti-EpCAM (Trop-1), tumor-associated calcium signal transducer 2 (Trop-2), (BD Biosiceinces, San Diego, Calif.); anti-c-MET (95106), anti-Folate binding protein receptor (MOV18), (R&D Systems, Minneapolis, Minn.); anti-N-Cadherin (GC-4), (Sigma-Aldrich, St Louis, Mo.); anti-CD318 (CUB1), anti-mesenchymal stem cell antigen (W305), anti-Her2 (24D2), (Biolegend, San Diego, Calif.); anti-MUC-1 (M4H2) (Fitzgerald, Acton, Mass.); and anti-EGFR (528) (Santa Cruz Biotechnology, Santa Cruz, Calif.). Each antibody was assessed by flow cytometry (Accuri Cytometers Inc., Ann Arbor, Mich.) for positive signal on multiple cultured cell lines (e.g., SKOV, SKBR3, T24, LNCaP) and for low background on buffy coat cells isolated from control blood.

Micro-Channel and Detection of Captured CTCs on the Micro-Channel.

Figure 30:
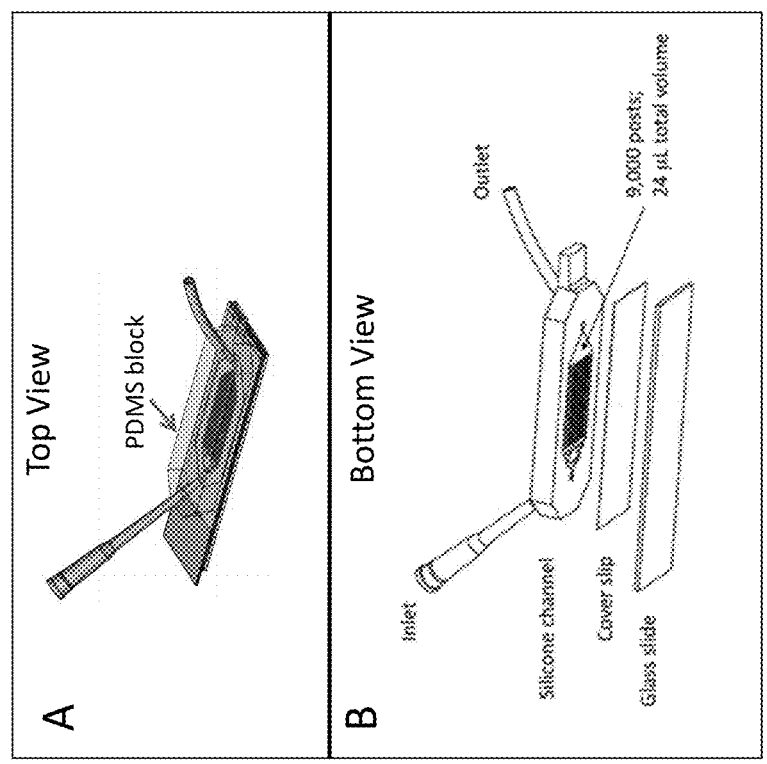
FIG. 30 shows a diagram of the CEE™ micro-channel. 30A. Top view of the channel showing the inlet where sample is loaded and the outlet that is attached to a syringe pump to draw sample through the channel. 30B. Bottom view shows the area where 9,000 posts are located in the PDMS and the channel sealed with the bottom cover slip. The total volume of the micro-channel is 24 mL. The microscope slide is added for stability during handling but is removed to visualize cells. The micro-channel is inverted on a microscope and the captured cells viewed through the coverslip.

CEE™ micro-channel design is illustrated in FIG. 30. The random size and spacing of the posts is mathematically designed to avoid laminar flow through the channel, thus maximizing cell contact with the inner surfaces. The entire inner surface of the channel is derivatized with tethered streptavidin and therefore cells may be specifically bound on any surface. In practice the majority of the CTCs are captured on the posts though some cells are found on the channel floor.

Cells were stained with a mixture of anti-cytokeratin 7/17 (clone C-46), 18 (clone DA/7), 19 (clone A53-B/A2), and pan-cytokeratin (clone C-11) (BioLegend, San Diego, Calif.) antibodies labeled with AlexaFluor-488; CD45 antibody (clone HI30) (BioLegend, San Diego, Calif.) labeled with AlexaFluor-594 for 30 minutes, washed with PBS and stained with DAPI III counterstain. Channels were stored at +8° C. until microscopic analysis. CTC enumeration was performed by analysis through a standard Olympus BX51 fluorescence microscope (Olympus America Inc, Center Valley, Pa.) at 200× magnifications and based on CK+/CD45−/DAPI+ stain criteria. The precise location (X- and Y-stage coordinates) of each CTC was recorded, permitting re-localization of cells after additional staining procedures.

CE staining employed neutravidin labeled with fluorescent probes, including AlexaFluor 488 or 546 as indicated. Following initial scoring and localization of CK+/CD45−/

DAPI+ cells, the captured cells within the micro-channel were then subjected to CE staining whereupon the channels were re-scored to note the locations of the CE-labeled cells as well as to assess presence of CE-stain on the original CK stained cells.

Fluorescence In-Situ Hybridization (FISH).

Figure 36:
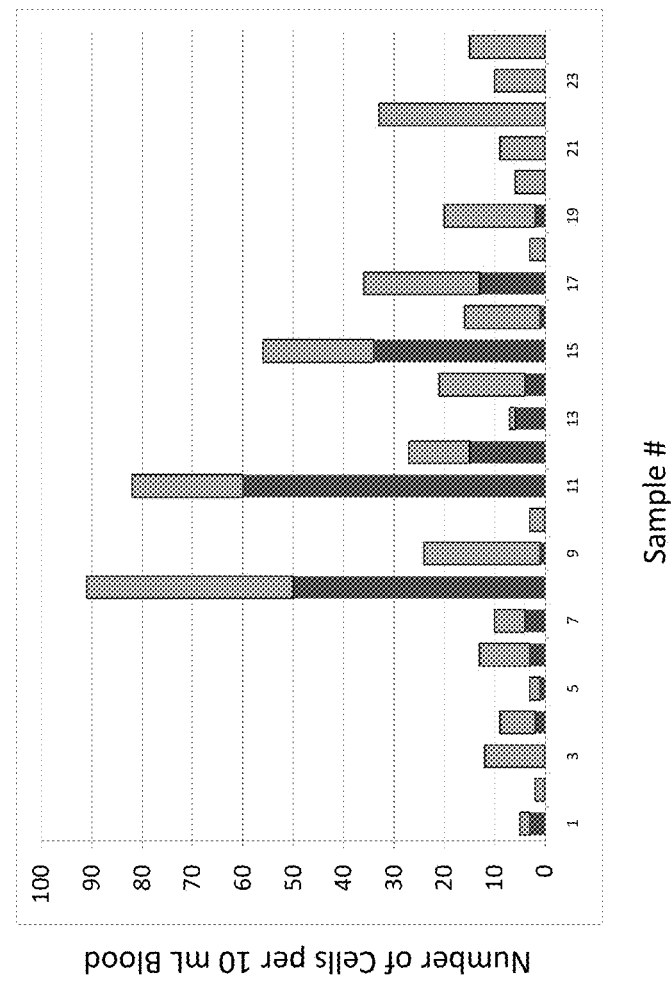
FIG. 36 shows clinical breast cancer samples sequentially stained with anti-CK and with CEE-Enhanced™. The antibody mixture was used to capture CTCs. The dark bars on the bottom represent the number of CK positive cells detected in a sequential series of stage IV breast cancer samples. The location of these cells was recorded and then the channel was re-stained with CE. The light bars on top represent the newly detected CTCs after CE. All cells designated as positive were CD45 negative and DAPI positive.

Following CTC enumeration of the breast cancer samples in FIG. 36, the CEE microchannels were processed for multi-color FISH using the FDA approved PathVysion HER-2 DNA Probe Kit (centromere 17 specific probe (CEP 17—Spectrum Green) and locus specific HER2 probe (Spectrum orange)) and a centromere specific probe to chromosome 8 (CEP 8—Spectrum Aqua, Abbott Molecular). Each of the micro-channels was first dehydrated before the addition of the probe mixture. Co-denaturation of the probe mixture was performed on a ThermoBrite unit (Abbott Laboratories) at 95° C. followed by hybridization at 37° C. overnight. Post-wash was performed at 74° C. in 0.4× saline-sodium citrate (SSC) buffer containing 0.3% IPEGAL (Sigma-Aldrich, St. Louis, Mo.) followed by 2×SCC wash containing 0.1% IPEGAL and then DAPI (blue). The CEE™ channels were imaged on the Olympus BX51 fluorescence microscope equipped with filters to view DAPI, SpectrumAqua, SpectrumOrange, and SpectrumGreen (Olympus America Inc). Images were analyzed with use of the ISIS imaging system v5.2 (Metasystems, Waltham, Mass.). Evaluation of FISH signal patterns was performed on both CK-positive and CE-positive cells in the micro-channel. CTCs identified. The ratio of HER2:CEP 17 was calculated and a ratio >2.2 was regarded as positive for HER2 gene amplification.

Micro-Channel Capture Efficiency Using Multiple Antibodies.

Figure 31:
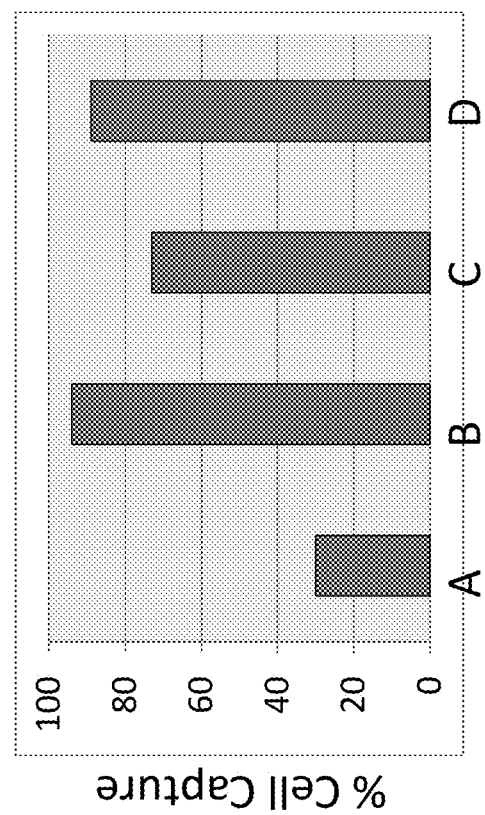
FIG. 31 shows capture of T24 and SKOV cells spiked into blood. 31A. The percentage capture of T24 cells using anti-EpCAM antibody. 31B. T24 capture % using anti-EpCAM and TROP-2 antibodies. 31C. SKOV capture % using anti-EpCAM antibody; 31D. SKOV capture % using anti-EpCAM and TROP-2 antibodies. By FACS T24 cells were shown to contain 4,000 and 60,000 EpCAM and TROP-2 antigens respectively; SKOV cells were shown to contain 66.000 and 12,000 EpCAM and TROP-2 antigens, respectively. Antibody capture is less efficient with low antigen expression on the cells, but increases in an additive manner when antibodies are used in combination.

The efficiency of cell capture using immuno-based systems is dependent on the presence and number of surface antigens on the cells. FIG. 31 shows the difference in capture using T24 and SKOV cell lines when incubated with either anti-EpCAM only and with a mixture of 2 antibodies, anti-EpCAM and Trop-2. As determined by flow cytometry, T24 and SKOV cells had about 4,000 and 60,000 EpCAM antigens, respectively, and the inverse level of Trop-2 antigens, about 60,000 and 12,000. The recovery of T24 cells increases from 30% with anti-EpCAM only, to 90% when the cells were incubated with both anti-EpCAM and Trop-2. SKOV cells were recovered at 80% with EpCAM and only marginally higher when Trop-2 was added. Since antibodies in the current system serve to populate the surface of the cells with biotin, these results demonstrate that antibodies bound to the surface of the cells are additive with respect to capture on the micro-channel, and are not mutually exclusive.

Figure 32A:
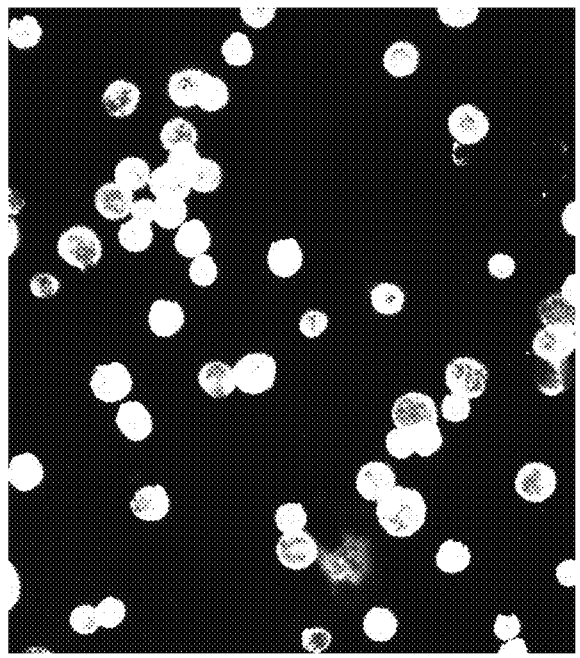
FIGS. 32A-32C show capture and staining of SKOV cells with EpCAM and with an antibody mixture.
Figure 32A:
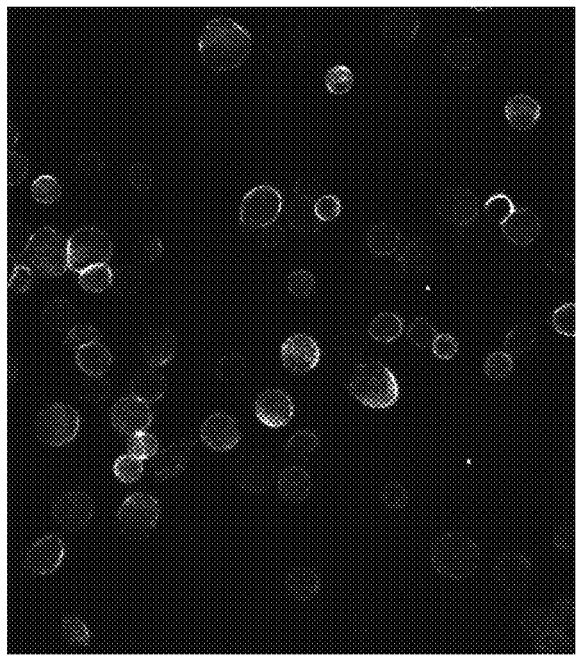
Figure 32B:
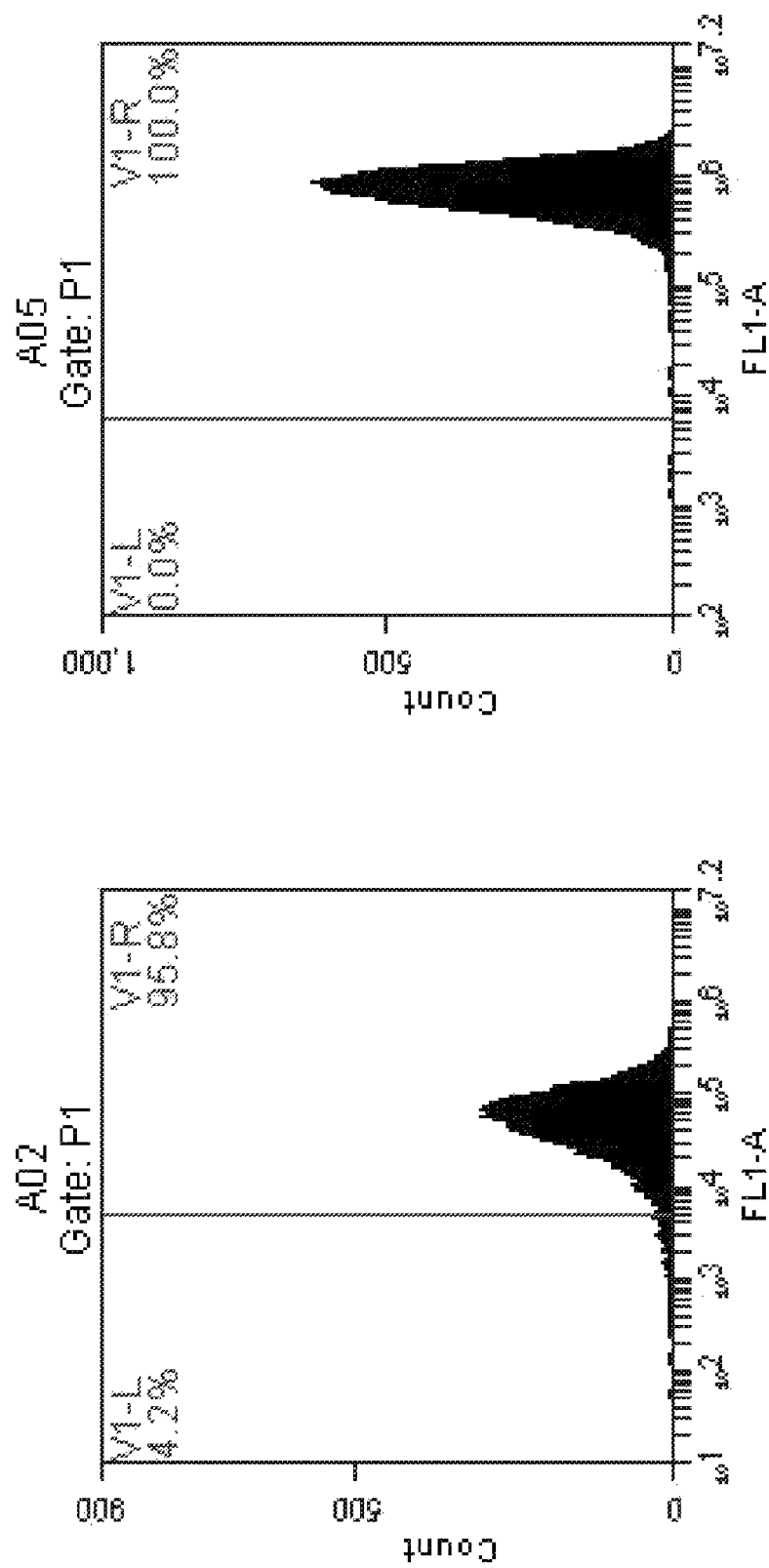
Figure 32C:
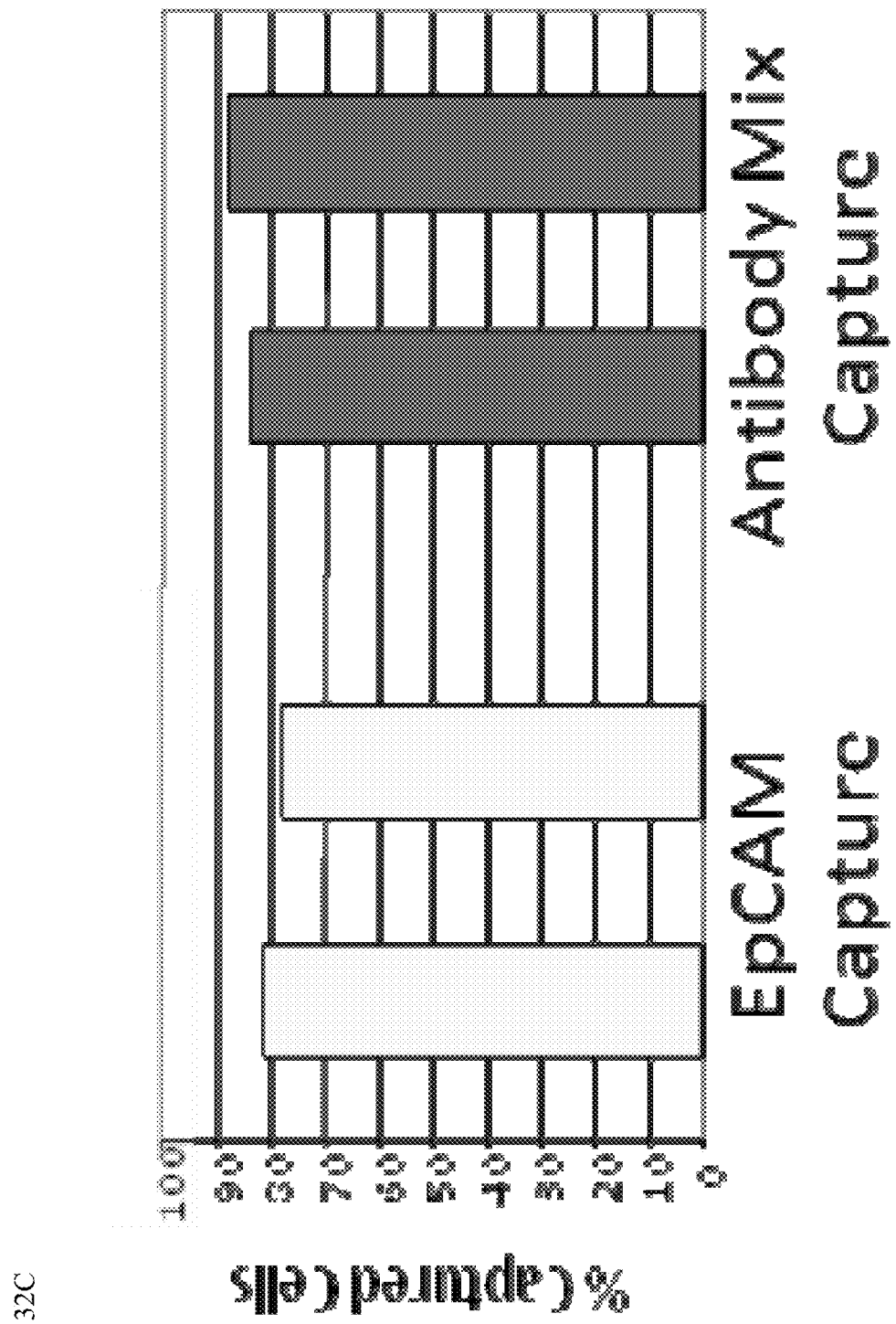

Additional studies on SKOV cells further demonstrate that while anti-EpCAM alone may be sufficient for good capture, additional antibodies improve detection when using CE. FIG. 32 shows the capture of SKOV cells with anti-EpCAM only and with a small antibody mixture containing anti-Her2/neu, anti-CD44 and anti-CD26. Flow cytometry showed an average of 66,000 EpCAM antigens and 620,000 surface antigens using the mixture (FIG. 32B). There is no significant difference in the cell capture with anti-EpCAM alone or with the antibody mixture (FIG. 32C). However, when SKOV cells incubated with anti-EpCAM-only were stained using the CE protocol, there was only faint staining, while the same cells with multiply bound antigens had significantly higher stain intensity as shown when the cells were viewed on microscope slides (FIG. 32A). This demonstrates that a mixture of antibodies may not be needed to capture a given cell but the extra antibody density on the surface of the cell significantly improves the staining intensity of the cell when using CE. Cells on the micro-channel were similarly detected whether using anti-CK or the CE protocol alone (discussed below).

Capture and Detection of CTCs.

Figure 33:
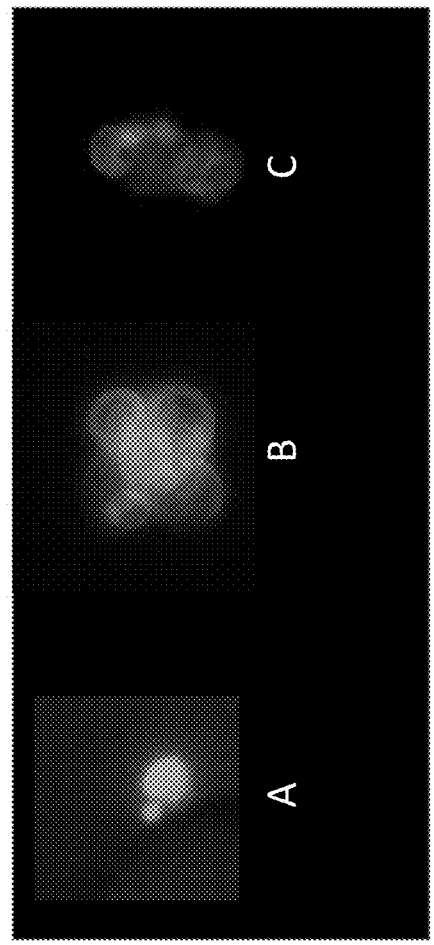
FIG. 33 shows immunofluorescent staining 33A. A LnCAP cell spiked into blood and captured on the micro-channel, stained for CK (green) and also nuclear stained with DAPI (blue). A small WBC is seen with only the nucleus stained blue. 33B. A cluster of CTCs from a clinical lung cancer sample captured on the micro-channel that are stained for CK. These cells were CD45 negative and DAPI positive (not shown). 33C. A cluster of cells from lung cancer showing triple staining with CK (green), CD45 (red) and DAPI (blue). Three CK-positive CTCs are shown with 2 small WBCs stained positive for CD45.
Figure 34:
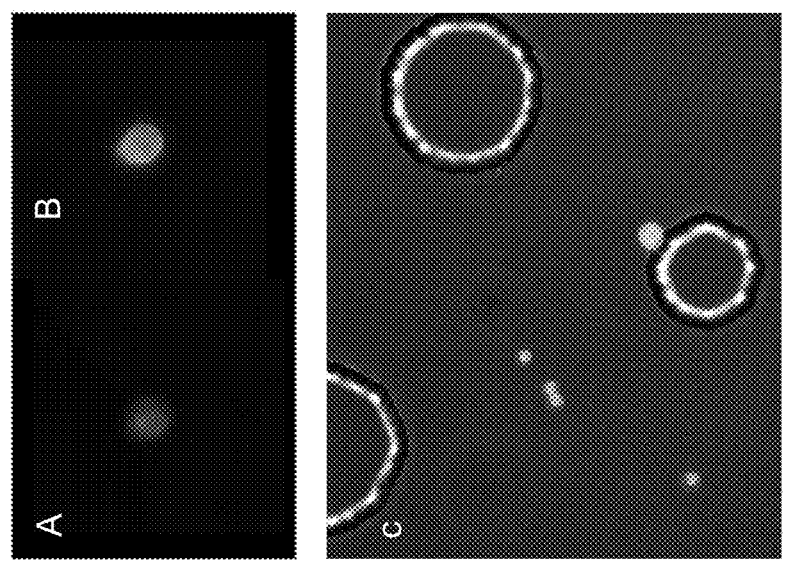
FIG. 34 shows the use of CEE-Enhanced™ to improve detection of cells on the micro-channel. 34A. A clinical breast cancer CTC stained for CK and nuclear-stained with DAPI. This cell is weakly CK positive. 34B. The same cell after subsequent stain with CE labeled with the same AlexaFluor-488 fluorophore in order to enhance the stain intensity. 34C. SKOV cell spiked into blood and recovered on the micro-channel using an antibody mixture (see methods). Cells on the channels were stained with CE-488 and DAPI. The four smaller WBCs stained for DAPI only, while the SKOV can be detected only with CE. This higher contrast image shows the outline of the post in the micro-channel. Together these images show that CE can be used to augment weakly staining CK cells or can be used to detect cells without CK stain.

The immuno-staining intensity by CK or CE is based on the number of antigens. For cell lines and many of the CTCs visualized in most systems, CK staining is clearly visible by manual microscopy. Single cells as well as small micro-emboli may be captured in the micro-channel (FIGS. 33A-C) since the spacing between the posts is sufficient to allow larger clumps of cells to pass between the posts on the channel. However there is a gradient of staining intensities in CTCs such that some are not easily detectable above background. In those cases where there is weak CK staining in a CD45-negative cell, it may still be difficult to distinguish a true positive from background. The clinical example of this is seen in FIG. 34A which shows a CTC captured from a breast cancer sample that was weakly CK positive. The location for this cell on the micro-channel was recorded and the cell was relocated after subsequent treatment with CE. In FIG. 34B the same cell was more intensely stained after treatment with CE. This demonstrates that the cell was clearly captured due to multiple capture antibodies on its surface, but the endogenous CK itself was low or down-regulated. Increased staining intensity was routinely observed on weakly CK positive cells. FIG. 34C shows an SKOV cell spiked into blood and captured on the micro-channel with the antibody mixture. CE-only was used to detect this cell. The high contrast image also shows the outline of the posts on the channel. Background WBCs remain DAPI positive only. FIG. 34 shows that CTCs may be stained de novo with CE, and that CE can also be used to enhance weakly stained CK-positive cells.

Table 9 shows the comparison between capture with anti-EpCAM alone and with an antibody mixture, as detected with anti-CK stain. Duplicate tubes of blood from metastatic cancer patients were incubated with anti-EpCAM-only and with the antibody mixture. On an individual basis, the effect of using an antibody mixture can range from no increase in CK-positive cells to several-fold higher. Overall, the antibody mixture captured significantly more CK-positive cells than anti-EpCAM-alone (mean 18.5 vs 26.5, paired t-test p=0.02). Since the distribution of these results was non-parametric, the paired Wilcoxon test was used and showed a median of 6 with anti-EpCAM vs 12 CK− detected cells with the antibody mixture (p=0.02).

Table 10 shows the additive nature of CTCs captured on the micro-channel under different capture and staining conditions. Two tubes of blood were collected from each patient, and capture tested with either anti-EpCAM alone or with the antibody mixture containing anti-EpCAM, unless otherwise specified. The captured cells on the micro-channel were initially stained and scored for the presence of CK and CD45, and then stained and scored for CE. The general trend as shown in Table 10 was that an antibody mixture generally captured more classically defined DAPI+/CK+/CD45− cells than anti-EpCAM alone, and that CE revealed more cells than did anti-CK. However, the heterogeneity of cells within samples is apparent even in this small cohort in that the percentage increase in different samples is quite variable. In two of the prostate samples, a third tube of matched blood was obtained and incubated with the same antibody mixture except that anti-EpCAM was omitted. The capture was comparable to the antibody mixture containing anti-EpCAM on prostate samples containing both high and low levels of endogenous CTCs. This suggests that there was an abundance of antibodies other than EpCAM bound to the surface of these cells. This is also consistent with increased capture using the antibody mixture since there are CTCs present that don't contain EpCAM (Table 9).

Table 10 further illustrates that there are EpCAM-positive cells that are captured but lack detectable levels of CK. These cells only become visible when anti-EpCAM-captured cells are stained with CE. In this case, CE is labeling only anti-EpCAM-containing cells since this is the only antibody used for capture. The antibody mixture showed the highest level of CE staining as might be expected. While the antibody mixture showed modestly higher CK stained cells, significantly more CE cells were detected in all cases, indicating that the antibody mixture was binding to many more CK negative cells than was anti-EpCAM alone. All positive CK or CE cells were CD45-negative.

Figure 35:
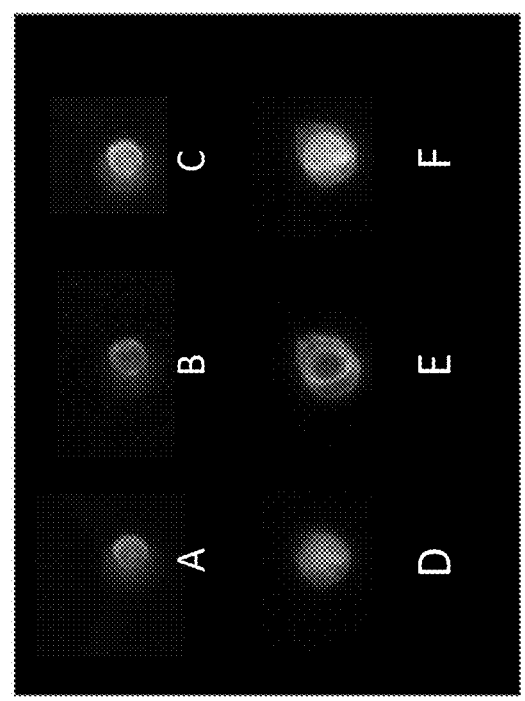
FIG. 35 shows co-staining clinical lung cancer CTCs with anti-CK and CEE-Enhanced™. 35A-C. A single CTC on the microchannel stained with anti-CK (A), CE-AlexaFluor-546 (orange, B), and 35C, a composite image. 35D-F shows the same order of staining but with a cell cluster of 2 cells. This demonstrates the co-staining of the internal CK antigen and the cell surface antigens with CE.

Dual staining was used to show simultaneous detection with anti-CK and CE. CTCs were captured with the antibody mixture followed by anti-CK (FIGS. 35A and 35D, labeled with AlexaFluor488, green fluorescence) and then CE (FIGS. 35B and 35E, labeled with AlexaFluor 546; orange fluorescence). FIGS. 35C and 35F are color composite images. FIG. 35D-F shows a cluster of two CTCs while A-C is a single cell on the micro-channel. All relocated DAPI+/CK+/CD45– cells became dual positive for green (CK) and orange (CE). FIG. 35 confirms that CK positive cells are simultaneously labeled with CE and that the anti-CK intensity can be augmented with a single color as shown in FIG. 34B or the CTC can be dual stained with anti-CK and CE having two different fluorescent dyes.

FIG. 36 shows CTCs isolated from a series of stage IV breast cancer samples using the antibody mixture for capture. Captured CTCs were first stained with anti-CK and then with CE. The dark bars show the number of CK-positive cells detected and in each case the light bars stacked on top of the dark bars show the additional cells detected with CE. Fifteen of 24 samples (63%) contained CK-positive cells (range 1-60 CTCs) while all of the samples contained at least one additional CE-positive cell (range 1-41; median=11; Wilcoxon test, p=0.02). The correlation coefficient (r=0.57, p=0.004) suggests a weak correlation between CK and CE but the trend does not suggest that CE is merely a percentage of anti-CK stained cells. This further suggests that different phenotypic populations of CTC are present within these samples, possibly related to other physiological factors.

In this example we describe a platform to capture and detect the heterogeneous phenotypes of tumor cells that may exist in patient samples. CTCs were isolated from buffy coats using the EpCAM antibody, or with mixtures of antibodies. Universal detection of specifically captured cells was based on CEE-Enhanced™ (CE) for in situ labeling of the capture antibodies bound to the surface of the captured CTCs on the micro-channel. CE co-stained all CK-positive cells and could be used to enhance the intensity of the CK-stained cells, or to detect cells without CK stain (FIGS. 34 and 35). Control blood from healthy volunteers showed no positive cells with either anti-CK or CE.

The use of antibody mixtures and CE showed that additional EpCAM-negative and CK-negative tumor cells were present in peripheral blood. Since both immuno-capture and immuno-detection is antigen concentration-dependent, the term 'negative' here indicates those cells that may contain some antigens, but are below the threshold for either capture or detection employed in this study. Table 10 shows that CTCs captured with anti-EpCAM alone, and stained for CK and CE, contained a population of tumor cells that was not CK-positive. Likewise, additional CK-positive cells could be identified when a mixture of antibodies was used for capture instead of EpCAM alone. The highest numbers of identified cells were seen when an antibody mixture was used for capture in combination with CE to detect those additional cells that contained very low levels of either EpCAM or CK or both.

The loss of EpCAM or CK in tumor cells has been extensively described. Loss of CK may be a function of independent oncogenic processes (Alix-Panabiéres C, et al., *Breast Cancer Res.* 11:R39 (2009); Woelfle U, et al., *Clin Cancer Res.* 10:2670-4 (2004); and Franzen B, et al., *Br J Cancer.* 74:1632-8 (1996)) or may be related to EMT (Paterlini-Brechot P, Benali N L. *Cancer Lett.* 253:180-204 (2007) and Willipinski-Stapelfeldt B. *Clin Cancer Res.* 2005; 11:8006-14). The present study was focused on detection of CTCs that did not contain either EpCAM or CK. CK can also be aberrantly expressed in lymphocytic cells, though CD45 is used to rule out the CK-positive lymphocytes. CK expression in disseminated tumor cells (DTC) seems to be much higher than in CTCs (Choesmel V, et al., *Breast Cancer Res.* 6:R556-70 (2004)), and expression caused by inflammatory processes can also contribute to CK false positives (Kowalewska M, et al., *Biochim Biophys Acta.* 1806:163-71 (2010)). Similar issues surround the up-regulation and down-regulation of EpCAM, with similar consequences for the isolation or detection of CTCs. It seems well established that EpCAM is found frequently in tumors (Went P T, et al., *Hum Pathol.* 35:122-8 (2004)); that it can be up-regulated in tumors, and has been associated with poor prognosis (Spizzo G, et al. *Breast Cancer Res Treat.* 86:207-13 (2004)). From the CTC perspective it is not the finding of CTCs that have expressed EpCAM that is in question, but the concern over false-negatives in the failure to detect CTCs that don't express EpCAM. Aside from the fact that not all tumors express EpCAM, there are issues of down-regulation of adhesion molecules in order to metastasize and migrate (Tai K Y, et al., *Oncogene.* 26:3989-97 (2007); van der Gun B T F, et al., *Intl J Cancer.* 123:484-9 (2008)), and the programmed down-regulation of EpCAM as part of EMT (Paterlini-Brechot P, et al., *Cancer Lett.* 2007; 253:180-204 and Willipinski-Stapelfeldt B. *Clin Cancer Res.* 11:8006-14 (2005)). Moreover, EpCAM can be lower as a result of chemotherapy and so CTC enumeration may vary as a result of treatment (Thurm H, et al., *Clin Cancer Res.* 9:2598-604 (2003)).

It is for these reasons that we developed a system to enrich cells with or without EpCAM and integrated this with an in situ labeling approach that fluorescently labels those cells with bound capture antibody. Within a biological system containing such a heterogeneous genotyptic etiology it may be difficult to predict with any certainty what kinds of tumor cells might be present in any given sample. If one attempts to apply specificity to the kinds of cells being enriched from a population by using antibodies, it makes sense to visualize the very targets of that enrichment. With heterogeneous samples, one sample may contain mostly EpCAM-positive cells while the next may have a different phenotype or range of phenotypes. Ancillary tumor-specific markers may then be used to confirm that they are indeed tumor cells or to measure tumor-specific mutations. In this example two biopsy-confirmed Her2/neu-positive samples from FIG. 36 were found to contain amplified Her2/neu signals in the CE detected CTCs, in addition to CK-positive cells. Thus CE may be used to identify a wider population of CTCs for further study than would normally be identified with anti-CK alone.

Isolation of CTCs from metastatic breast cancer samples using an antibody mixture showed additional CE-positive cells and that the numbers were not proportional to the endogenous levels of cells identified by anti-CK staining (FIG. 36). While it is desirable to detect more CTCs, the real value of alternate detection using CE may be as much qualitative as quantitative. The proportion of CK-negative or EpCAM-negative CTCs may provide additional diagnostic insights, by suggesting the levels of CTCs that have undergone EMT in a given sample. Specialized antibody mixtures directed to new cancer markers could be developed to enhance the detection of specific populations of CTCs.

The number and type of CTCs is often dependent on the isolation and detection technology, and in some embodiments an individual standard may be tied directly to a specific enrichment and detection format. There is a wide range of reported values, ranging from numbers roughly comparable to CellSearch to numbers in the hundreds and thousands per mL of blood (Nagrath S, et al., Nature. 2007; 450:1235-9 (2007) and Camara O, et al., J Can Res Clin Oncol. 135:643-7 (2008)). Timing is another consideration with regards to enumeration. CTCs isolated as point-of-care within a few hours of blood draw (Nagrath S, et al., Nature. 2007; 450:1235-9; Stott S L, et al., PNAS. 107:18392-7 (2010)) may be the most desirable. The half-lives of CTCs in circulation can range from less than 24 hours to only a couple of hours (Meng S, et al., Clin Cancer Res. 10:8152-62 (2004)), although half-lives of days and months have also been reported (Camara O, et al. World J Surg Oncol. 2006; 4:67 (2006)). The time of collection and storage are significant considerations for enumeration comparisons.

With regards to improved prognostic forecasting, it may be of limited value to simply find higher numbers using anti-EpCAM. Earlier processing or automated systems with higher sensitivity thresholds resulting in higher CTC values may improve prognostic value beyond that achieved by CellSearch. One interesting study in this regard measured all anti-EpCAM and anti-CK-positive 'objects' isolated by the CellSearch system (Coumans F A W, et al., Ann Oncol. 21:1851-7 (2010)). Multiple types of cellular particles and fragments were found to perform equivalently to the classically-defined intact cell in predicting survival. This would suggest that this system would be quite robust at its current level of prognosis, regardless of user bias, since ancillary observations support the same trend. It is in this robustness that the limitations emerge. Systems with associated redundancies reinforce a strong general trend.

Given the heterogeneity of circulating epithelial cells, most of which are assumed to be circulating tumor-associated epithelial cells, the question of detection specificity has not been well studied beyond the parameters of EpCAM and CK. Questions of EMT and the role of these cells at different stages of cancer is of intense interest. Studies in our lab have shown the majority of curable Stage I-III breast cancer samples have significant levels of CE stained cells but few CK-positive cells.

The current study demonstrates that the peripheral blood of cancer patients contains circulating tumor cells other than those normally detected with antibodies to EpCAM and cytokeratin. The use of CEE-Enhanced™ and antibody mixtures along with the traditional anti-EpCAM and anti-CK-based approach may lead to new insights into the diagnostic applications of CTCs.

TABLE 9

| Original tumor | Anti-EpCAM only | Antibody Mix |
|---|---|---|
| breast | 0 | 1 |
| prostate | 37 | 33 |
| breast | 8 | 25 |
| lung | 0 | 0 |
| breast | 8 | 12 |
| breast | 94 | 115 |
| breast | 0 | 1 |
| prostate | 57 | 97 |
| prostate | 0 | 0 |
| Colorectal | 0 | 1 |
| breast | 6 | 16 |
| lung | 1 | 2 |
| breast | 13 | 22 |
| breast | 54 | 72 |
| breast | 0 | 0 |
| breast | 0 | 1 |

Table 9 shows Comparison of the number of CK-positive CTCs detected with anti-EpCAM-only and with an antibody mixture (see Methods).

TABLE 10

| Cancer Type | Anti-EpCAM Cytokeratin Stain | Antibody Mix | Anti-EpCAM Additional CTCs detected | Antibody Mix with CEE-Enhanced™ stain[b] |
|---|---|---|---|---|
| Small Cell Lung Cancer | 24 | 47 | 151 | 148 |
| Prostate | 127 | 200 162[a] | 49 | 61 |
| Prostate | 2 | 5 7[a] | 11 | 27 |
| Prosate | 12 | 10 | 2 | 25 |
| Colorectal | | 1 | | 4 |

[a] A third tube of matched blood was processed using the antibody mixture that did not contain anti-EpCAM
[b] All cells were CD45-negative and DAPI-positive Table 10 shows a comparison of the number of CTCs detected with different antibody capture and detection methods.

Example 16. Methods of Using Enhanced Stain

CK staining detects a cytoplasmic epithelial protein in a CTC and reflects the epithelial structural integrity of the cell. Processes such as apoptosis, higher cancer stage de-differentiation and epithelial to mesenchmal transition can lower the levels of CK in a tumor cell. As such, cells with lower CK may be more indicative of aggressive cancer than those CTCs with higher CK.

Anti-EpCAM (epithelial cell adhesion molecule) is frequently used to capture CTCs since it is on the surface of epithelial cells and may be over-expressed in some cancers. It may also be down-regulated in some cancers.

If a CTC has been captured by anti-EpCAM antibody then CEE-Enhanced (CE) staining visualizes the EpCAM by labeling antibodies on the surface of the captured cell. This applies to any other antibody or antibody cocktail that is bound to surface antigens on the cell. CE represents detection of EpCAM, or any combination of antibodies used for the capture of CTCs as described herein.

It may be that the ratio of CK to CE is the more important factor in determining cell aggressiveness, metastatic potential, or resistance to chemotherapy. The differential expression of EpCAM and CK varies by stage and type of tumor and may change during the course of chemotherapy, and so knowing the CK as well as CE values may provide a better discrimination of cancer progression or cancer treatment than mere enumeration.

The other factor involved in the usefulness of CE is that CTCs may have different expression of antigens at different stages. In the case of Stage IV metastatic breast cancer many of the CTCs are detected with CK and these cells contain differential ratios of CK to CE (Table 10). This ratio may be prognostic of outcome or of treatment efficacy. By contrast, the ratio of CK to CE becomes less useful in the earlier stage cancers, Stage I-III, since few if any CK cells are detected, while numerous CE cells are detected. The presence of CE and not CK in this case may represent a different class of CTCs that are more transformed by EMT.

In the case of chemotherapy, many tumor cells lose CK and EpCAM and therefore the cocktail would be needed to capture a more representative cross-section of CTCs. Even in this case the cells down-regulated in CK may have EpCAM, or tumor cells with no EpCAM may have CK expression. Therefore the use of cocktails with specified antibodies as described herein, together with detection by both CK and CE may provide better discrimination of metastatic potential or disease progression. Ratios of CK to CE likewise may improve prognostic potential even more, as a function of capture antibody composition.

The data in Table 11 shows the number of CK and CE detected CTCs and the CK/CE ratio for breast cancer samples with Stage IV (T4) metastatic cancer, and those with earlier stage disease. The absolute number of CE CTCs may be important, or some combination of CE and CK cells may be important, or an increasing or decreasing ratio of CK and CE may be important in staging cancer status or assessing disease progression. In this table the status of drug treatment or chemotherapy is unknown. CE provides a unique tool not only to expand the current detection methods, but to potentially derive additional information about the progression of cancer. In combination with antibody cocktails CE could significantly improve the diagnostic value of CTCs.

TABLE 11

| ID | CK | CE | T Stage | ratio CK/CE |
|---|---|---|---|---|
| 334 | 0 | 4 | T1 | 0.00 |
| 347 | 0 | 1 | T1 | 0.00 |
| 349 | 0 | 4 | T2 | 0.00 |
| 360 | 0 | 5 | T1 | 0.00 |
| 376 | 0 | 1 | T1 | 0.00 |
| 387 | 0 | 1 | T2 | 0.00 |
| 401 | 0 | 7 | T2 | 0.00 |
| 413 | 0 | 4 | T1 | 0.00 |
| 417 | 0 | 24 | T1 | 0.00 |
| 446 | 0 | 7 | T1a | 0.00 |
| 448 | 0 | 3 | T1 | 0.00 |
| 454 | 0 | 4 | T2 | 0.00 |
| 358 | 6 | 12 | T1c | 0.50 |
| 394 | 0 | 0 | T1 | na |
| 428 | 0 | 0 | T2 | na |
| 432 | 0 | 0 | T2 | na |
| 351 | 0 | 2 | T4 | 0.00 |
| 352 | 0 | 12 | T4 | 0.00 |
| 382 | 0 | 3 | T4 | 0.00 |
| 396 | 0 | 3 | T4 | 0.00 |
| 403 | 0 | 6 | T4 | 0.00 |
| 456 | 0 | 9 | T4 | 0.00 |
| 465 | 0 | 33 | T4 | 0.00 |
| 468 | 0 | 10 | T4 | 0.00 |

TABLE 11-continued

| ID | CK | CE | T Stage | ratio CK/CE |
|---|---|---|---|---|
| 469 | 0 | 15 | T4 | 0.00 |
| 366 | 1 | 23 | T4 | 0.04 |
| 392 | 1 | 15 | T4 | 0.07 |
| 397 | 2 | 18 | T4 | 0.11 |
| 386 | 4 | 17 | T4 | 0.24 |
| 353 | 2 | 7 | T4 | 0.29 |
| 357 | 3 | 10 | T4 | 0.30 |
| 356 | 1 | 2 | T4 | 0.50 |
| 395 | 13 | 23 | T4 | 0.57 |
| 364 | 4 | 6 | T4 | 0.67 |
| 365 | 50 | 41 | T4 | 1.22 |
| 384 | 15 | 12 | T4 | 1.25 |
| 344 | 3 | 2 | T4 | 1.50 |
| 388 | 34 | 22 | T4 | 1.55 |
| 383 | 60 | 22 | T4 | 2.73 |
| 385 | 6 | 1 | T4 | 6.00 |

Another example of the use of CE is in the intensity of the fluorescent signal obtained. The CK intensity is a function of internal cytokeratin levels that can be influenced as described earlier by apoptosis, cancer stage, or epithelial to mesenchymal transition. Likewise the surface markers may be influenced by the same factors. The use of selected antibodies directed to specific cell surface markers may thus provide insite into some aspects of cancer cell stage or progression. The ratio therefore of the staining intensity of the internal CK compared to the staining intensity of the cell surface using CE can provide both new and corroborating information to help in the diagnosis of cancer cell stage or status.

Figure 37:
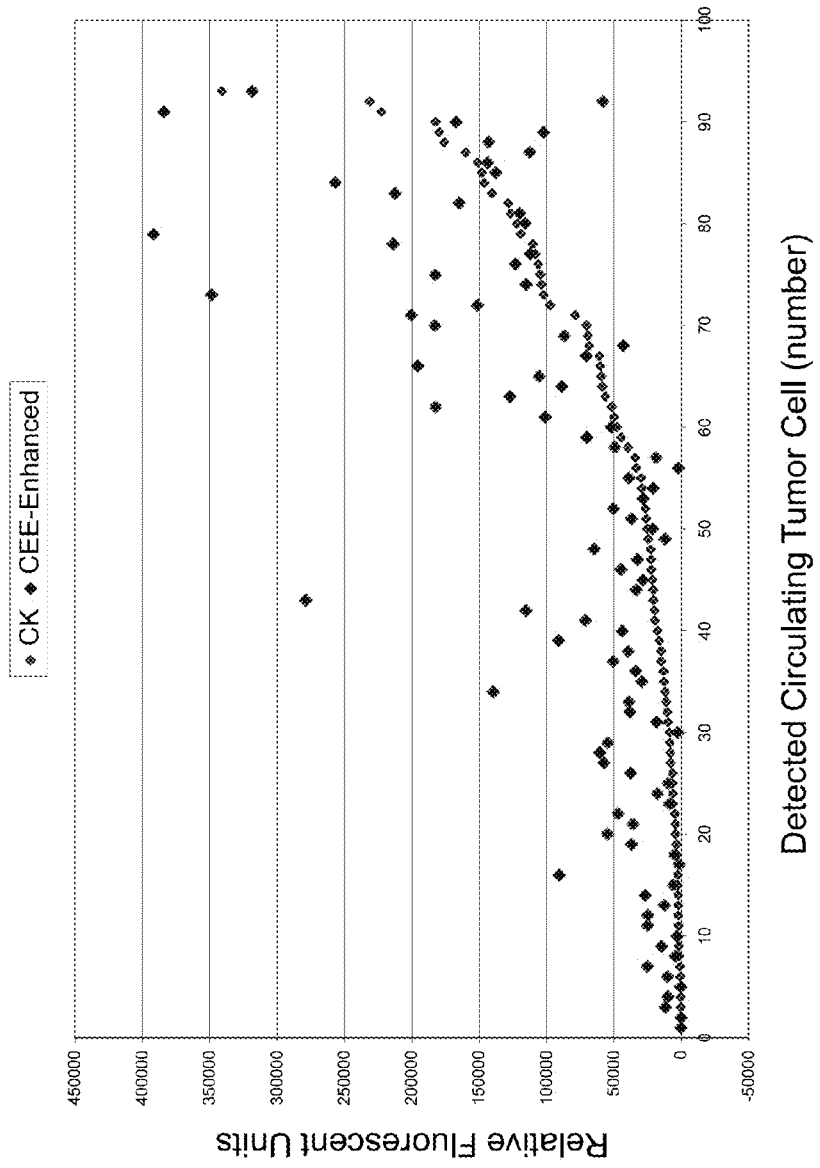
FIG. 37 shows the plot of the relative fluorescent intensity of prostate CTCs detected in a single clinical patient sample. The small markers arranged from low to high are the intensities of CK visualized by anti-CK antibody labeled with AlexaFlur 488. The cell surface capture antibodies are detected with CEE-Enhanced labeled with the same fluorescent probe. This plot shows the relative difference in CK to CE intensities on each CTC detected.

FIG. 37 shows an example of a clinical prostate sample where 93 CTCs were detected using the microfluidic channel, and identified as being CK+ and CD45 negative. The the position of each of these cells was recorded and their CK relative fluorescence intensity RFI was determined using a fluorescence slide scanner. These cells were further stained with CE, their positions determined and the RFI determined. Since both CK and CE used a fluorescent dye with 488 excitation/523 emmission, their relative intensities could be plotted and compared. FIG. 37 shows a sorted plot of the CK intensities from low to high for visual clarity, and on the same graph are the relative CE intensities for the same CTCs, There is a range of RFI for both CK and CE. In most cases the presence of increased CE stain provides further confirmation that these cells have the specific cancer capture antibodies on the surface of the cells. The RFI of the CK and CE may thus provide additional insight into the status of the cancer. Factors such as a very high or very low ratio of intensities between CE and CK may provide diagnostic information to help in the treatment of disease. Selective use of specific capture antibodies may provide additional selective insight when visualized on the cell, either alone or in combination with CK. The presence of CE stain associated with cell surface antibodies provides distinctive and different information than CK alone, which is just a marker of an epithelial cell.

Example 17. Novel Platform for Detection of CK+ and CK− CTCs

Metastasis is a complex multistep process that begins with the epithelial-mesenchymal transition (EMT). Circulating tumor cells (CTCs) are believed to have undergone EMT and thus express low levels or lack epithelial markers commonly used for enrichment and/or detection of such cells. However, most methods today only target EpCAM and/or cytokeratin to enrich epithelial CTCs, resulting in failure to recognize other, perhaps more important, CTC phenotypes that lack expression of these markers. This example describes a population of complex aneuploid CTCs that do not express cytokeratin or CD45 antigen in patients with breast, ovarian, or colorectal cancers. These cells were not observed in healthy subjects. We show that the primary epithelial tumors were characterized by similar complex aneuploidy, indicating conversion to an EMT phenotype in the captured cells. Collectively, this example provides a new method for highly efficient capture of previously unrecognized populations of CTCs.

Current assays for CTC capture likely miss populations of cells that have undergone EMT. Capture and study of CTCs that have undergone EMT would allow a better understanding of the mechanisms driving metastasis.

An epithelial-mesenchymal transition (EMT) in cancer is characterized by loss of cell adhesion, repression of E-cadherin, acquisition of mesenchymal markers, increased cell motility, and invasive potential (Thiery JP. *Nature Reviews Cancer* 2:442-54 (2002)). Though several approaches describing alternative strategies for recovery and detection of CTCs have been reported, the only FDA-approved technique for CTC detection relies on the use of antibodies targeting the epithelial cell adhesion molecule (EpCAM), followed by cytokeratin (CK) and CD45 staining to confirm an epithelial phenotype (Nagrath S, et al. *Nature*, 450: 1235-9 (2007) and Allard W J, et al. *Clinical Cancer Research* 10:6897-904 (2004)). These modern enrichment techniques have characterized such CTCs, showing correlation with survival (Coumans F A W, et al., *Annals of Oncology* 1-7 (2010); Goodman Jr O B, et al., *Cancer Epidemiology Biomarker Prevention* 18:1904-13 (2009); and Cristofanilli M, et al., *New England Journal of Medicine* 351:781-91(2004)) and response to treatment (Cristofanilli M, et al., *New England Journal of Medicine* 351: 781-91 (2004); Hayes D F, et al., *Clinical Cancer Research* 12:4218-24 (2006)). CTCs can also express biomarkers reflective of the primary tumor and could be useful as a surrogate for tumor biopsy (Attard G, et al., *Cancer Res* 69:2912-8 (2009) and Maheswaran S, et al., *New England Journal of Medicine* 359:366-77 (2008). However, only a small proportion of CTCs are capable of establishing distant metastasis (Fidler I J, et al., *Journal of Cellular Biochemistry* 101: 927-36 (2007) and Tarin D, et al., *Cancer Research* 44:3584-92 (1984)) as evidenced by the phenotypic heterogeneity observed among CTCs within patient blood samples (Attard G, et al., *Cancer Res* 69:2912-8 (2009)). Biological mechanisms, such as EMT, may also result in a spectrum of epithelial marker shedding and a more progressive metastatic phenotype. Yet, these important EMT-derived CTC populations are likely missed by current techniques (Mego M, et al., *Nat Rev Clin Oncol* 7:693-701). In fact, one of the initial reports describing EpCAM expression levels in various cancer types found absent staining in tumors of mesenchymal lineage such as melanomas and sarcomas (Momburg F, et al., *Cancer Research* 47:2883-91 (1987)). This suggests that perhaps the most invasive and metastasis-primed cells that have undergone EMT, thus resembling a more mesenchymal phenotype, may no longer express EpCAM and/or cytokeratin and evade detection with traditional techniques.

Blood Collection.

Blood samples were drawn from patients with ovarian, peritoneal, fallopian tube, breast or gastrointestinal cancers or benign pelvic tumors according to an Institutional Review Board—approved protocol at the M. D. Anderson Cancer Center, where patients were being treated. Diagnoses of cancers and benign pelvic tumors were based on pathologic review. All blood samples from healthy donors who had no history of cancer were drawn after obtaining informed consent. Blood samples were collected into 8.5-mL vacutainer tubes containing 1.5 mL acid-citrate-dextrose (ACD Solution A Vacutainers; Becton, Dickinson and Company, Franklin Lakes, N.J.). Within 60 minutes of blood collection, the addition of 250 μL of anti-clumping reagent (CEE-Sure™; Biocept, San Diego, Calif.) was injected into each tube before being shipped to Biocept and processed within 24 hours of collection. Samples were stored at room temperature (RT) before processing in Biocept's CAP accredited CLIA laboratory.

In the comparison to CellSearch®, three tubes (one Cell-Save tube and two ACD tubes containing CEE-Sure™) of blood were collected from each of the 88 patients. Given that the CellSearch® assay is FDA approved for CTC enumeration using only 7.5 mL of blood, only one tube was obtained and delivered to an independent medical laboratory (Genoptix Medical Laboratory, Carlsbad, Calif.). For our microchannel platform, the overall assay recovery was interpolated between two tubes of blood. Each tube of blood was used to generate a cell pellet for capture within one microchannel. Each microchannel was scored for presence of CTCs based on the standard stain criteria (CK+/CD45−/DAPI+). For the comparison between CellSearch®, the higher total number of CTCs detected in one of two tubes of blood was selected.

CTC Capture and Detection.

Blood samples were initially processed for recovery of peripheral blood mononuclear cells by using a Percoll density gradient method and Leucosep tubes (Greiner Bio-One, Monroe, N.C.). Each Leucosep tube was pre-filled with Percoll Plus (GE Healthcare, Piscataway, N.J.) at a density of 1.083 g/mL (adjusted using normal saline) and stored at RT. Each 10-mL blood sample was diluted three-fold with a 1× phosphate-buffered saline (PBS) containing 1 mg/mL casein and 1 mM ethylenediaminetetraacetic acid (EDTA) buffer and poured directly into a Leucosep tube. Samples were centrifuged for 15 minutes at 1000 g at RT in swinging bucket rotors (Allegra X-12R centrifuge; Beckman Coulter, Brea, Calif.), with breaks set to their lowest setting. After separation, the upper layer (above the separation barrier) was recovered by decanting into a 50-mL conical tube through a 70-μm cell strainer (BD). The decanted sample volume was adjusted to 45 mL with PBS/casein/EDTA and then centrifuged for 10 minutes at 400 g. Supernatant was removed by aspiration with use of a vacuum wand. The pellet was then resuspended and incubated with Fc blocker (100 μg/mL human IgG) and capture antibody cocktail (each antibody adjusted to 1 μg/mL) for 30 minutes at RT. The antibody cocktail consisted of: EpCAM, Trop-2, (BD Biosicences, San Diego, Calif.); c-Met and Folate binding protein receptor, (R&D Systems, Minneapolis, Minn.); N-Cadherin, (Sigma-Aldrich, St Louis, Mo.); CD318, MSC (Mesenchymal Stem Cell), HER2, (Biolegend, San Diego, Calif.); Muc-1 (Fitzgerald, Acton, Mass.); EGFR (Santa Cruz Biotechnology, Santa Cruz, Calif.). After incubation, the pellet was washed by adjusting the volume to 45 mL with PBS/casein/EDTA and centrifuging for 10 minutes at 400 g at RT. Biotinylated anti-mouse secondary antibody was added to the pellet and after mixing, was incubated for 30 minutes at RT. The resulting pellet was washed three times with PBS/casein/EDTA. Each wash step consisted of centrifugation for 10 minutes at 400 g, followed by supernatant aspiration. The final pellet was suspended in 1 mL PBS/BSA/EDTA and subjected to capture and staining on the CEE™ microchannel (manufactured at Biocept, Inc, San Diego).

Samples were pulled through microchannels with syringe pumps (manufactured at Biocept Inc, San Diego) at a volumetric flow rate of 18 μL/min. After the entire sample was processed through the microchannels, cells were cross-linked by using an NHS homobifunctional protein cross-linker and fixed with 80% MeOH. Cells were stained with a mixture of antibodies for cytokeratins 7/17, 18, 19, (BioLegend, San Diego, Calif.) and a pan-cytokeratin antibody targeting CK 4, 5, 6, 8, 13, 18 (BioLegend, San Diego, Calif.) labeled with AlexaFluor-488 (green), CD45 antibody (BioLegend, San Diego, Calif.) labeled with AlexaFluor-594 for 30 minutes, washed with PBS and stained with DAPI III counterstain. Channels were stored at +8° C. until microscopic analysis.

Microscopic CTC enumeration was performed to detect CTC-based CK+/CD45−/DAPI+ stain criteria. The precise location (X- and Y-stage coordinates) of each CTC was recorded, permitting re-localization of cells after FISH for nuclear interrogation. Visualization was achieved and images captured with use of the Olympus BX51 fluorescence microscope (Olympus America Inc, Center Valley, Pa.) at 200× magnification. After enumeration, each microchannel was processed for multicolor FISH by using direct-labeled probes (Abbott Molecular, Des Plaines, Ill.) specific to the centromeres of chromosomes 8 (CEP 8-SpectrumAqua) and 11 (CEP 11-SpectrumGreen) and the locus-specific region on chromosome 20 (LSI 20q12-SpectrumOrange) for the ovarian cancer cases. Centromere-specific probes for chromosomes 8 (SpectrumAqua), 11 (SpectrumOrange), and 17 (SpectrumGreen) were used for colorectal cancer cases. For the breast cancer cohort, direct labeled probes specific to Her2/centromere 17 were employed (Abbott Molecular, Des Plaines, Ill.). Each FISH probe was initially validated for chromosomal localization and hybridization efficiency (sensitivity and specificity) on metaphases and 500 normal interphase cells from five independent donors within microchannels. For each test case reported here, the FISH scoring strategy involved two steps. First, each CTC identified during the enumeration step was relocated and scored for the number of signals present for each of the probes directly within the microchannel. Next, all remaining CK−/CD45−/DAPI+ cells captured within the microchannel were scored for the number of FISH signals present for each probe; this permitted identification of CTCs that are cytokeratin-negative and complex aneuploid (trisomic for one probe and monosomic or trisomic for another locus/probe). Visualization was achieved and images captured with use of the Olympus BX51 fluorescence microscope (Olympus America Inc) at 400× and 600× magnification.

Scoring criteria were based on observed hybridization efficiencies for each probe as evaluated on a total of 2500 normal peripheral blood lymphocytes (500 nuclei from each of five donor blood samples) and cultured tumor cells (500 each MCF7 and SKBr3 cells) captured within the microchannel. As expected, monosomy (presence of only one FISH probe signal) alone for any probe was observed in 5-10% of nuclei scored. Trisomy alone for any probe was observed in less than 0.2% of nuclei scored. Therefore, monosomy alone in a single cell was not sufficient to deem a cell as abnormal by FISH. However complex aneuploidy, as defined by the detection of at least one trisomy for one probe with at least one additional abnormality, monosomy or trisomy (i.e. combined aneuploidy at two loci with at least one locus being trisomic), for another probe was not observed in any of 2500 normal nuclei scored. Thus, these criteria were used to classify CK− and CK+ cells as complex aneuploidy.

Cell Lines and Flow Cytometry.

MDA-MB-231 (ATCC, HTB-26), BT474 (ATCC, HTB-20), and SKBr3 (ATCC, HTB-30) breast cancer, T24 bladder, HeyA8 and SKOV3 ovarian cancer cell lines were cultured according to ATCC recommendations, verified by morphology, growth curve analysis, and tested for mycoplasma. Measurement of surface antigens targeted by the capture cocktail was performed by incubating trypsin-detached, non-permeabilized breast cancer cells (listed above) with the indicated mouse anti-human IgG antibodies, followed by incubation with PE-labeled anti-mouse IgG (Sigma-Aldrich, St Louis, Mo.), according to a standard flow cytometry protocol. After additional washes to remove excess antibody, the cells were analyzed on the Accuri C6 flow cytometer (Accuri Cytometers Inc., Ann Arbor, Mich.). Flow cytometric estimation of the number of antibodies bound per cell was determined by using BD Quantibrite™ PE beads (BD Biosciences), according to the manufacturer's instructions. By using known ratios of PE to antibodies, we converted PE molecules per cell to antibodies per cell.

Immunofluorescence Staining on Tissue.

Both paraffin and frozen tissue sections of the primary tumors were blocked in 20% horse serum for 1 hour at RT before incubation with an anti-cytokeratin antibody mixture (see above) overnight at RT in a humidified chamber. After sufficient washing, binding of the secondary antibody linked to fluorescein isothiocyanate (FITC) was performed for 1 hour at RT. Slides were subsequently washed and mounted with use of DAPI mounting media (Vector Laboratories, Burlingame, Calif.). Visualization was achieved and images captured with use of the Olympus BX51 fluorescence microscope (Olympus America Inc) at 400× magnification.

Fluorescence In-Situ Hybridization.

Formalin-fixed paraffin-embedded tumor sections were deparaffinized in xylene and rehydrated in an ethanol series. This was followed by pretreatment of the slides with a paraffin pretreatment kit III according to the manufacturer's recommendations (Abbott Laboratories, Abbott Park, Ill.). Slides were serially dehydrated and allowed to air-dry. CEP8, CEP11, and 20q12 probes (Abbott Laboratories) were added to the dried slides and sealed with rubber cement. Cells captured in each of the microchannels were first dehydrated before the addition of the probe mixture. Co-denaturation of the probe mixture was performed on a ThermoBrite unit (Abbott Laboratories) at 75° C. for 5 minutes (slides) or 95° C. for 45 minutes (microchannels) followed by hybridization at 37° C. overnight. Post-wash was performed at 74° C. in 0.4× saline-sodium citrate (SSC) buffer containing 0.3% IPEGAL (Sigma-Aldrich, St. Louis, Mo.) followed by 2×SCC wash containing 0.1% IPEGAL and then counterstained with DAPI (blue). The slides and microchannels were imaged on the Olympus BX51 fluorescence microscope equipped with filters to view DAPI, SpectrumAqua, SpectrumOrange, and SpectrumGreen (Olympus America Inc). Images were analyzed with use of the ISIS imaging system v5.2 (Metasystems, GmbH, Germany). For slides, the number of fluorescent signals was counted in a minimum of 200 non-overlapping, intact nuclei. Abnormal FISH patterns were noted in percentages for each patient sample. Data are presented as the final percentage of normal and abnormal nuclei for each patient.

Matched Blood and Tissue Collection.

Blood samples were drawn before surgery from seven patients with ovarian cancer. Tumors removed during surgical resection were formalin-fixed and paraffin-embedded for pathologic review. Representative blocks confirming cancer by hematoxylin and eosin staining were assessed for complex aneuploidy and cytokeratin staining as described. Fresh frozen tissue was obtained from two patients for FISH quality control.

Quantitative Real-Time PCR.

Total RNA was isolated by using a Qiagen RNeasy kit. Using 500 ng of RNA, cDNA was synthesized by using a Verso cDNA kit (Thermo Scientific) as per the manufacturer's instructions. Analysis of mRNA levels was performed on a 7500 Fast Real-Time PCR System (Applied Biosystems) with SYBR Green-based real-time PCR, using primers designed with Primer Express (Applied Biosystems). Specific primers for vimentin (5'-TCCAAGCCTGACCT-CACTGC-3' (forward) and 5'-TTCATACTGCTGGCGCA-CAT-3' (reverse)), N-cadherin (5'-GCCATTGATGCGGAT-GATC-3' (forward) and 5'-CCTGTACCGCAGCATTCCAT-3' (reverse)), Twist (5'-TCGACTTCCTGTACCAGGTCCT-3' (forward) and 5'-CCATCTTGGAGTCCAGCTCG-3' (reverse)) and Snail (5'-CCCAAGGCCGTAGAGCTGA-3' (forward) and 5'-GCTTTTGCCACTGTCCTCATC-3' (reverse)) were used; 18S rRNA was used as a housekeeping gene. PCR was done with reverse-transcribed RNA and 100 ng/μL of sense and antisense primers in a total volume of 20 μL. Each cycle consisted of 15 seconds of denaturation at 95° C. and 1 min of annealing and extension at 60° C. (40 cycles).

Ex Vivo Spiking Experiments.

To demonstrate precision and reproducibility in capture of tumor cells, cultured cells were spiked into normal peripheral blood from healthy donors. In demonstrating precision, ~10, ~25, ~50 T24, BT474, MDA-MB231, SKBr3, and SKOV3 cells were spiked into 10 mL of whole blood in triplicate. A total of 30 tubes of blood (10 mL) were prepared and processed for these precision studies. For reproducibility experiments, each of the above tumor cells lines was spiked at ~150 tumor cells to 10 mL whole blood from normal donors in 10 independent replicates. Thus, a total of 50 tubes of blood (10 mL) were prepared and processed for reproducibility as described for clinical samples. To determine the actual concentration and spiked number of tumor cells for each cell line was based on sequential spotting of equal volume cell suspensions onto glass slides. Spiked tumor cell and whole blood mixtures were allowed to incubate overnight at room temperature prior to processing as described for clinical samples. To demonstrate capture of post-EMT cell populations, SKOV3ip1 cells were grown in RPMI 1640 supplemented with 15% fetal bovine serum and 0.1% gentamicin sulfate (Gemini Bioproducts, Calabasas, Calif.). For EMT induction, cells were grown in RPMI 1640 without serum supplemented with recombinant human TGF-beta1 (R&D Systems, Minneapolis, Minn.) at a concentration of 10 ng/mL for 72 hours. Cells were trypsinized at 72 hours and spiked ex vivo into mouse blood that had been added to anticoagulant citrate dextrose (ACD) containing anti-clumping reagent (CEE-Sure™; Biocept, San Diego, Calif.) prior to entering a microchannel. For samples described here, the same antibody cocktail was used for capture followed by processing and capture within microchannels.

Orthotopic Ovarian Mouse Experiment.

Ten nude mice were injected with $2.5 \times 10^5$ HeyA8 ovarian cancer cells into the peritoneal cavity. Mice were monitored until the first mouse became moribund, which occurred 36 days after injection. All mice were killed on the same day and about 350 μL of blood per mouse was collected by cardiac puncture and added to pre-filled eppendorf tubes containing ACD. Blood samples were processed in microchannels as described.

Statistical Analysis.

Differences in continuous variables were analyzed using the Mann-Whitney rank sum or t-test. A P-value<0.05 was considered statistically significant.

Capture of Carcinoma Cells Independent of EpCAM Expression.

Figure 42:
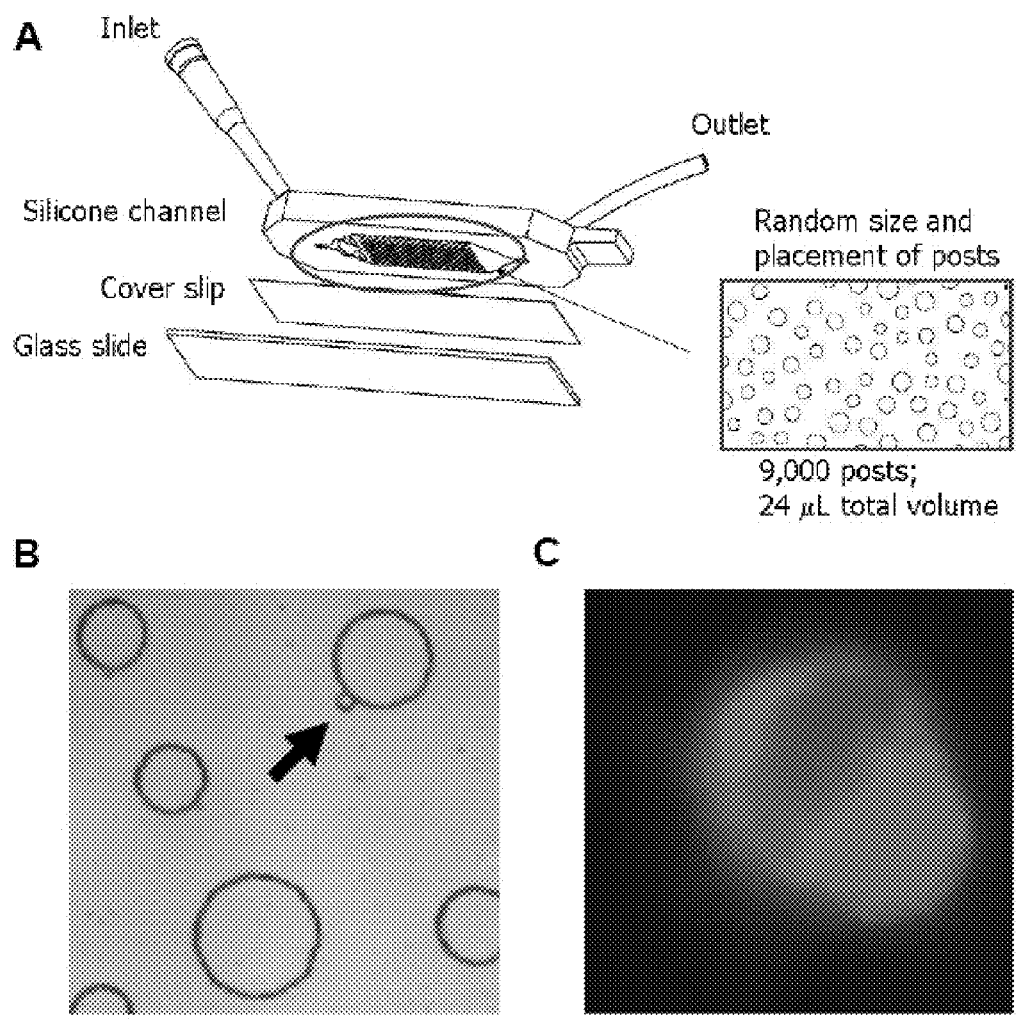
FIG. 42 shows cell enrichment and extraction (CEE™) platform. (a) The CEE™ platform is centered on the principles of microfluidics to selectively capture and enrich target cells, including CTCs. The inclusion of a glass coverslip as part of the CEE™ device allows direct and immediate visual assessment of captured cells, in addition to immunochemical and genetic analysis, using standard microscopy. Furthermore, the polymer chip holder, which forms the basis of the micro-channel consists of ~9000 posts of variable size and diameter. (b) Demonstration of the ability of the CEE platform to directly perform molecular characterization within the microchannel. (c) Representative image of a CK+/CD45−/DAPI+ CTC within the microchannel.
Figure 43:
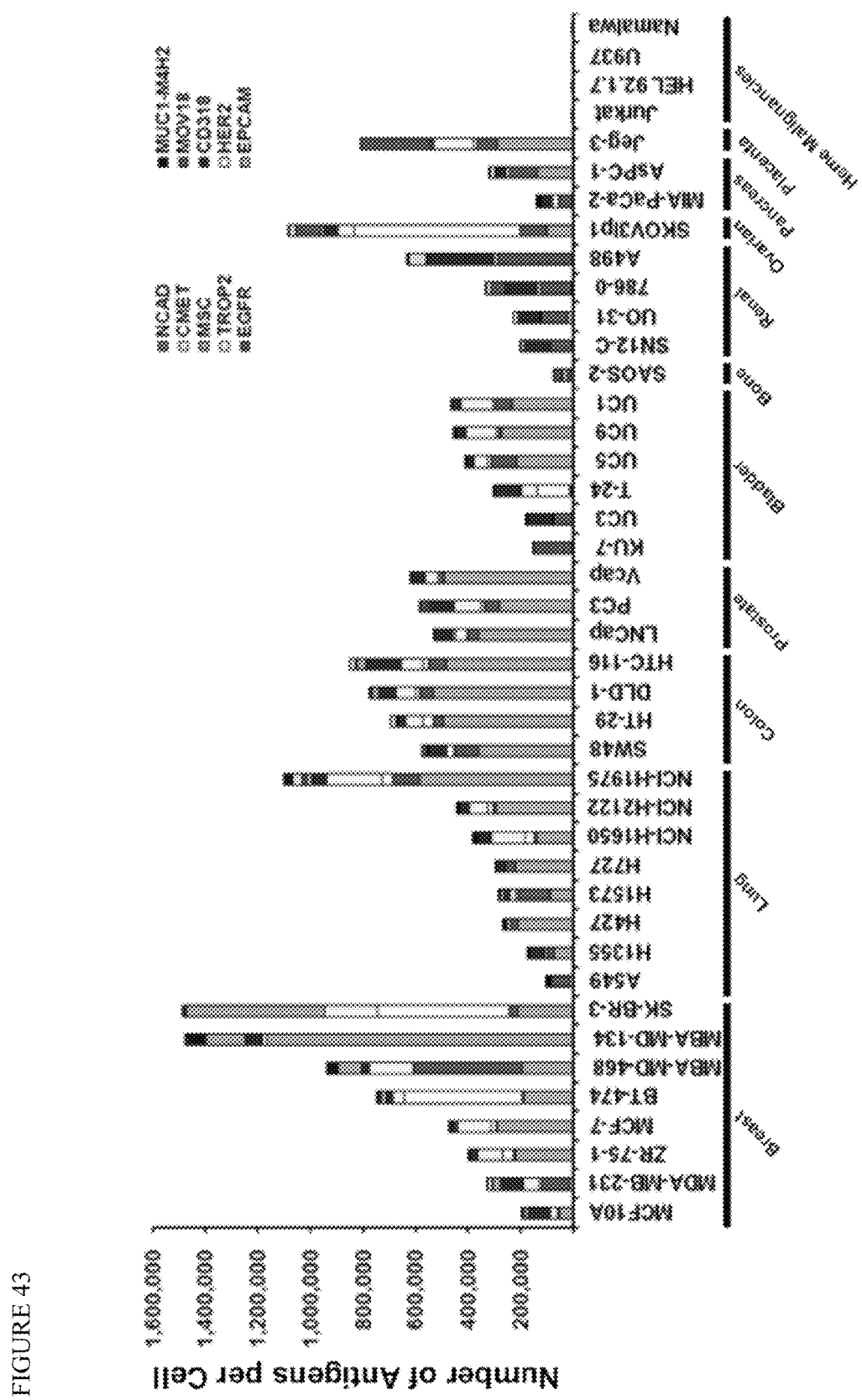
FIG. 43 shows expression of antibodies (antigens per cell) included in the AC15 cocktail in 43 cancer cell lines analyzed by flow-assisted cell sorting.

We have developed a microfluidic-based system for capture and analysis of rare cells in circulation, including CTCs (FIG. 42a). The platform is capable of capturing rare cells from blood for subsequent molecular characterization directly within a uniquely designed microchannel (FIG. 42b,c). Each microchannel consists of a roughly rectangular chamber (40 mm×12 mm×55 microns) in which approximately 9000 variable diameter posts are randomly placed to disrupt laminar flow, and maximize the probability of contact between target cells and the posts, which are derivatized with streptavidin, resulting in their capture (14). The platform is versatile, permitting assay optimization with flexibility in the number of antibodies selected for capture and detection as well as allowing immediate and direct single-cell microscopic analyses through the transparent microchannel without the need to manipulate cells onto glass slides. This approach utilizes an antibody cocktail that is added directly to cells prior to capture, enabling recovery of variable CTC phenotypes. Briefly, this mixture contains antibodies directed towards a variety of epithelial cell surface antigens (EpCAM, HER2, MUC-1, EGFR, folate binding protein receptor, TROP-2), and mesenchymal or stem cell antigens (c-MET, N-Cadherin, CD318 and mesenchymal stem cell antigen). Each of these antibodies was tested by flow cytometry for reactivity to several well-characterized cancer cell lines (e.g., SKOV3, LnCaP, SKBR3) and shown to be additive in binding to cells (FIG. 43). Antibodies were tested to have minimal cross-reactivity to nucleated cells in healthy control blood. Analytical control samples, namely blood from healthy donors spiked with cancer (SKOV3) cells, were run using this antibody mixture to ensure optimal performance in detecting tumor cells (based on cytokeratin staining).

Figure 38:
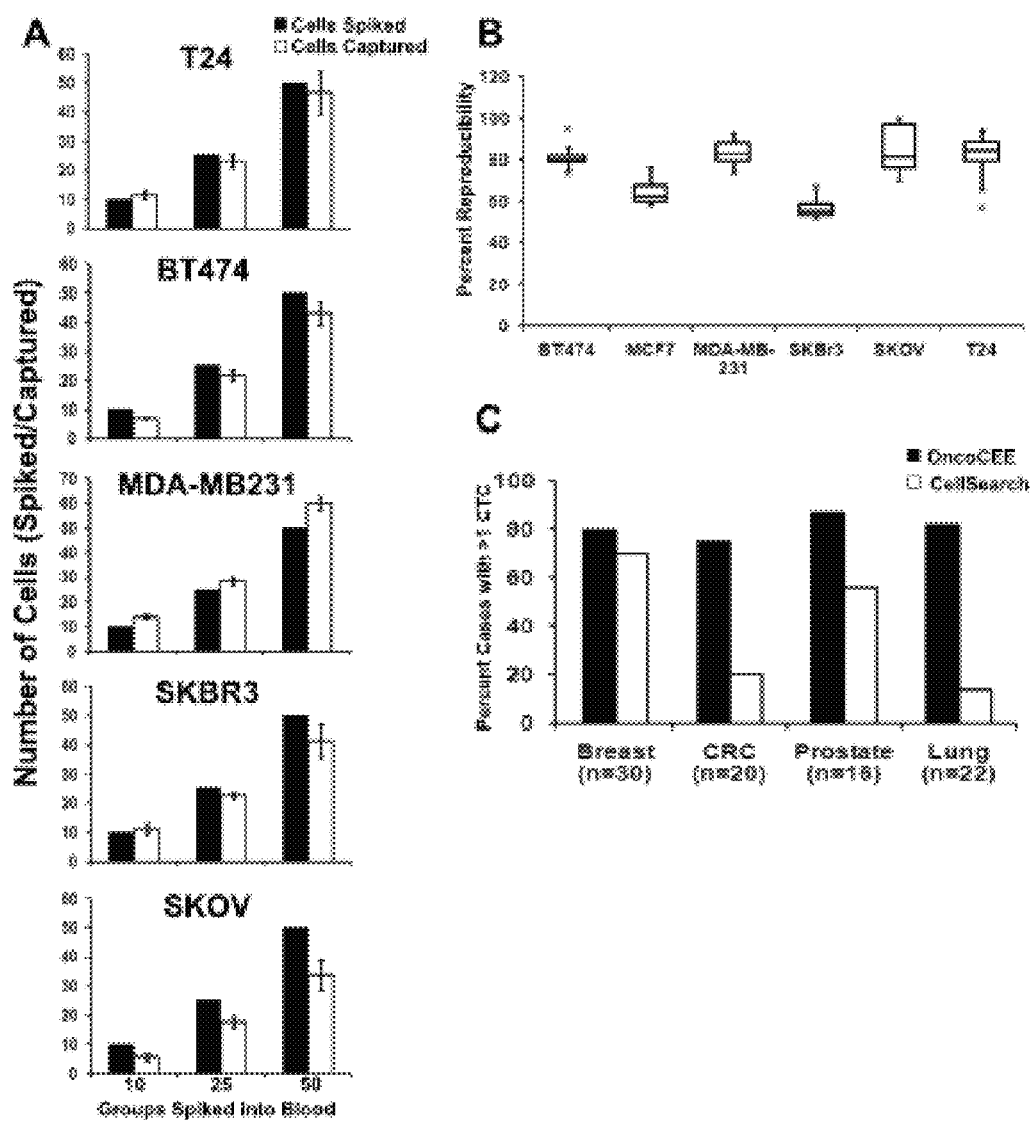
FIG. 38 shows efficiency and reproducibility of cell capture and comparison to CellSearch® technology. (a) Median number of captured carcinoma cells after ex vivo spiking of approximately 10, 25 or 50 cells into 10 mL human blood when using the antibody cocktail against cells of varying EpCAM expression. Each spike was performed in triplicate. (b) Percent reproducibility of cell capture after 10 separate ex vivo spikes into blood (pink-minimum outlier, red-maximum outlier). (c) Percentages of captured SKOV3 and T24 carcinoma cells after ex vivo spiking of approximately 150 cells into 10 mL human blood when using EpCAM antibody only, the antibody cocktail, or the antibody cocktail without the EpCAM antibody. (d) Comparison with the CellSearch® platform for CK+ CTCs captured from patients with breast, colorectal, lung or prostate carcinomas. a: Tumor types approved for CTC enumeration using CellSearch®, b: For samples from breast, colorectal and lung cancer patients, the antibody cocktail (AC15) composed of 10 monoclonal antibodies was used, c: For samples from prostate cancer patients, the antibody cocktail (AC16) composed of 11 monoclonal antibodies was used. * $P<0.05$, ** $P=0.001$, ‡ $P=0.0001$.

Analytical validation of the platform to demonstrate precision, reliability and reproducibility in recovery and detection of CTCs based on CK+/CD45−/DAPI+(4',6-diamidino-2-phenylindole) staining was performed with ex vivo spiking experiments of carcinoma cells into whole blood. Tumor cell capture efficiency was validated through a series of cell spiking experiments. We demonstrate analytical precision in recovery and detection of low to high EpCAM expressing target cells independent of the number of cells spiked (FIG. 38a). We further show >95% reproducibility in tumor cell capture with several cell lines (FIG. 38b). Capture efficiency using the antibody cocktail was demonstrated with low (T24) and medium (SKOV3) EpCAM expressing cell lines (Rao C G, et al., *Int J Oncol* 27:49-57 (2005)). While SKOV3 cells had high capture efficiency with EpCAM alone as well as with cocktail (>80%), T24 capture efficiency was markedly improved from <10% capture with EpCAM only to >80% with antibody cocktail (P=0.0001; FIG. 38c).

Next, clinical verification of capture efficiency was tested by examining CTCs in patient samples. In the first cohort of 21 patients with advanced stage disease, we compared CTC detection with our platform using either EpCAM alone or antibody cocktail (Table 11). Improved recovery was observed with higher CTC numbers in 14 of 21 samples with the antibody cocktail (P=0.07). In 100 normal blood controls, only 1 CK+/CD45−/DAPI+ cell was detected, demonstrating high specificity of the staining procedure. In the second, larger cohort of 88 patients with advanced stage lung, breast, colorectal or prostate cancer, we compared CellSearch® and our platform using the antibody cocktail for capture (FIG. 38d). Based on standard CK+/CD45−/DAPI+ stain criteria, our platform was found to be more sensitive for CTC enumeration across all four tumor types.

TABLE 12

|  | EpCAM Only | Cocktail |
| --- | --- | --- |
| CRC | 31 | 28 |
| Lung | 12 | 37 |
| Breast | 4 | 4 |
| CRC | 4 | 10 |
| CRC | 42 | 45 |
| Breast | 11 | 19 |
| Breast | 4 | 3 |
| Lung | 5 | 68 |
| Lung | 3 | 9 |
| Prostate | 4 | 14 |
| Breast | 17 | 13 |
| Breast | 3 | 1 |
| CRC | 0 | 6 |
| Lung | 0 | 6 |
| Breast | 2 | 4 |
| Breast | 18 | 26 |
| Skin | 1 | 11 |
| Breast | 4 | 4 |
| Lung | 6 | 4 |
| Prostate | 74 | 62 |
| Breast | 13 | 24 |

Table 12 shows comparison of CTC capture between EpCAM only and the antibody cocktail using OncoCEE™ CTC detection based on standard stain criteria (CK+/CD45−/DAPI+) using 8.5 mL blood from patients with advanced stage cancer.

Capture and Detection of CK− CTCs in Patients with Breast, Ovarian or Colorectal Cancers.

Figure 39:
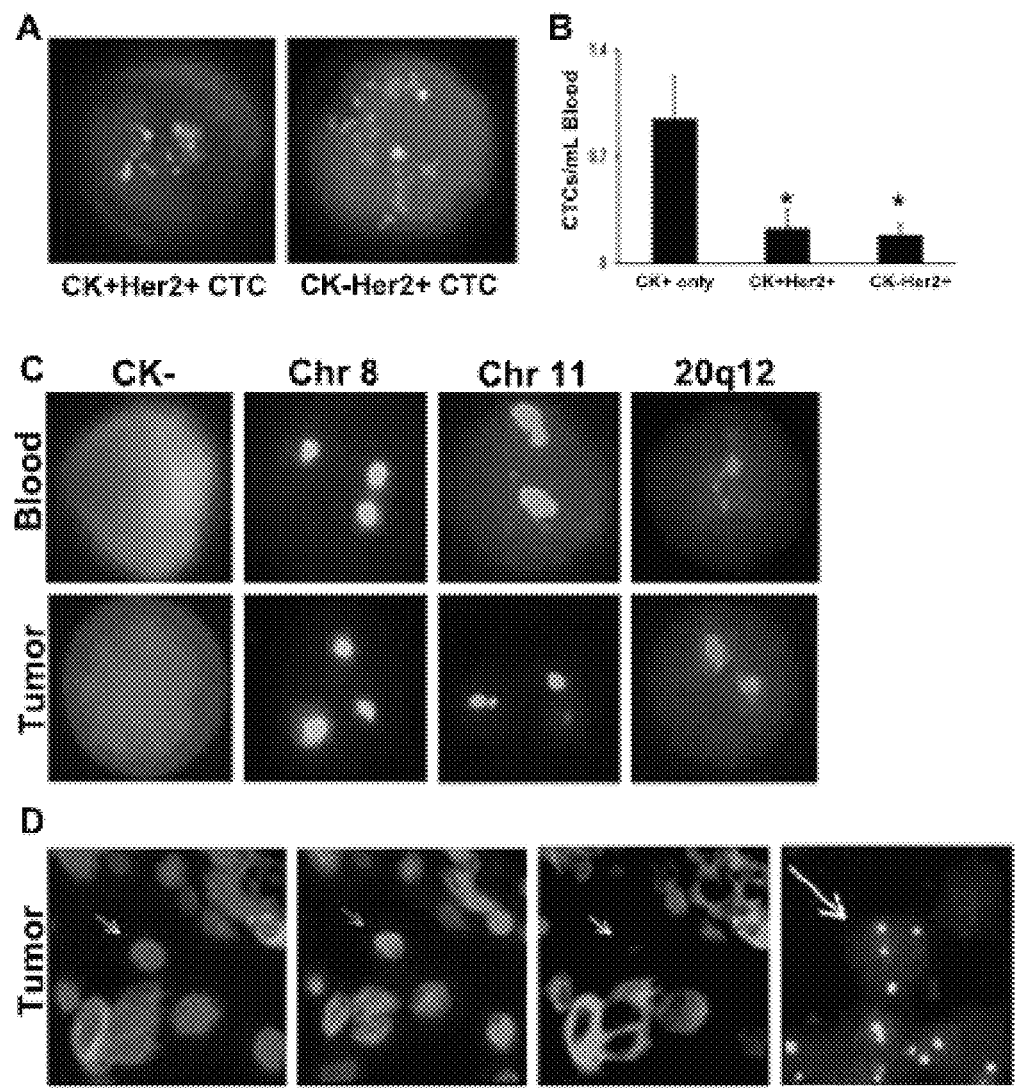
FIG. 39 shows capture of CK+ and CK− complex aneuploid CTCs in breast, ovarian or colorectal cancers. (a) Representative images illustrating detection of HER2+/CK+ and HER2+/CK− CTCs. Both cells display a >2.2 Her2/Centromere 17 ratio, confirming positive HER2 amplification. (b) Comparison of total CK+/CD45−, CK+/CD45−/HER2+ and CK−/CD45−/HER2+ cells from advanced stage breast cancer patients. (c) Capture of circulating ovarian (top) and colorectal (bottom) carcinoma cells that stain for cytokeratin. Subsequent FISH shows an ovarian cancer cell with trisomy in chromosome 8 (blue) and monosomy in region 20q12 (red), whereas the colorectal cancer cell has trisomy in chromosome 8 and tetrasomy in chromosome 17 (orange, arrows). (d) Capture of cytokeratin-negative circulating ovarian (top) and colorectal (bottom) carcinoma cells. FISH of an ovarian cancer cell with trisomy in chromosome 8 (blue), monosomy in chromosome 11 (green) and tetrasomy in region 20q12 (orange), whereas the colorectal cancer cell has trisomy in chromosomes 8 (blue) and 11 (green) and monosomy in region 20q12. The average number of total cytokeratin, complex aneuploid cytokeratin-positive and cytokeratin-negative circulating tumor cells per milliliter of blood is shown for (e) ovarian and (f) colorectal cancer patients. * $P<0.05$, ** $P=0.007$.

Given that CK expression levels can often be variable among epithelial cells and absent among other non-epithelial cell types, we examined CK staining efficiency within the microchannel using a third cohort of Her2-neu positive breast cancer samples (n=19) for which fluorescence in situ hybridization (FISH) analysis of the HER2 locus enabled confirmation of CTC recovery independent of CK/CD45 staining (FIG. 39a). CK+ cells were located in each of the 19 cases and used as target cells for analysis of HER2 by FISH. In addition, all CK−/CD45− cells were also classified as "possible" CTCs for subsequent analysis of HER2 signals. In 18 of 19 cases, a range of 0.04-2.4 HER2 amplified CTCs per mL blood were detected among the CK+/CD45− and CK−/CD45− classified cells, suggesting the CK− Her2-amplified CTCs originated from the primary tumor. Interestingly, only 24.3% of all CK+CTCs were found to have Her2-neu amplification (P=0.007, FIG. 39b). Surprisingly, 49.7% of the HER2-amplified cells were CK− (FIG. 39b). These results demonstrate the inefficiency in detection of CTCs based solely on CK+/CD45− stain criteria, resulting in failure to detect a significant population of HER2-amplified cells. Thus, given the unique design and amenity to sequential staining and FISH, the platform enabled incorporation of FISH directly within the microchannel as a valuable independent method in confirming recovery of both CK+ and CK− CTCs immediately after CK staining.

To further confirm the use of the FISH-based strategy, we applied the same antibody cocktail capture approach and CTC detection (CK+/CD45−/DAPI+ staining) on samples from patients with advanced ovarian or colorectal cancer. To verify detection of CTCs, we again used FISH, but with the aim to detect aneuploidy (unbalanced genomic copy number changes). We rarely found CK+/CD45− stained cells; roughly 0.1 cells/mL blood of ovarian cancer patients regardless of stage, tumor grade or CA-125 levels (Table 13). FISH probes targeted to frequently gained genomic regions in ovarian and colorectal carcinoma were chosen based on array comparative genomic hybridization data (Mayr D, et al. *American Journal of Clinical Pathology* 126:101-9 (2006) and Camps J, et al., *Genes, Chromosomes & Cancer* 48:1002-17 (2009)). Each probe was first tested on a total of 2500 normal peripheral blood cells from five donors and in CK+ cultured SKOV3 cells to determine hybridization efficiency and scoring accuracy in interphase cells captured within the microchannel (see methods above). Cells that displayed only a monosomic signal for any one of the three probes were excluded (potential signal overlap). Therefore, only cells classified as either trisomic or complex aneuploid (at least one locus gain and another gain or loss at a second locus) were enumerated. As observed with the HER2 positive breast cancer cohort, for both ovarian and colorectal cancer, we found that not only captured CK+/CD45− cells (FIG. 39c), but also co-captured CK−/CD45− staining cells (FIG. 39d, Tables 14 and 15) had complex aneuploidy. Complex aneuploidy was not observed among normal control blood samples. Similar to breast cancer, when assessing for frequency of complex aneuploidy, colorectal and ovarian cancer patients had nearly the same number of CK− as CK+CTCs (FIGS. 39e and f). Thus, the presence of CK− complex aneuploid cells further demonstrates the inefficiency of CK as a marker to detect all candidate CTCs.

TABLE 13

| Age (years) | Total CK+ | Pathology | Stage | CA-125 |
| --- | --- | --- | --- | --- |
| 55 | 0 | Endometrioid ovarian adenocarcinoma | IV | 8 |
| 41 | 7 | Granulosa cell tumor of the ovary | Recurrent | 13 |
| 59 | 0 | Granulosa cell tumor of the ovary | Recurrent | 14 |
| 31 | 1 | High-grade adenocarcinoma + sarcomatoid features | IIb | 9 |
| 62 | 0 | High-grade endometrioid adenocarcinoma | Recurrent | 37 |
| 49 | 0 | High-grade mucinous adenocarcinoma | IIIc | 210 |
| 73 | 4 | High-grade mullerian adenocarcinoma | IV | 76 |
| 66 | 0 | High-grade papillary adenocarcinoma | IV | 261 |
| 59 | 0 | High-grade papillary serous adenocarcinoma | IIIc | 26 |
| 69 | 0 | High-grade papillary serous adenocarcinoma | IV | 22 |
| 55 | 14 | High-grade papillary serous adenocarcinoma | Recurrent | 104 |

TABLE 13-continued

| Age (years) | Total CK+ | Pathology | Stage | CA-125 |
|---|---|---|---|---|
| 66 | 0 | High-grade serous adenocarcinoma | Recurrent | — |
| 66 | 1 | High-grade serous adenocarcinoma | Recurrent | 184 |
| 66 | 0 | High-grade serous adenocarcinoma | Recurrent | 15 |
| 70 | 0 | High-grade serous adenocarcinoma | IIIc | 295 |
| 54 | 0 | High-grade serous adenocarcinoma | IIIc | 9 |
| 69 | 1 | High-grade serous adenocarcinoma | IIIc | 5,505 |
| 69 | 0 | High-grade serous adenocarcinoma | IIIc | 273 |
| 45 | 0 | High-grade serous adenocarcinoma | IIIc | 116 |
| 78 | 0 | High-grade serous adenocarcinoma | IV | 213 |
| 74 | 0 | High-grade serous adenocarcinoma | IV | 44 |
| 60 | 1 | High-grade serous adenocarcinoma | IV | 67 |
| 58 | 0 | Low-grade mixed endometrioid adenocarcinoma | Recurrent | 1,147 |
| 59 | 11 | Low-grade papillary serous adenocarcinoma | Recurrent | 578 |
| 83 | 0 | Metastatic malignant mixed mullerian tumor | IIIc | 83 |
| 65 | 0 | Peritoneal serous adenocarcinoma | Recurrent | 26 |
| 53 | 21 | Poorly differentiated ovarian adenocarcinoma | IV | 18 |

Table 13 shows CK+ cells captured with antibody cocktail in blood from women with ovarian cancer (cells per 17 mL of whole blood, total of two tubes).

TABLE 14

| Total CK+ Cells | Complex Aneuploidy | | Trisomy and Complex Aneuploidy | | Pathology | CA-125 | Chemo |
|---|---|---|---|---|---|---|---|
| | CK+ | CK− | CK+ | CK− | | | |
| 7 | 0 | 0 | 1 | 2 | Granulosa cell tumor of the ovary | 13 | Yes |
| 1 | 0 | 1 | 0 | 1 | High-grade adenocarcinoma with sarcomatoid features | 9 | Yes |
| 0 | 0 | 0 | 0 | 0 | High-grade endometrioid adenocarcinoma | 37 | Yes |
| 0 | 0 | 0 | 0 | 0 | High-grade mucinous adenocarcinoma | 210 | Yes |
| 4 | 2 | 0 | 2 | 2 | High-grade mullerian adenocarcinoma | 76 | Yes |
| 0 | 0 | 0 | 0 | 3 | High-grade papillary adenocarcinoma | 261 | Yes |
| 0 | 0 | 0 | 0 | 0 | High-grade papillary serous adenocarcinoma | 26 | Yes |
| 14 | 0 | 2 | 1 | 5 | High-grade papillary serous adenocarcinoma | 104 | Yes |
| 0 | 0 | 0 | 0 | 2 | High-grade serous adenocarcinoma | 295 | No |
| 0 | 0 | 0 | 0 | 1 | High-grade serous adenocarcinoma | 9 | Yes |
| 0 | 0 | 2 | 0 | 3 | High-grade serous adenocarcinoma | 213 | Yes |
| 0 | 0 | 0 | 0 | 3 | High-grade serous adenocarcinoma | — | Yes |
| 1 | 0 | 0 | 0 | 2 | High-grade serous adenocarcinoma | 184 | Yes |
| 11 | 1 | 0 | 1 | 1 | Low-grade papillary serous adenocarcinoma | 578 | No |
| 0 | 0 | 0 | 0 | 1 | Metastatic malignant mixed mullerian tumor | 83 | No |
| 0 | 0 | 0 | 0 | 2 | Peritoneal serous adenocarcinoma | 26 | Yes |
| 21 | 2 | 0 | 2 | 0 | Poorly differentiated ovarian adenocarcinoma | 18 | Yes |

Table 14 shows the yield of ovarian circulating tumor cells when looking at complex aneuploidy (defined as at least one locus gain and a gain or loss at a separate locus) or at least trisomy in one locus (cells per 8.5 mL of whole blood, average scored, 2,137 cells/patient).

TABLE 15

| Total CK+ Cells | Complex Aneuploidy CK+ | Complex Aneuploidy CK− | Trisomy and Complex Aneuploidy CK+ | Trisomy and Complex Aneuploidy CK− | Pathology | Stage | CEA |
|---|---|---|---|---|---|---|---|
| 1 | 0 | 2 | 1 | 3 | Well-differentiated | I | 2 |
| 6 | 0 | 0 | 1 | 1 | Moderately differentiated | IIa | 1 |
| 5 | 0 | 0 | 0 | 0 | Poorly differentiated | IIa | 6 |
| 5 | 0 | 0 | 0 | 2 | Moderately differentiated | IIIb | 2 |
| 1 | 1 | 1 | 1 | 2 | Moderately differentiated | IIIb | 1 |
| 0 | 0 | 0 | 0 | 0 | Colon adenocarcinoma | Metastatic | 158 |
| 0 | 0 | 0 | 0 | 0 | Colon adenocarcinoma | Metastatic | 57 |
| 0 | 0 | 0 | 0 | 1 | Colon adenocarcinoma | Metastatic | 2 |
| 0 | 0 | 0 | 0 | 0 | Colon adenocarcinoma | Metastatic | 17 |
| 11 | 0 | 1 | 0 | 4 | Colon adenocarcinoma | Metastatic | 62 |
| 5 | 0 | 0 | 1 | 8 | Colon adenocarcinoma | Metastatic | 787 |
| 5 | 1 | 1 | 2 | 2 | Colon adenocarcinoma | Metastatic | 4 |
| 0 | 0 | 0 | 0 | 0 | Rectal adenocarcinoma | Metastatic | 39 |
| 0 | 0 | 0 | 0 | 3 | Rectal adenocarcinoma | Metastatic | 59 |
| 12 | 0 | 0 | 0 | 0 | Rectal adenocarcinoma | Metastatic | 4 |

Table 15 shows cytokeratin and aneuploidy results for resected colon carcinoma (collected after resection) and metastatic colorectal carcinomas (cells per 8.5 mL of whole blood, average scored, 2,855 cells/sample). CEA, carcinoembryonic antigen.

Cytokeratin-Negative CTCs Found within the Primary Tumor.

Figure 40:
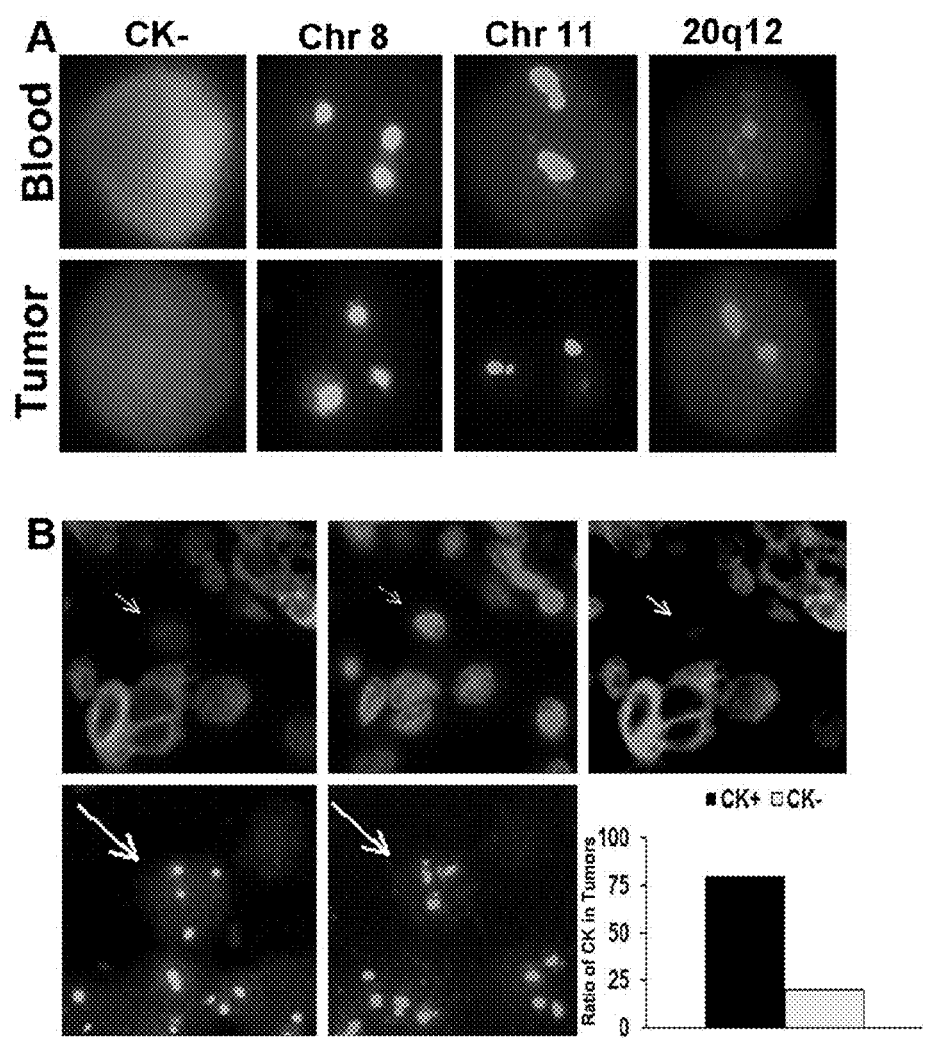
FIG. 40 shows matched cytokeratin-positive and -negative cells in circulation and primary tumor. (a) Cytokeratin-negative ovarian cancer cells identified in circulation (top) at the time of surgical resection have similar aneuploidy as regions in the tumor (bottom). Represented are cells with trisomy of chromosome 8. (b) Cytokeratin staining of ovarian carcinoma samples reveals cytokeratin-negative cells with aneuploidy (arrows) similar to those detected in circulation. Approximately 20% of the tumor had such cytokeratin-negative cells.

We hypothesized that if the isolated CK− CTCs are the consequence of EMT then similar cells should be present within the primary tumor. We sought to verify that the circulating aneuploid cells identified in ovarian cancer patients had molecular features reflective of the primary tumor and, thus, a useful population of CTCs. Blood was collected from 7 patients just before cytoreductive surgery. Multiple regions in the matched tumor and CTCs shared similar complex aneuploid patterns (FIG. 40a). Interestingly, about 20% of these aneuploid regions within the tumor were cytokeratin-negative and were heterogeneous in distribution (FIG. 40b). Although similar findings using FISH in CTCs and CECs compared to primary tumors have been described (Fehm T, et al., Clinical Cancer Research 8:2073-2084 (2002)), these were based on circulating CK+ cells.

Linking CK− CTCs to an Epithelial-Mesenchymal Transition.

Figure 41:
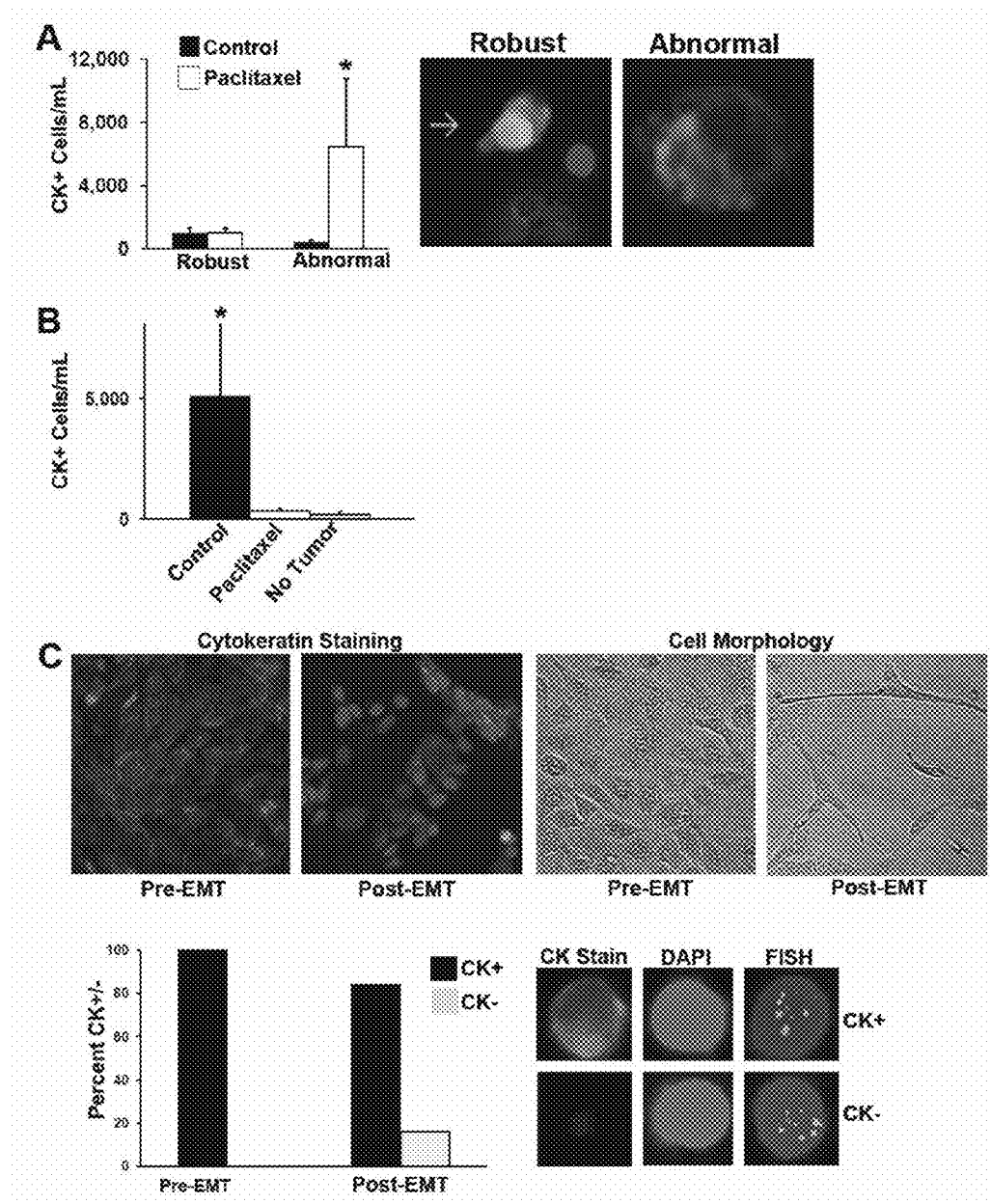
FIG. 41 shows characterization and capture of cytokeratin-negative cells after induction of EMT. (a) SKOV3 cells were either grown in regular culture media (Pre-EMT) or in serum-free media with 10 ng/mL TGF-beta (Post-EMT) for 72 hours. Pictured are representative immunofluorescent images (top) of Pre-EMT cells demonstrating 100% CK expression and areas of Post-EMT cells with absent CK expression. Approximately 20% of post-EMT cells were found to have complete loss of cytokeratin expression. Phase contrast images of the same cells (bottom) demonstrate a morphologic change characteristic of EMT. (b) Quantitative real-time PCR for markers of EMT of SKOV3 cells with and without TFG-beta treatment for 72 hours. (c) Following 72 hours, pre- and post-EMT cells were spiked ex vivo into mouse blood and run through the CEE™ microchannel. All pre-EMT cells that were captured were CK+ and had complex aneuploidy, while 16% of post-EMT cells were CK− and had similar complex aneuploidy. The bar graph represents ratios of CK+ and CK− complex aneuploid captured cells in each group. (d) Representative images of CK+ and CK− complex aneuploid SKOV3 cells are shown from within the microchannel. (e) HeyA8 cells cultured in regular media (Pre-EMT) or serum-free media with 10 ng/mL TGF-beta (Post-EMT) for 72 hours. Representative immunofluorescent images of Pre-EMT cells demonstrating nearly 100% CK expression and TGF-beta treated cells with absent CK expression. Approximately 60% of TGF-beta treated cells were found to have complete loss of cytokeratin expression. (f) HeyA8 cells were injected into 10 mice to establish a metastatic ovarian model. Once moribund, blood was collected from each mouse by cardiac puncture. Pictured are a CK+ and CK− CTC within the microchannel demonstrating hyperploidy of chromosomes 11 and 17. (g) Correlation of total aggregate tumor burden with enumeration of complex aneuploid CK− CTCs by mouse.

One possible mechanism giving rise to presence of CK− CTCs is EMT, a biological process reported to play a significant role in tumor progression and metastasis. Thus, there is growing interest in methods that enable capture and analysis of EMT-derived CTCs. To determine if our assay captures cells that have undergone EMT, we examined the effect of TGF-beta treatment on SKOV3 ovarian carcinoma cells. After 72 hours of treatment, CK staining was lost in about 20% of cells, correlating with an EMT morphologic change (FIG. 41a). Quantitative PCR analysis of these cells before and after TGF-beta treatment showed an increase in expression of mesenchymal markers (FIG. 4b). Cells, before and after treatment, were spiked ex vivo into mouse blood and run through the microchannel. All untreated cells captured were CK+, however, after TGF-beta treatment, 16% of the cells captured were CK− and had complex aneuploidy (FIG. 41c). Direct visualization of the FISH staining within the microchannel demonstrates these CK+ and CK− cells had nearly identical complex aneuploid patterns (FIG. 41d).

Next, to examine the utility of our CTC detection system for capturing tumor cells with EMT features in an in vivo setting, we examined the effect of TGF-beta treatment on HeyA8 ovarian carcinoma cells. After 72 hours of TGF-beta treatment, approximately 50-60% of cells lost their CK staining (FIG. 41e). To determine if these CK− cells can be captured in circulation, we established a metastatic orthotopic model with HeyA8 cells. Ten tumor-bearing mice were monitored for signs of morbidity, at which point approximately 350 μL of blood was obtained per mouse by cardiac puncture prior to sacrifice. All sites of metastatic tumor were carefully removed and weighed. Both CK+ and CK− complex aneuploid CTCs were isolated from circulation within the microchannel (FIG. 41f). Enumeration of complex aneuploid CK− CTCs correlated with aggregate tumor burden (FIG. 41g).

Discussion.

Collectively, these results confirm the utility of the microfluidics platform described in this example as a reliable method for assay development and for efficient recovery of CTCs. We observed that a potentially important population of cancer cells is present in circulation that would likely be missed by standard detection criteria. Identification of the full spectrum of CTCs would permit more efficient and directed analysis among patient specimens where heterogeneous CTC populations are expected. Namely, detection of EMT-derived CTCs has been widely hypothesized as a population of cells that are missed by current platforms (Mego M, et al., Nat Rev Clin Oncol, 7: 693-701 and Cristofanilli M, et al., JAMA, 303: 1092-3). Our data indicate that these complex aneuploid CK− CTCs isolated in clinical samples may represent EMT-derived CTCs.

There are some recent reports of isolated CTCs expressing markers of EMT. For example, in metastatic breast cancer patients receiving standard therapies, CTCs correlated with more frequent expression of EMT markers (Twist1, Akt2 and PI3Kalpha) in those who were resistant to treatment (Aktas B, et al., Breast Cancer Res, 11:R46 (2009)). Similar reports have found that CTCs can co-express both epithelial (cytokeratin and e-cadherin) and mesenchymal (vimentin and n-cadherin) markers (Armstrong A J, et al., Mol Cancer Res (2011) and Hou J M, et al., Am J Pathol 175 808-16 (2009)). Likewise, a higher incidence of CK+Vimentin+ and CK+Twist+CTCs was found in metastatic breast cancer patients versus women with earlier stage disease (Kallergi G, et al., Breast Cancer Res 13:R59 (2011)). These studies suggest a continuum in the spectrum of epithelial differentiation to mesenchymal phenotype, suggesting that CTCs may have a partial EMT phenotype (Mego M, et al., Nat Rev Clin Oncol 7:693-701). However, these platforms may miss clinically relevant populations of CTCs because they rely upon cytokeratin for CTC detection. Here, we describe linking CK− CTCs to EMT.

Interestingly, we observed similar ratios of total CK+CTCs to complex aneuploid CK+ and CK− CTCs in three common cancer types. For example, only 24.3% of CK+CTCs in Her-2-neu positive breast cancer patients were found to have Her-2 amplification. This suggests that the classically defined CTC (CK+/CD45−/DAPI+) may over-represent cells that are of tumor origin. The FISH probes used in colorectal and ovarian cancer patients are unlikely to detect all CTCs with complex aneuploidy, suggesting that more complex aneuploid CK+ and CK− cells are likely still missed. However, the platform described herein allows for adaptability in selection of capture antibodies as well as use of different FISH probes and detection antibodies for immunofluorescence.

This platform enables efficient assay development given the ability to interrogate all recovered cells for confirmation of success in targeted cell capture (i.e. detection of HER2-amplified CK− cells). While using only a limited number of FISH probes is unlikely to find all CK+ and CK− cells with complex aneuploidy, more sophisticated interphase analysis may be considered. To the extent that CTCs represent a window into a patient's tumor, the present invention provides a new method for capturing and examining previously unrecognized CTC populations. Studies are clearly warranted to further classify distinct sub-types of CTCs. Further study of CK− CTCs may provide new insights into mechanisms of EMT and the possibility of interrupting the metastatic cascade.

All publications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for evaluating a sample for the presence or absence of a target or biomarker, wherein the method comprises
   contacting the sample with a mixture comprising a first binding entity and a third binding entity to allow binding interaction and form a pre-loading mixture, wherein the first binding entity specifically binds to a target entity on the target or biomarker, wherein the first binding entity is an antibody or antibody cocktail that is not conjugated to a detectable or capturable entity, and wherein the third binding entity is an antibody that specifically binds to the first binding entity;
   contacting the pre-loading mixture with a surface, wherein the surface is coated with a second binding entity capable of specifically binding to the third binding entity to form a second complex comprising the second binding entity and the first complex,
   wherein the second binding entity is a different type of binding molecule than the first binding entity; and
   detecting the presence of the target or biomarker on the surface.

2. The method of claim 1, wherein the target is a rare cell in the biological sample.

3. The method of claim 1, wherein the method does not involve cytokeratin staining.

4. The method of claim 1, wherein the target is CK−.

5. The method of claim 1, wherein the biomarker is aneuploidy of chromosomes 1, 3, 4, 7, 8, 11, 17 and/or 20.

6. The method of claim 1, wherein the biomarker is monosomy or trisomy 8, 11, and/or 17.

7. The method of claim 1, wherein the biomarker is monosomy 8, 11, and/or 17.

8. The method of claim 1, wherein the biomarker is monosomy or tetrasomy 17 or 20.

9. The method of claim 1, wherein aneuploidy is evaluated by fluorescence in-situ hybridization (FISH).

10. The method of claim 1, wherein the first binding entity is a primary antibody, the third binding entity is a biotinylated secondary antibody, and wherein the second binding entity is avidin, streptavidin or neutravidin.

11. The method of claim 1, wherein the sample is obtained from a patient prior to contacting the sample with the first and third binding entity, and wherein the presence or absence of the target or biomarker in the sample is indicative of a condition or disease in the patient.

12. The method of claim 11, wherein the condition or disease is a cancer, a malignancy, a drug selectivity, or a drug sensitivity.

13. The method of claim 12, further comprising, detecting an additional marker of malignancy.

14. The method of claim 13, wherein the additional marker of malignancy is Her2 expression.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Homo sapiens

<400> SEQUENCE: 1
tccaagcctg acctcactgc                    20

<210> SEQ ID NO 2
<211> LENGTH: 20
<212> TYPE: DNA
<213> ORGANISM: Homo sapiens

<400> SEQUENCE: 2
ttcatactgc tggcgcacat                    20

<210> SEQ ID NO 3
<211> LENGTH: 19
<212> TYPE: DNA
<213> ORGANISM: Homo sapiens

<400> SEQUENCE: 3
gccattgatg cggatgatc                     19

<210> SEQ ID NO 4
<211> LENGTH: 20
<212> TYPE: DNA
<213> ORGANISM: Homo sapiens

<400> SEQUENCE: 4
cctgtaccgc agcattccat                    20

<210> SEQ ID NO 5
<211> LENGTH: 22
<212> TYPE: DNA
<213> ORGANISM: Homo sapiens

<400> SEQUENCE: 5
tcgacttcct gtaccaggtc ct                 22

```
<210> SEQ ID NO 6
<211> LENGTH: 20
<212> TYPE: DNA
<213> ORGANISM: Homo sapiens

<400> SEQUENCE: 6
ccatcttgga gtccagctcg                                                   20

<210> SEQ ID NO 7
<211> LENGTH: 19
<212> TYPE: DNA
<213> ORGANISM: Homo sapiens

<400> SEQUENCE: 7
cccaaggccg tagagctga                                                    19

<210> SEQ ID NO 8
<211> LENGTH: 21
<212> TYPE: DNA
<213> ORGANISM: Homo sapiens

<400> SEQUENCE: 8
gcttttgcca ctgtcctcat c                                                 21
```